(12) United States Patent
Wang et al.

(10) Patent No.: US 9,921,406 B2
(45) Date of Patent: Mar. 20, 2018

(54) TARGETED DUAL-AXES CONFOCAL IMAGING APPARATUS WITH VERTICAL SCANNING CAPABILITIES

(75) Inventors: Thomas D. Wang, Ann Arbor, MI (US); Katsuo Kurabayashi, Ann Arbor, MI (US); Kenn Oldham, Ann Arbor, MI (US); Zhen Qiu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1536 days.

(21) Appl. No.: 12/916,159

(22) Filed: Oct. 29, 2010

(65) Prior Publication Data

US 2011/0125029 A1    May 26, 2011

Related U.S. Application Data

(60) Provisional application No. 61/256,937, filed on Oct. 30, 2009.

(51) Int. Cl.
*A61B 5/00* (2006.01)
*G02B 26/10* (2006.01)
(Continued)

(52) U.S. Cl.
CPC .......... *G02B 26/101* (2013.01); *A61B 5/0068* (2013.01); *A61B 5/0073* (2013.01);
(Continued)

(58) Field of Classification Search
CPC . A61B 2503/40; A61B 5/0068; A61B 5/0073; A61B 5/4255; G01N 21/6458;
(Continued)

(56) References Cited

U.S. PATENT DOCUMENTS 5,324,633 A * 6/1994 Fodor et al. ................. 435/6.12
6,351,325 B1   2/2002 Mandella et al.
(Continued)

OTHER PUBLICATIONS

Akyol et al., Generating somatic mosaicism with a Cre recombinase-microsatellite sequence transgene, Nat. Methods, 5:231-3 (2008).
(Continued)

*Primary Examiner* — Ruth S Smith
(74) *Attorney, Agent, or Firm* — Marshall, Gerstein & Borun LLP

(57) ABSTRACT

An optical device is described that may be used as a microscope system for real-time, three-dimensional optical imaging. The device includes a miniature, fiber optic, intravital probe microscope that uses a dual-axes confocal architecture to allow for vertical scanning perpendicular to a surface of the sample (e.g., a tissue surface). The optical device can use off-axis illumination and collection of light to achieve sub-cellular resolution with deep tissue penetration. The optical device may be used as part of an integrated molecular imaging strategy using fluorescence-labeled peptides to detect cell surface targets that are up-regulated by the epithelium and/or endothelium of colon and breast tumors in small animal models of cancer.

42 Claims, 29 Drawing Sheets

(51) Int. Cl.
 *G01N 21/64* (2006.01)
 *G02B 21/00* (2006.01)
 *G02B 26/08* (2006.01)
(52) U.S. Cl.
 CPC ....... *A61B 5/4255* (2013.01); *G01N 21/6458* (2013.01); *G02B 21/0028* (2013.01); *G02B 21/0036* (2013.01); *G02B 21/0076* (2013.01); *G02B 26/0841* (2013.01); *A61B 2503/40* (2013.01)
(58) Field of Classification Search
 CPC ............ G02B 21/0028; G02B 21/0036; G02B 21/0076; G02B 26/0841; G02B 26/101
 USPC ........... 600/407, 476, 478; 359/196.1, 198.1, 359/201.1; 250/201.3, 203.3
 See application file for complete search history.

(56) References Cited

U.S. PATENT DOCUMENTS

| | | | |
|---|---|---|---|
| 6,369,928 | B1 | 4/2002 | Mandella et al. |
| 6,414,779 | B1 | 7/2002 | Mandella et al. |
| 6,441,356 | B1 | 8/2002 | Mandella et al. |
| 6,487,349 | B2 | 11/2002 | Wach et al. |
| 6,522,444 | B2 | 2/2003 | Mandella et al. |
| 6,590,703 | B2 | 7/2003 | Park et al. |
| 6,713,742 | B2 | 3/2004 | Mandella et al. |
| 7,129,472 | B1 | 10/2006 | Okawa et al. |
| 7,130,042 | B2 | 10/2006 | Kino et al. |
| 7,242,521 | B2 | 7/2007 | Mandella et al. |
| 7,544,162 | B2 | 6/2009 | Ohkubo |
| 7,561,326 | B2 | 7/2009 | Funk et al. |
| 2003/0034431 | A1* | 2/2003 | Mandella et al. ......... 250/201.3 |
| 2004/0059321 | A1* | 3/2004 | Knopp et al. .................. 606/10 |
| 2004/0085617 | A1* | 5/2004 | Helsel et al. ................. 359/292 |
| 2006/0061850 | A1* | 3/2006 | Fu et al. ....................... 359/223 |
| 2006/0077787 | A1* | 4/2006 | Itagi et al. ................. 369/44.23 |
| 2006/0119228 | A1* | 6/2006 | Florian et al. ............... 310/358 |
| 2007/0269199 | A1* | 11/2007 | Mori et al. .................... 396/322 |
| 2008/0312096 | A1* | 12/2008 | Gray et al. ....................... 506/9 |
| 2009/0235396 | A1* | 9/2009 | Wang et al. ..................... 850/6 |
| 2010/0045141 | A1 | 2/2010 | Pulskamp et al. |
| 2010/0045142 | A1 | 2/2010 | Pulskamp et al. |
| 2011/0032590 | A1* | 2/2011 | Terada ............... G02B 26/0858 359/199.4 |

OTHER PUBLICATIONS

Ataman et al., Analysis of parametric resonances in comb-driven microscanners, In: Conference on MEMS, MOEMS and Micromachining, Strasbourg, France, pp. 128-36 (2004).
Burns et al., A novel chemokine receptor for SDF-1 and I-TAC involved in cell survival, cell adhesion, and tumor development, J. Exp. Med., 203:2201-13 (2006).
Christmann et al., The cystine knot of a squash-type protease inhibitor as a structural scaffold for *Escherichia coli* cell surface display of conformationally constrained peptides, Protein Eng., 12:797-806 (1999).
Cwirla et al., Peptide agonist of the thrombopoietin receptor as potent as the natural cytokine, Science, 276:1696-9 (1997).
Domke et al., Amplifying transimission and compact suspension for a low-profile, large-displacement piezoelectric actuator, J. Micromech. Microeng., May 21(6) 067004 (2011).
Hinoi et al., Mouse model of colonic adenoma-carcinoma progression based on somatic Apc inactivation, Cancer Res., 67:9721-30 (2007).
Hsiung et al., Detection of colonic dysplasia in vivo using a targeted heptapeptide and confocal microendoscopy, Nat. Med., 14:454-58 (2008).
International Search Report and Written Opinion from PCT/US2010/054806 dated May 31, 2011.
Jensen et al., Effect of nanoscale heating on electrical transport in RF MEMS switch contacts, J Microelectromechanical Systems, 14:935-46 (2005).
Kelly et al., Detection of invasive colon cancer using a novel, targeted, library-derived fluorescent peptide, Cancer Res., 64:6247-51 (2004).
Kelly et al., Isolation of a colon tumor specific binding peptide using phage display selection, Neoplasia, 5:437-44 (2003).
Kolmar, Alternative binding proteins: biological activity and therapeutic potential of cystine-knot miniproteins, FEBS J., 275:2684-90 (2008).
Konotop et al., Parametric resonance of a defect mode in a 2D photonic crystal, Phys. Rev. B, 6412:7 (2001).
Lincoff et al., Platelet glycoprotein IIb/IIIa receptor blockade in coronary artery disease, J. Am. Coll. Cardiol., 35:1103-15 (2000).
Liu et al., Micromirror-scanned dual-axis confocal microscope utilizing a gradient-index relay lens for image guidance during brain surgery, J. Biomed. Optics, Mar.-Apr.; 15(2):026029 (2010).
Liu et al., A dual-axes confocal reflectance microscope for distinguishing colonic neoplasia, J. Biomed. Optics, 11:054019-1-10 (2006).
Liu et al., Efficient rejection of scattered light enables deep optical sectioning in turbid media with low-NA optics in a dual-axes confocal architecture, J. Biomed. Optics, 13:034020 (2008).
Liu et al., Miniature near-infrared dual-axes confocal microscope utilizing a two-dimensional microelectromechanical systems scanner, Optics Letters, 32:256-8 (2007).
Liu et al., Quantifying cell-surface biomarker expression in thick tissues with ratiometric three-dimensional microscopy, Biophys. J., Mar. 18;96(6):2405-14 (2009).
Miao et al., CXCR7 (RDC1) promotes breast and lung tumor growth in vivo and is expressed on tumor-associated vasculature, Proc. Natl. Acad. Sci. USA, 104:15735-40 (2007).
Oldham et al., Thin-film PZT lateral actuators with extended stroke, J. Microelectromechanical Systems, 17:890-3 (2008).
Polcawich et al., Surface micromachined microelectromechanical ohmic switches using thin-film piezoelectric actuators, IEEE Trans. on Microwave Theory and Techniques, 55:2642-4 (2007).
Proost et al., Proteolytic processing of CXCL11 by CD13/aminopeptidase N impairs CXCR3 and CXCR7 binding and signaling and reduces lymphocyte and endothelial cell migration, Blood, 110:37-44 (2007).
Qiu et al., Large displacement vertical translational actuator based on piezoelectric thin-films, J. Micromech. Microeng., Feb. 20(7):075016 (2010).
Ra et al., Three-dimensional in vivo imaging by a handheld dual-axes confocal microscope, Optics Express, 16:7224-32 (2008).
Silverman et al., Engineered cystine-knot peptides that bind alpha(v)beta(3) integrin with antibody-like affinities, J. Mol. Biol., 385:1064-75 (2009).
Souriau et al., New binding specificities derived from Min-23, a small cystine-stabilized peptidic scaffold, Biochemistry, 44:7143-55 (2005).
Turner et al., Five parametric resonances in a microelectromechanical system, Nature, 396:149-52 (1998).
Wang et al., Confocal fluorescence microscope with dual-axis architecture and biaxial postobjective scanning, J. Biomed. Optics, 9:735-42 (2004).
Wang et al., Dual axes confocal microscope for high resolution in vivo imaging, Optics Letters, 28:414-16 (2003).
Wang et al., Dual axes confocal microscope with post-objective scanning and low coherence heterodyne detection, Optics Letters, 28:1915-17 (2003).
Wang, In-Vivo Microscopy. In: Intes et al., Translational Multi-Modality Optical Imaging 2008, Artech House, MA, pp. 19-32.
Wentzel et al., Sequence requirements of the GPNG beta-turn of the Ecballium elaterium trypsin inhibitor II explored by combinatorial library screening, J. Biol. Chem., 274:21037-43 (1999).
Wong et al., Improved rejection of multiply-scattered photons in confocal microscopy using dual-axes architecture, Optics Letters, 32:1674-6 (2007).

(56) References Cited

OTHER PUBLICATIONS

Wu et al., Loading dynamics of optical trap and parametric excitation resonances of trapped atoms, J. Appl. Physics, 100:054903 (2006).

Yu et al., Realization of parametric resonances in a nanowire mechanical system with nanomanipulation inside a scanning electron microscope, Phys. Rev. B, 66:4 (2002).

Zurita et al., Combinatorial screenings in patients: the interleukin-11 receptor alpha as a candidate target in the progression of human prostate cancer, Cancer Res., 64:435-9 (2004).

\* cited by examiner

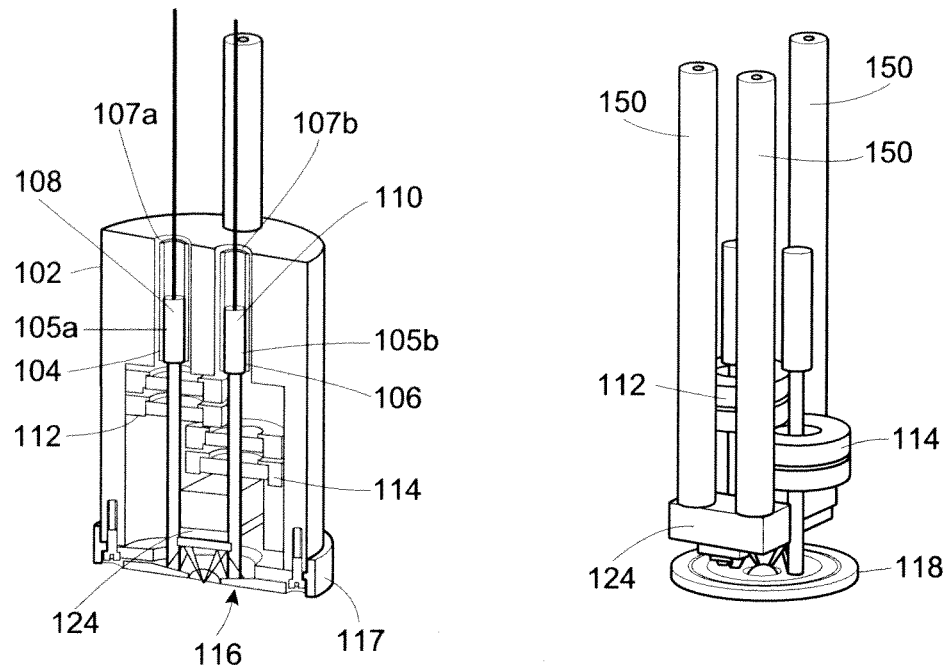
Figure 11
Figure 13
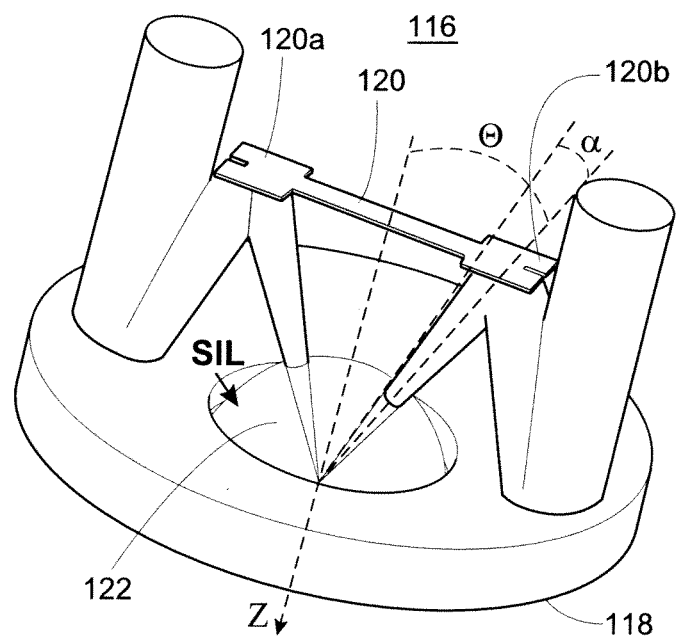
Figure 12

*1* DRIE of coarse patterns (Mask 1)

*2* Upper device layer bonding

*3* Self-alignment mask patterning (Mask 2) after LTO deposition

*4* Partial etching of LTO (Mask 3)

*5* DRIE of upper device layer

*6* DRIE of lower device layer by Mask 2 and upper device layer by Mask 3

*7* Backside pattering and DRIE for release (Mask 4)

☐ Single crystal silicon (SCS)

▨ Thermal oxide

■ Low temperature oxide (LTO)

| Parameters | Dual Axes | |
|---|---|---|
| λ(nm) | 676 | 785 |
| n | 1.4 | 1.4 |
| α | 0.128 | 0.128 |
| Θ (deg) | 24 | 24 |
| FOV (μm²) | 500x800 | 500x800 |
| Δx (μm) | 1.6 | 1.6 |
| Δy (μm) | 1.4 | 1.7 |
| Δz (μm) | 3.5 | 4.2 |

TARGETED DUAL-AXES CONFOCAL IMAGING APPARATUS WITH VERTICAL SCANNING CAPABILITIES

CROSS REFERENCE TO RELATED APPLICATIONS

This application claims the benefit of U.S. Provisional Application No. 61/256,937, filed Oct. 30, 2009, the entirety of which is expressly incorporated herein by reference.

STATEMENT OF GOVERNMENT INTEREST

This invention was made with government support under CA136429 and CA093990 awarded by the National Institutes of Health. The government has certain rights in the invention.

BACKGROUND OF THE DISCLOSURE

Field of the Disclosure

The disclosure relates generally to microscope imaging of tissue and, more particularly, to devices for dual-axes confocal microscopy.

Brief Description of Related Technology

While tremendous advances have been made in technologies for whole body molecular imaging, including PET, SPECT, MRI, and ultrasound, techniques for visualizing biological phenomenon with sub-cellular resolution in optically thick tissue are lacking. In addition, these conventional techniques lack the ability to obtain vertical cross-sectional views of tissue. Take two common forms of cancer, for example, colorectal cancer and breast cancer. Researchers are unable to properly image cancer tissue with vertical cross-sectional views at the sub-cellular level for either of these types of cancer.

Colorectal cancer claims approximately 149,000 new cases annually in the United States, where the rate of incidence is among the highest in the world (48.2 cases/100,000 population in 1998-2004). The average lifetime risk for developing the disease is 1 in 20 in the industrialized world. Yet, despite the widespread availability of colonoscopy, colorectal carcinoma remains the second most common cause of cancer; and the mortality and morbidity associated with this disease is far more common than expected. The miss rate for colonic adenomas, as determined by tandem colonoscopy, has been found to be as high as 22%; and a significant number of cases of colorectal cancers (2.4 cancer/1000 person-years) have been diagnosed within a year following screening colonoscopy. Moreover, there is evidence that up to 25% of spontaneously occurring adenomas arise from sporadically occurring flat or depressed lesions that may be difficult to visualize by conventional white light endoscopy. These lesions frequently contain high grade dysplasia and progress more rapidly through the adenoma-carcinoma sequence than polypoid adenomas. To develop better strategies for risk stratification and early detection, a greater understanding of molecular target expression patterns within the colon tissue over time is needed.

Breast cancer in women is the most common cancer in the U.S. and the second-most common cause of death by cancer. There are approximately 182,000 new cases of invasive breast cancer and about 68,000 new cases of in situ breast cancer each year. Current methods for breast cancer screening include self breast exams, mammography, ultrasound, and MRI. All of these techniques are based on the presence of gross morphological changes in either size or density of malignant lesions for detection. This disease results from multiple genetic and environmental factors, including defects in DNA repair genes, abnormal growth factor synthesis, dysregulated cell signaling, elevated estrogen exposure, and failure of immune surveillance. The presence of molecular changes occur well in advance of structural abnormalities, and more sophisticated imaging methods are needed to improve our understanding of disease mechanisms and to develop more effective screening methods to improve monitoring of treatment efficacy.

One imaging technique for early stage diagnosis is intra-vital imaging of tissue epithelium. Transformed cells that develop into cancer in the colon and breast originate within the epithelium of the mucosa and ducts, respectively, as shown below in FIG. 1. Infra-vital microscopy is a useful tool for studying the molecular mechanisms of epithelial cancer biology in vivo because this technique can be used to directly access this thin, superficial layer of tissue to provide the highest resolution possible with imaging in live animals. A miniature fiber optic instrument can be placed in contact with the tissue surface and collect real time images with sub-cellular resolution. These instruments, for example, can be inserted into the colon and or held by hand onto the breast to perform longitudinal studies in small animal models of cancer. With intra-vital imaging, non-terminal studies can be performed using each animal as its own control. This approach can significantly reduce the number of testing specimens needed and can provide a more robust study design. In addition, this technique can be used to study ligand-receptor interactions and cell tracking behavior in vivo, processes that are difficult to observe with any other imaging modality.

As shown in FIG. 1, normal colonic epithelium transforms to a pre-malignant condition (dysplasia) prior to evolving into carcinoma, viewing the illustration from left to right. Subtle molecular changes develop first in the crypts prior to morphological changes in the tissue. Imaging in the vertical cross-section (plane perpendicular to tissue surface) is the desired orientation for detecting disease because the epithelium differentiates in the vertical direction (basilar to luminal direction). The vertical cross-section provides a global view of the normal and abnormal micro-architectural changes, including the vascular endothelium, in the epithelium with a consistent orientation. This view allows the observer to detect subtle differences associated with the early presence of disease in comparison to that of the horizontal cross-section (parallel to tissue surface).

While useful, intra-vital microscope techniques are limited. One of the challenges in performing high resolution (sub-cellular) imaging in live specimens (e.g., animal models) is the ability to overcome motion artifact, including respiratory displacement, heart beating, and organ peristalsis. Conventional intra-vital microscopes use bulk optic objectives that are fixed to large, stationary platforms. As a result, motion will occur in live animals relative to the objective that appear exaggerated in the relatively small fields-of-view of intra-vital microscopes, typically on the order of several hundred microns. On the other hand, a miniature intra-vital microscope has the size and weight to move relative to the bodily motion of the animal during the imaging session, thus substantially reduce the motion artifact in the images. Fiber coupling allows for the image to be transmitted to the detector. Furthermore, the small size of these instruments provides much greater positioning accuracy of the objective lens onto target organs in the animal.

Recent advances in the development of micro-lenses and scanners have resulted in the development of a number of miniature intra-vital microscopes for high resolution imaging in small animals. These instruments are designed for a size that can be inserted in the colon to evaluate the epithelium of the distal mucosa or hand held against the body wall to image the epithelium of breast ducts. However, these microscopes all use the single axis configuration where the pinhole (fiber) and objective are located along one main optical axis. A high numerical (NA) objective is needed to achieve sub-cellular resolution and maximum light collection, and the same objective is used for both the illumination and collection of light. In order to scale down the dimension of these instruments for small animal imaging, the diameter of the objective must be reduced to ~5 mm or less. As a consequence, the working distance, imaging depth, and field-of-view are also decreased, as shown by the progression of the 3 different objective diameters (A→B→C) in FIG. 2, with corresponding illustrations of example working distances $WD_A$, $WD_B$, and $WD_C$. The range of sizes is illustrated in the right panel by an objective from the Olympus IV100 where upper element (A) represents the diameter of a conventional objective and the lower reflects that of a miniature objective (C), scale bar 5 mm.

Generally, imaging tissue through the use of light is a very powerful tool, because this modality can achieve sub-cellular resolution in real time, a level of performance that cannot be matched by any other imaging modalities (such as PET scanner, CT scans, MRI, etc.). However, light is highly scattered by tissue, and sophisticated methods are needed to produce clear images. Confocal microscopy is one form of intra-vital microscope that uses a pinhole placed in between the objective lens and the detector to allow only the light that originates from within a tiny volume below the tissue surface to be collected. All other sources of scattered light do not have the correct path to be detected, and thus become "spatially filtered." This process is known as optical sectioning and can produce a high resolution image from a thin slice of tissue below the surface. These images can be collected at sufficiently fast frame rates to observe biological behavior in small animal models of disease with minimal disturbance from motion artifacts caused by breathing displacements and heart beating. Recent advancements in miniaturization of optics, availability of fiber-optics, and emergence of micro-scanners have allowed for the technique of confocal microscopy to be performed in vivo through medical endoscopes to perform rapid, real-time optical assessment of tissue pathology.

Traditional confocal intra-vital microscopes used a single-axis optical design, while recently some have proposed a dual-axes confocal architecture. For a single-axis design, the pinhole (i.e., the single mode optical fiber) and objective are located along the same optical axis. As a result, a high numerical aperture (NA) objective is needed to achieve sub-cellular resolution, limiting the working distance as discussed above in reference to FIG. 2. As a consequence, the single-axis configuration uses a scanning mechanism (mirror) that is placed on the pinhole side of the objective, or in the pre-objective position, and this design cannot be scaled down in dimension without loss of working distance or field-of-view. Furthermore, much of the light that is scattered by the tissue present between the objective and focal volume (dashed lines) is collected with the high NA objective, reducing the dynamic range of detection. See, e.g., FIG. 3A.

The more recent dual-axes architecture, shown in FIG. 3B, uses two fibers and low NA objectives for separate illumination and collection of light, using the region of overlap between the two beams (focal volume) to achieve sub-cellular resolution. The low NA objectives create a long working distance so that the scan mirror can be placed on the tissue side of the lens, or in the post-objective position. Very little of the light that is scattered by tissue along the illumination path (dashed lines) is collected by the low NA objective collection objective, thus the dynamic range is significantly improved. Consequently, theoretically optical sections can be collected in both vertical (V) and horizontal (H) planes with dual axes, as compared to horizontal only for single axis. Vertical cross-sections show the relationship among tissue microstructures as they vary with depth, and are the preferred view of pathologists. The single-axis configuration does not have sufficient dynamic range to provide this view.

In intra-vital microscopy, scanning of the focal volume is performed to create an image. In the single-axis architecture, the limited working distance requires that the scan mirror be placed in the pre-objective position, as shown in FIG. 4A, i.e., before the incident light from the fiber/pinhole hits the objective. The mirror is used for scanning which steers the beam at various angles to the optical axis (dashed line) and introduces off-axis aberrations that distort the focal volume. In addition, because the FOV is proportional to the scan angle and the focal length, the diameter of the objective limits the maximum scan angle. As this dimension is reduced, the focal length and FOV are also diminished (arc-line). In the dual-axes configuration, the low NA objectives create a long working distance that allows for the scanner to be placed in the post-objective position. This design feature is useful for scaling the size of the instrument down to millimeter dimensions for in vivo imaging in small animal models without losing performance. As shown in FIG. 4B, the illumination light is always incident on-axis to the objective. In this scanning geometry, the scan mirror can sweep a diffraction-limited focal volume over an arbitrarily large FOV (arc-line), limited only by the maximum deflection angle of the mirror.

Recently, a dual-axes confocal architecture was implemented in a 5 mm diameter instrument package, as shown in FIG. 5A. The scanhead uses a replicated parabolic mirror as the low NA focusing objective, and a MEMS (micro-electro-mechanical-systems) mirror to perform scanning in the horizontal (XY) plane. Axial (Z-axis) translation is performed with a stepper (micro-) motor. Illumination and collection of light is delivered separately by two single mode optical fibers, and control wires contained within an umbilical provide power and scanning signals to the MEMS mirror and micro-motor. This instrument can be either inserted into the colon or held by hand against the breast of genetically engineered mice, as shown by FIG. 5B. The instrument can collect fluorescence images in horizontal cross-sections from a depth of z=0 to 500 μm in 3 μm intervals. The simple Z-axis scanner used in this design is limited and requires large amounts of time (on the order of 50 seconds) to perform a full Z-axis scan. Such limited scannability in the Z-axis means that the conventional dual-axes configuration is not sufficiently fast to collect vertical cross-sectional images.

Thus, there is a need for a dual-axes scanning assembly that offers sufficient Z-axis and XY-plane scanning, in a configuration that can achieve high scan rates (such as real time scan rates) over a volume of tissue. Furthermore, it is desirable to use such a device for more accurate pathology recognition and earlier detection.

SUMMARY OF THE DISCLOSURE

To address the foregoing, the present application describes an optical device that may be used as a microscope system for real-time, three-dimensional optical imaging at depths substantially greater than existing intra-vital imaging technologies. The optical device comprises a probe that can be used as part of an integrated molecular imaging strategy using fluorescence-labeled peptides to detect cell surface targets that are up-regulated by the epithelium and/or endothelium of colon and breast tumors in small animal models of cancer. A miniature, fiber optic, intra-vital probe microscope that uses the dual-axes confocal architecture has been developed to detect expressions of molecular targets through vertical cross-sectional imaging. The innovative approach uses off-axis illumination and collection of light to achieve sub-cellular resolution (e.g., <5 µm) with deep tissue penetration (e.g., >500 µm). Moreover, the design geometry can overcome blurring caused by tissue scattering to achieve superior dynamic range for fluorescence detection. The design is highly sensitive to the subtle changes in normal vertical patterns of tissue differentiation that can reveal the presence of early cancer biomarkers.

The present dual-axes design has advantages over single-axis two-photon microscopy, which is a commonly used method for performing intra-vital imaging studies. The two-photon effect occurs when two lower energy (longer wavelength) photons arrive at a biomolecule simultaneously to excite fluorescence. The probability of absorbing two photons increases with the square of the intensity, thus a high numerical objective in the single axis configuration is used to maximize the intensity at the focus. Because of this physical principle, there is less sensitivity to tissue scattering and reduced photobleaching in comparison to that for single photon fluorescence. Moreover, the longer excitation wavelengths used provide deeper tissue penetration. However, most two-photon instruments use a large, bulk optic objective that requires a large region of exposure to image the target organs, resulting in terminal experiments. Recently, fiber-optic two-photon instruments have been developed that use a hollow-core (photonic bandgap) fiber. Near-infrared femtosecond pulses are focused by tiny gradient index (GRIN) micro-lens, and can collect images with a transverse and axial resolution of 1 and 8 µm, respectively. Because the pulse lengths are ultrashort, the pulses propagating through the fiber are sensitive to group velocity dispersion and self-phase modulation at high peak powers. These distort the pulse profile, lower efficiency, and reduce sensitivity. Furthermore, expensive light sources (lasers) are needed to provide the high peak powers and ultrashort pulses required to perform real time in vivo imaging. Also, these lasers need to be tuned to produce different excitation bands, thus multi-color images are collected sequentially rather than simultaneously. This limits the ability of two-photon microscopy to study ligand-receptor interactions and cell tracking behavior.

The present techniques, as will be described further, are able to employ a low NA objective lens (e.g., <0.3). The techniques offer many of the same advantages of two-photon microscopy in terms of reduced tissue scattering, deeper tissue penetration, and less photobleaching. In addition, however, the present dual-axes design provides a significant improvement in dynamic range by collecting light off-axis of the illumination beam so that vertical cross-sectional images can be achieved. This orientation is valuable to viewing the vertical epithelial differentiation patterns in tissue such as the colon and breast to better understand the molecular mechanisms of cancer biology. Also, the dual-axes architecture can be implemented with a relatively inexpensive light source (semiconductor lasers) that cost only a tiny fraction of that for ultra-fast (femtosecond) lasers. In addition, as discussed below, in some examples multiple light sources can be used at the same time (multiplexed) to perform multi-color excitation where the fluorescence images are collected simultaneously using the same optical fibers and objectives. This powerful feature can be used to observe ligand-receptor interactions and cell tracking behavior, both very important biological phenomena.

In comparison, the two-photon effect requires a tight focus that needs a high numerical aperture objective (typically >0.6). Thus, off-axis light collection and post-objective scanning cannot be performed with present two-photon techniques; and the level of performance for in vivo imaging has been limited so far to horizontal cross-sectional images.

In the examples illustrated herein below, the proposed dual-axes architecture is used to form an optical probe capable of targeted imaging of molecular changes that occur in transformed cells and tissues that progress to cancer in the colon and breast provide critical imaging targets. These improvements in imaging technology, for identifying and localizing the presence of these cancer biomarkers, may dramatically improve our ability to perform early detection, risk stratification, and therapeutic monitoring of cancer. Generally speaking, molecular probes have demonstrated tremendous potential for detecting early neoplastic changes in small animal models by their high binding specificity to pre-malignant targets. As used herein, "specificity" means that the molecular probe can identify, bind and/or interact with one target with a higher affinity and/or avidity compared to all other targets. For example, the use of monoclonal antibodies to bind cell surface targets in tumors in the colon and breast for diagnosis and therapy has been demonstrated. In addition, proteases are proteolytic enzymes that are important targets that play an important role in cell proliferation, invasion, apoptosis, angiogenesis, and metastasis. Examples include cathepsin B and matrix metalloproteinases. Molecular probes that bind to these targets can be radiolabeled for detection on whole body imaging, such as with PET and SPECT, and can be fluorescence labeled for detection on endoscopy and microscopy.

The dual-axes architectures described herein provide an imaging geometry capable of overcoming tissue scattering issues of conventional imaging modalities, while providing superior dynamic range, allowing for the collection of vertical cross-sectional images. This orientation is valuable for visualizing the epithelium (and other tissue) because this tissue differentiates in the plane perpendicular to the tissue surface. No other molecular imaging modality can visualize the epithelium in this orientation. The present application, however, describes dual-axes microscopy devices that are capable of sub-cellular resolution and fast imaging speeds that can be formed into the small package dimensions desired for intra-vital microscopy. This provides for better study of cell-protein and protein-protein interactions. Moreover, because this novel architecture can be scaled down in size to millimeter dimensions, the dual-axes architectures may be generalized for imaging the epithelium of hollow organs, such as the bladder, colon, esophagus, lung, and stomach, via a medical endoscope. Thus, this instrument can be used to guide tissue biopsy, increase the yield of disease detection, and reduce the risk of bleeding.

In some applications, the dual-axes architecture can be used to form optical probes that address an important need for a miniature intra-vital microscope and that provide sub-cellular resolution with deep tissue penetration in vertical cross-sections to visualize the perpendicular differentiation patterns of the epithelium and sub-epithelium in small animal models of cancer. The dual-axes confocal architecture provides a novel and powerful optical configuration that meets the demanding environment of live animal imaging with use of low numerical aperture objectives and post-objective scanning to achieve high dynamic range and scalability.

In accordance with one aspect of the disclosure, an optical probe comprises: a probe housing assembly having a proximal end and a distal end positioned at a sample, the probe housing defining a first beam channel to provide an illumination beam having and a second beam channel to provide a collection beam; and a scanning assembly mounted at the distal end of the probe housing, the scanning assembly having (1) a mirror assembly configured to focus an illumination beam path and a collection beam path at a region of interest within the sample where the illumination beam and the collection beam overlap to form a confocal beam region, the mirror assembly being configured to scan the confocal beam region along at least one transverse direction in the sample, and (2) a vertical scanning assembly configured to scan the confocal beam region along an vertical direction in the sample, wherein the vertical direction is orthogonal to the at least one transverse direction.

In accordance with another aspect of the disclosure, a confocal microscopy apparatus comprises: a probe comprising, (1) a housing assembly having a proximal end and a distal end positioned at a sample, the probe housing defining a first beam channel to provide an illumination beam having and a second beam channel to provide a collection beam and (2) a scanning assembly mounted at the distal end of the probe housing, the scanning assembly having (i) a mirror assembly configured to focus an illumination beam path and a collection beam path at a region of interest within the sample where the illumination beam and the collection beam overlap to form a confocal beam region, the mirror assembly being configured to scan the confocal beam region along at least one transverse direction in the sample, and (ii) a vertical scanning assembly configured to scan the confocal beam region along an vertical direction in the sample, wherein the vertical direction is orthogonal to the at least one transverse direction; a light source coupled to provide the illumination beam to the first beam channel; and a photodiode assembly coupled to receive the collection beam from the second beam channel and configured to produce an image of fluorescence energy contained within the collection beam.

In some embodiments, a method of detecting a cancerous cell in a mammal is provided comprising the step of administering a detectably labeled polypeptide to the mammal in an amount effective to detect the cancerous cell, the polypeptide having a property of preferentially binding to the cancerous cell relative to a non-cancerous cell and detecting the cancerous cell with an optical probe described herein.

In some aspects, the cancerous cell is selected from the group consisting of a colon cancer cell, a breast cancer cell, a skin cancer cell, an esophageal cancer cell, a liver cancer cell, a lung cancer cell, a brain cancer cell, a pancreatic cancer cell, a prostate cancer cell, and a bone cancer cell.

In another embodiment, a method of determining effectiveness of a treatment for cancer in a subject is provided comprising the step of administering a detectably labeled polypeptide to the subject in an amount effective to label a cancer cell, visualizing an amount of cells labeled with the detectably-labeled polypeptide, and comparing the amount to a previously visualized amount of cells labeled with the detectably-labeled polypeptide, wherein a decrease in the amount of labeled cells relative to the previously visualized amount of labeled cells is indicative of effective treatment.

In some embodiments, a kit for detecting a labeled polypeptide administered to a subject in need thereof is provided, the kit comprising a detectably labeled polypeptide having a property of preferentially binding to the cancerous cell relative to a non-cancerous cell, an optical probe as described herein, and instructions for use.

In some aspects, the subject is a human.

BRIEF DESCRIPTION OF THE DRAWING FIGURES

For a more complete understanding of the disclosure, reference should be made to the following detailed description and accompanying drawing figures, in which like reference numerals identify like elements in the figures, and in which:

FIG. 1 is an illustration of how a carcinoma of the colon arises from a transformation of normal epithelium to dysplasia. Subtle molecular changes develop first in the crypts prior to morphological changes in the tissue. An intra-vital microscope placed on the luminal surface of the tissue can be used to study the molecular progression of this disease longitudinally in small animal models. Imaging in the vertical cross-section (plane perpendicular to tissue surface) is the preferred orientation for detecting subtle differences in tissue differentiation patterns and for identifying the early presence of invasion, compared to the horizontal cross-section (parallel to tissue surface).

FIG. 2 is an illustration of the effect of numerical aperture on tissue illumination depth for various examples. For improved access to the epithelium in small animal models, the diameter of the intra-vital microscopy is to be reduced in size. Conventional microscopes use a single axis configuration where the incident beam is aligned on-axis with the objective. As the diameter of the objective is reduced from A)→B)→C), the working distance (WD), imaging depth, and field-of-view (FOV) are also diminished. Conventional intra-vital microscopes cannot easily image below the muscularis, as a result—the muscularis is an important landmark for assessing cancer progression and invasion. An example objective from the Olympus IV100 is shown in D) where upper element (arrow) represents the diameter of a conventional objective and the lower (arrowhead) reflects that of a miniature objective, scale bar 5 mm.

FIG. 3A is an illustration of a conventional single-axis confocal microscope configuration, having a fiber (pinhole) aligned with the optical axis of the objective, and requiring a high NA to achieve sub-cellular resolution. FIG. 3B is an illustration of a dual-axes architecture that uses separate, low NA objectives to achieve sub-cellular resolution and long working distance. Post-objective scanning provides a large field-of-view and instrument scalability to millimeter dimensions. Both vertical (V) and horizontal (H) cross-sectional images can be collected because of the reduced collection of light scattered by tissue (dashed orange lines).

FIG. 4A illustrates a pre-objective scanning in a conventional single axis configuration having the scan mirror placed on the fiber (pinhole) side of the objective because of the short working distance (WD), limiting the field-of-view and instrument scalability. FIG. 4B is a high-level illustration of a post-objective scanning in a dual-axes architecture having the scan mirror placed on the tissue side of the objective, allowing for large fields-of-view and instrument scalability down to millimeter dimensions.

FIG. 5A is an illustration of an example dual-axes probe device in the form of a confocal microscope. Illumination and collection of light is delivered separately by two single mode optical fibers, and control wires contained within an umbilical provide power and scanning signals to the micro-mirror and micro-motor in the scanhead. FIG. 5B illustrates an instrument that can be inserted into the colon and or held by hand onto the breast to perform longitudinal studies in small animal (mouse) models of cancer.

FIGS. 6A and 6B are plots that illustrate the high dynamic range of the dual-axes architecture. FIG. 6A plots, for non-scattering media, that the axial response of the single axis (dashed line) configuration falls off as $1/z^2$ and that for the dual-axes (solid line) design falls off as $\exp(-kz^2)$, resulting in a significant improvement in dynamic range. FIG. 6B plots, for scattering (turbid) media, the dynamic range. Introduction of tissue scattering shows that the dual-axes configuration maintains significantly greater dynamic range than that for single axis over a range of optical path lengths L (4.8, 6.4 and 8.0).

FIGS. 7A and 7B illustrate vertical cross-sectional images of epithelium with vertical depth of 500 µm. FIG. 7A illustrates for the esophagus, where squamous cells are seen on the left, and columnar (intestinal metaplasia) mucosa on the right show crypts with goblet cells. FIG. 7B illustrates for the colon, where many goblet cells can be seen in dysplastic crypts from a flat colonic dysplasia.

FIG. 8A is a horizontal cross-sectional image collected with a dual-axes confocal fluorescence microscope from a human U87MG xenograft tumor implanted subcutaneously in the flank of a nude mouse obtained in vivo at 50 µm depth using 785 nm excitation with intravenously administered indocyanine green (ICG). FIG. 8B is a 3D image generated from an axial stack of 400 sections with 1 µm thickness shows tumor volume.

FIG. 11 illustrates a cross-sectional view of the probe of FIGS. 9A-9C.

FIG. 12 illustrates a dual-axes scanhead that forms part of a scanning assembly for the optical probe of FIGS. 9A-9C.

FIG. 13 illustrates the dual-axes scanhead and a MEMS scanning actuator also forming part of a scanning assembly for the optical probe of FIGS. 9A-9C.

Figure 15A:
Figure 15B:
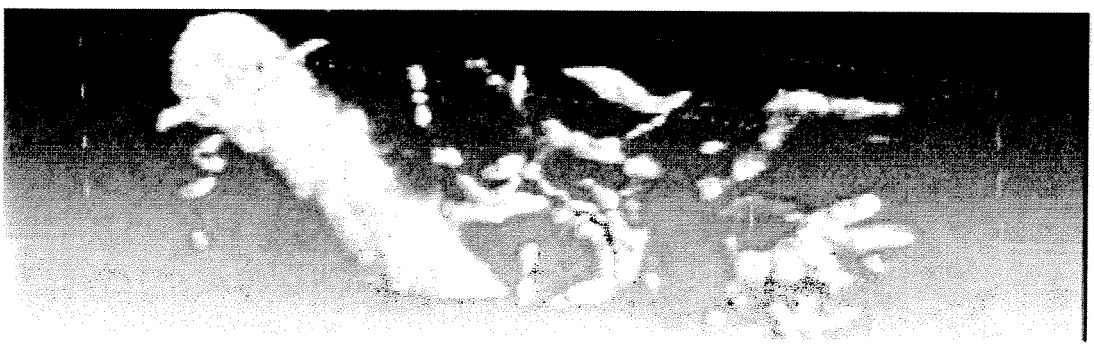

FIGS. 15A and 15B are in vivo fluorescence images with miniature dual-axes confocal microscope. FIG. 15A illustrates a horizontal cross-section of vasculature in an intact ear of an anesthetized mouse, scale bar 50 µm. FIG. 15B illustrates 3D volumetric image of ear vasculature generated from a Z-stack of horizontal cross-sections collected from Z=0 to 150 µm in 3 µm intervals.

Figure 16A:
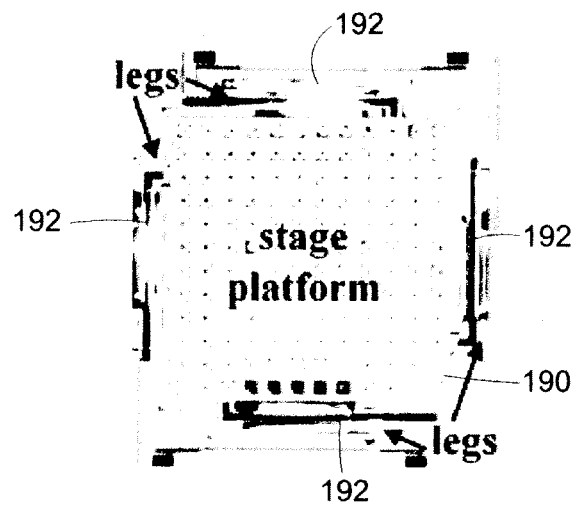
Figure 16B:
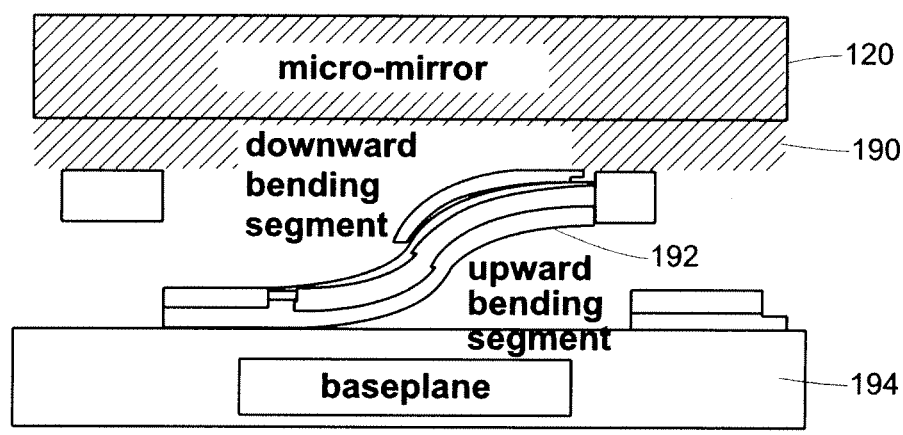
Figure 16C:
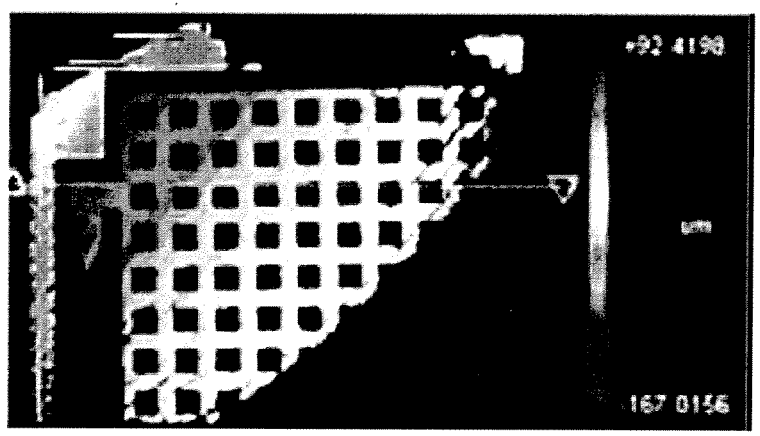

FIGS. 16A-16C illustrate an example vertical scanning (Z-axis) stage for a dual-axes probe device. FIG. 16A illustrates a stage platform actuated by four thin-film PZT folding legs. FIG. 16B is a side view of prototype showing actuation by downward and upward folding segments. FIG. 16C illustrates an optical profilometry measurements of a stage displacement at 20 V shows vertical displacement of 120 µm.

Figure 17A:
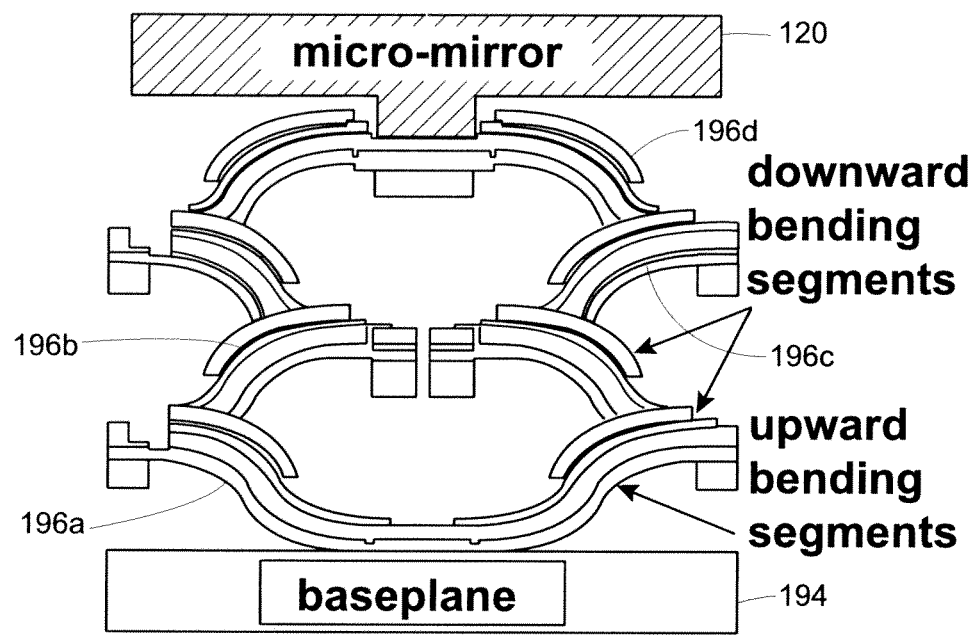
Figure 17B:
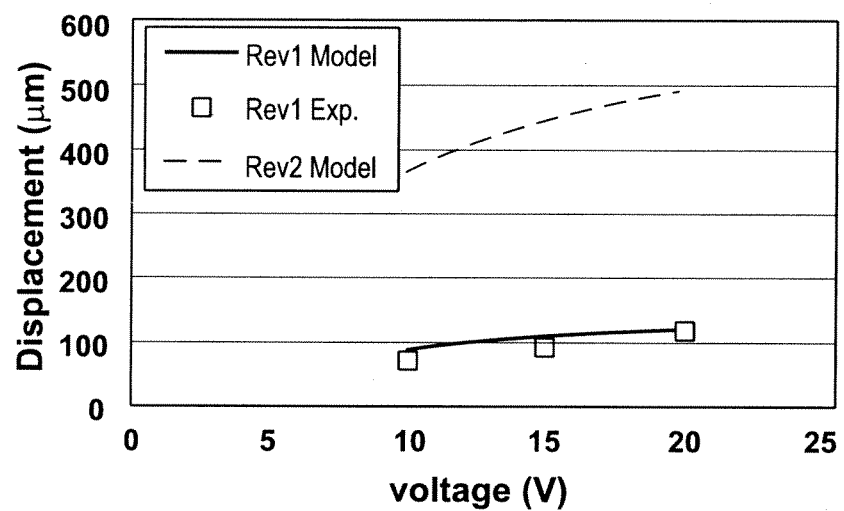

FIGS. 17A and 17B illustrate an example z-axis vertical scanning stage of a dual-axes probe device. FIG. 17A illustrates a schematic (side view) that shows two sets of two sets of folded thin-film PZT folding legs stacked in series. Performance of Z-stage with four sets of folding legs expected to meet displacement specification.

Figure 18:
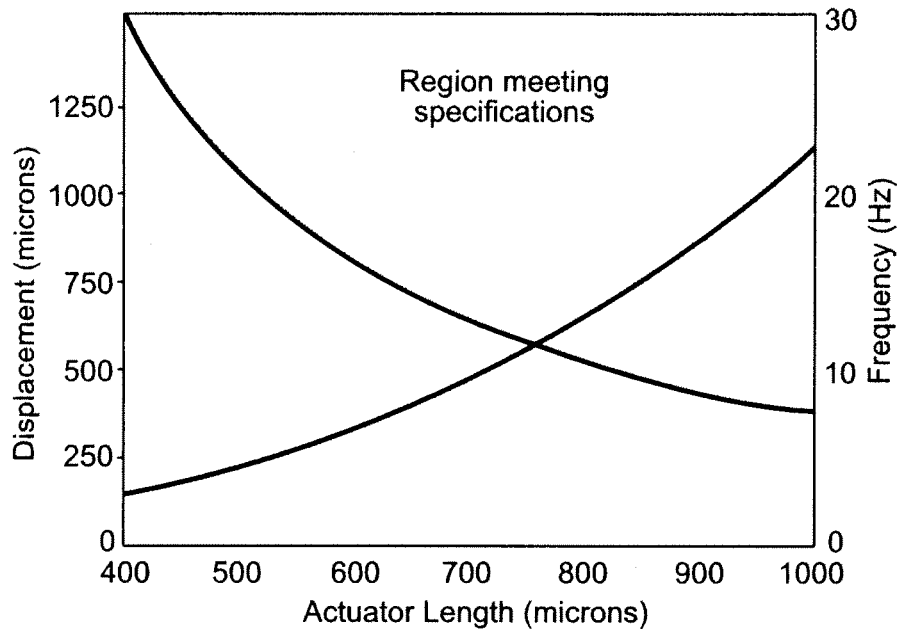
Figure 19A:
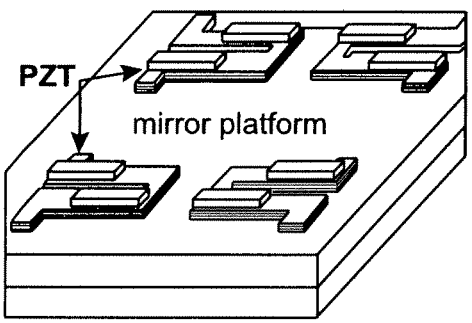
Figure 19B:
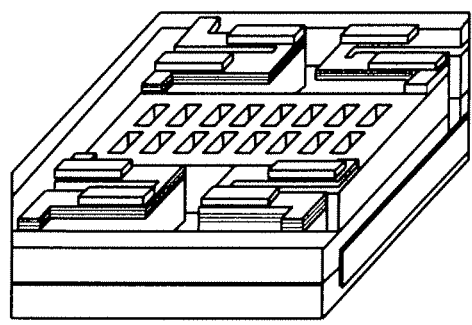
Figure 19C:
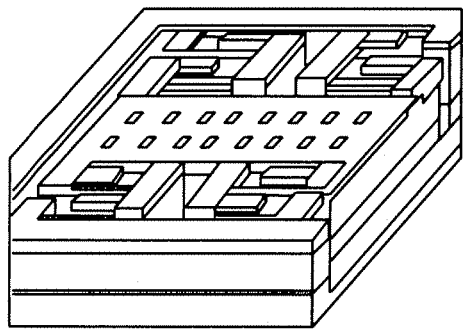
Figure 19D:
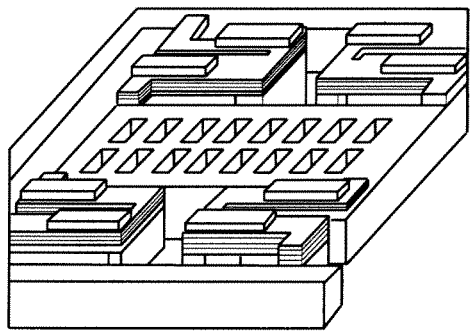

FIG. 18 illustrates a vertical scanning stage performance and process flow, showing the relationship between the Z-axis displacement and natural frequency versus length of a single actuator in a four leg, two fold configuration is shown. A large region exists that meets the performance specifications for in vivo imaging, and providing flexibility for device fabrication.

FIG. 19 illustrates process flow for fabrication of a Z-axis actuator as used in the vertical scanning stage of FIG. 18; 1) Thin-film PZT stacks are deposited onto SOI wafer. 2) Deep-trench etching defines static actuator structures. 3) Photoresist is added to protect components. 4) Etch holes allow for release of Z-stage.

Figure 20A:
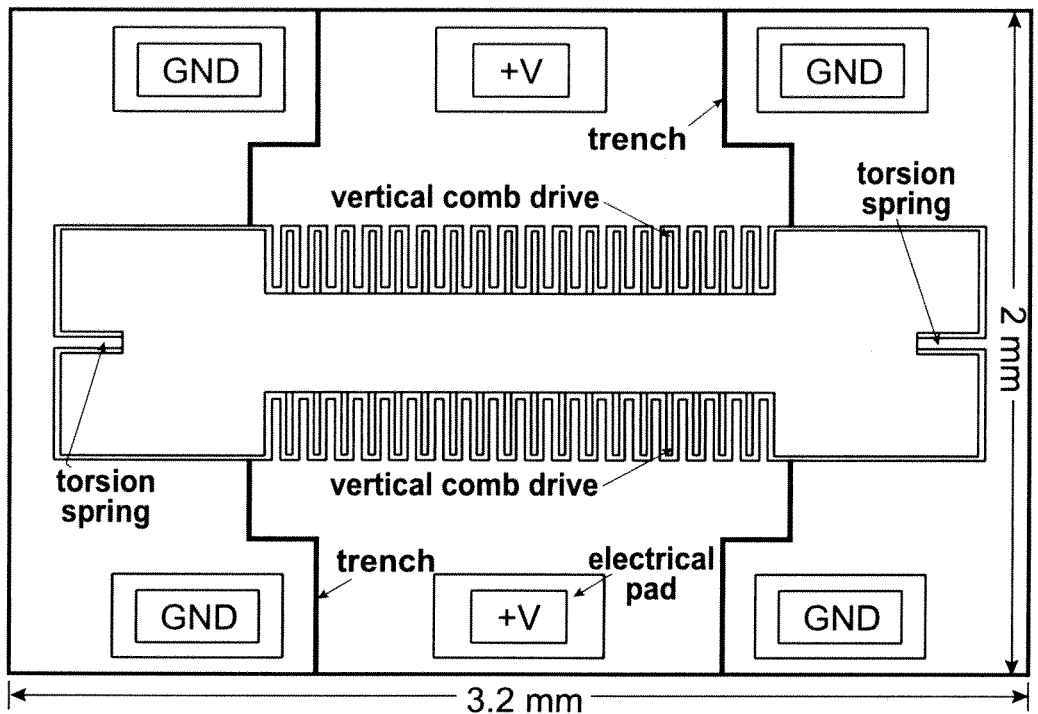
Figure 20B:
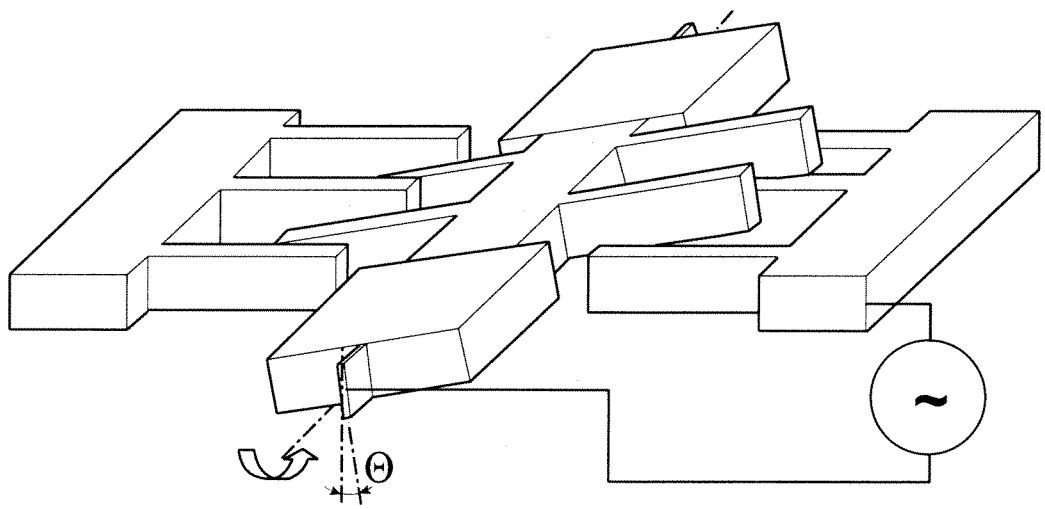

FIGS. 20A and 20B illustrate a one-dimensional scanning micro-mirror. FIG. 20A is a top view schematic of MEMS scanner showing small device footprint (2.0×3.2 m$^2$). FIG. 20B is a perspective view of a parametric resonator in operation. The asymmetry between the electric fields generated by the biased comb electrodes initiates the oscillational motion of the scanner plane at its initial rest position. The mirror plane is driven by the non-linear driving torque that varies with time and rotational angle.

Figure 21A:
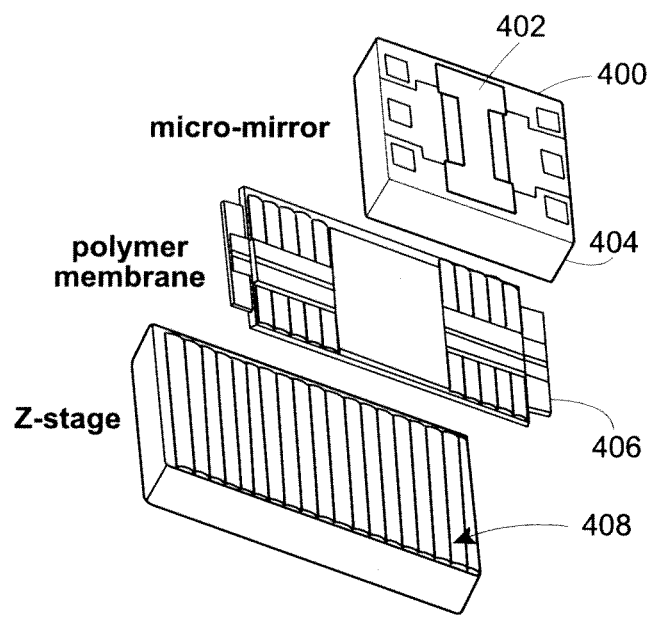
Figure 21B:
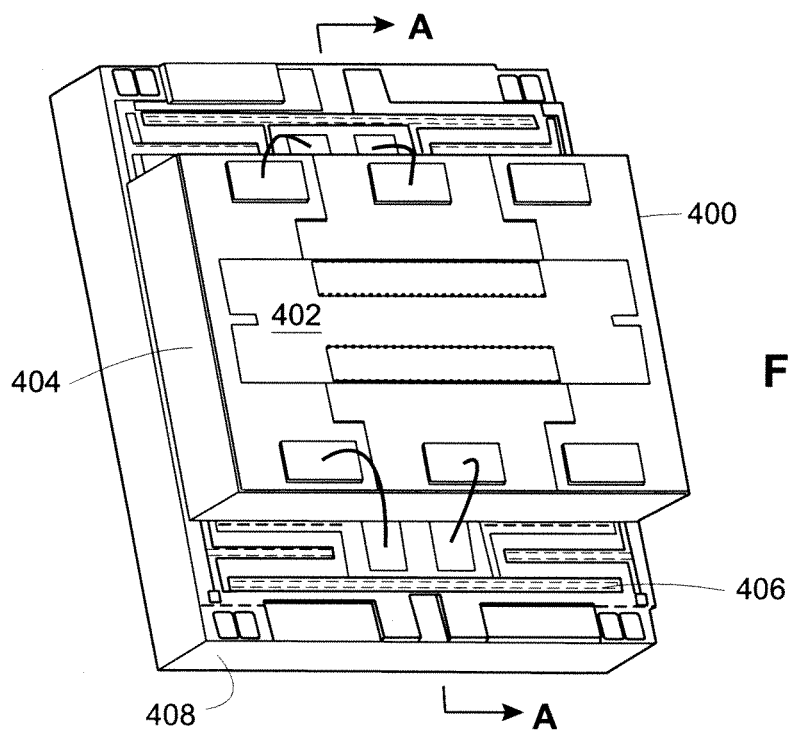
Figure 21C:
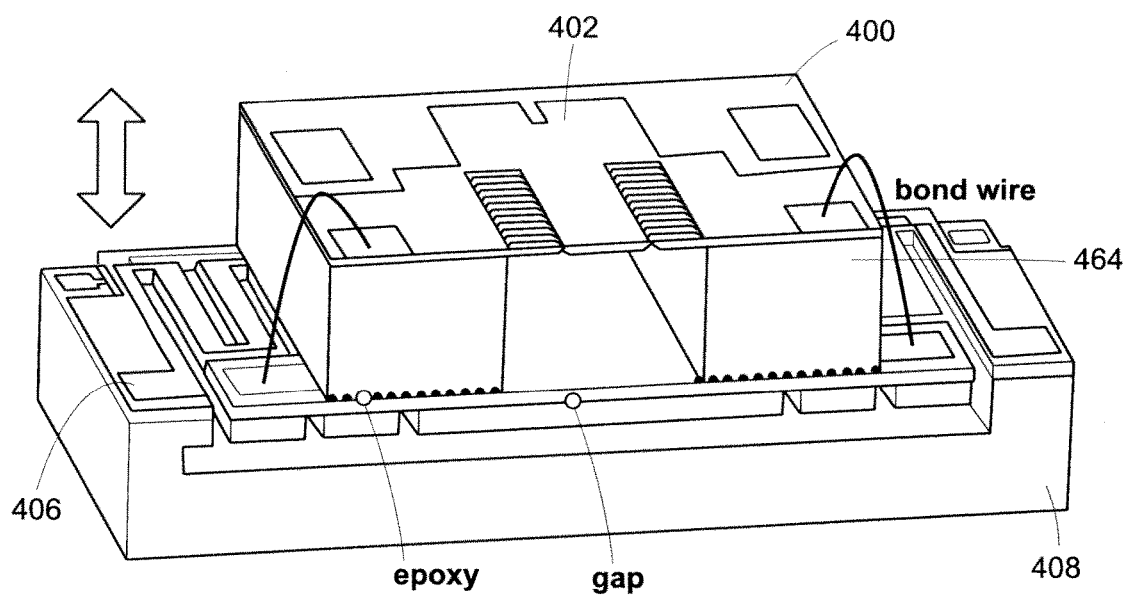

FIGS. 21A-21C illustrate system integration of a micro-mirror and a vertical scanning stage (such as a Z-axis stage). FIG. 21A is an exploded view showing use of a polymer membrane to protect folding legs on Z-stage. FIG. 21B is a 3D view showing wire bonding to micro-mirror. FIG. 21C is a cross-sectional view of integrated vertical cross-sectional scanner.

Figures 22A, 22B:
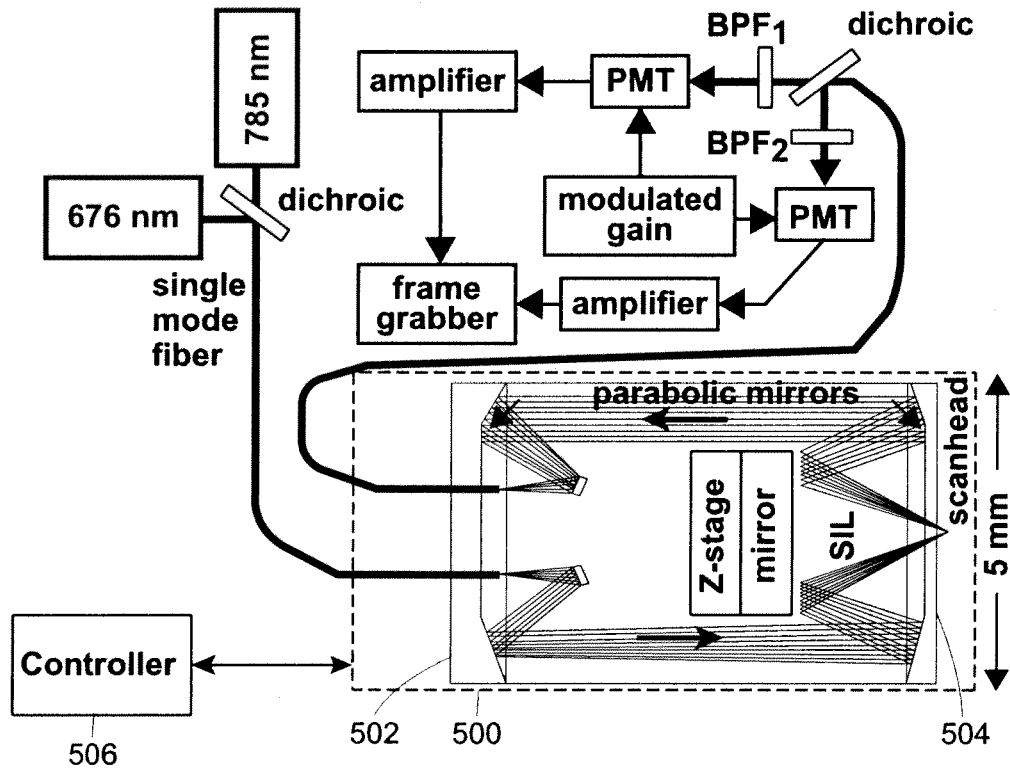
Figure 22C:
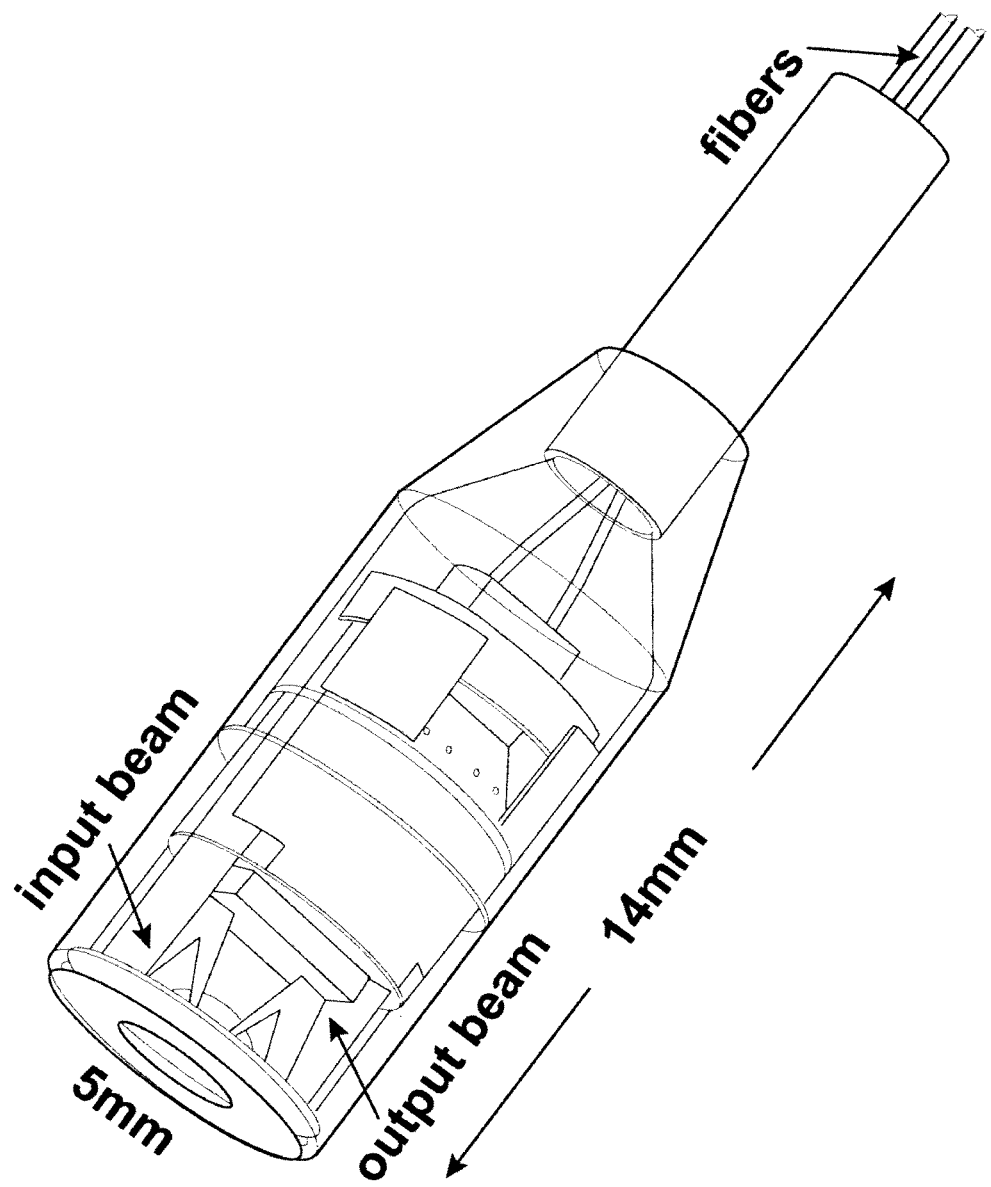

FIGS. 22A-22C illustrate an example implementation of a multi-color dual-axes scanhead, which FIG. 22A illustrates a dual-axes confocal fluorescence microscope that provides excitation at 676 and 785 nm; FIG. 22B is a table listing of an image resolution for miniature dual-axes prototypes is expected to be <5 µm at both wavelengths, sufficient for observing sub-cellular biological phenomena; and FIG. 22C is a perspective view of another illustration of the integrated dual-axes scanhead.

Figure 23A:
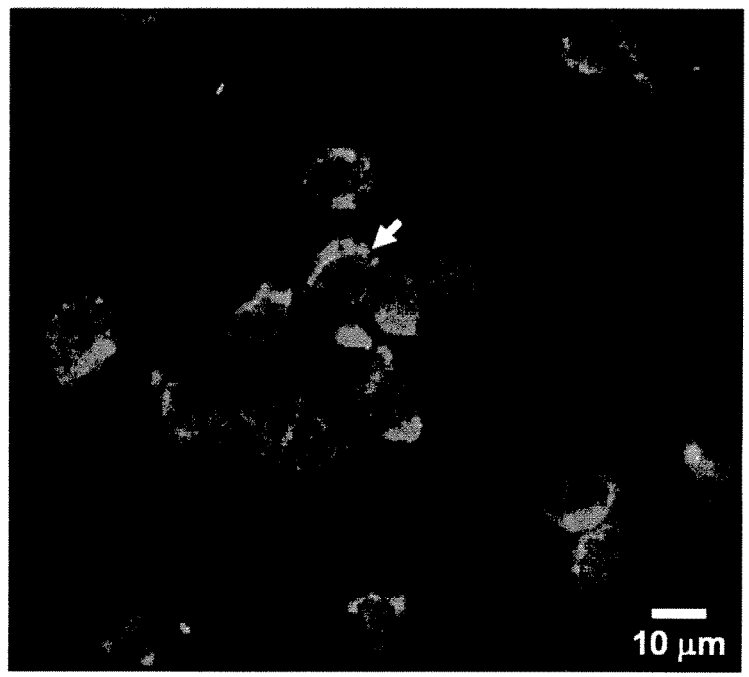
Figure 23B:
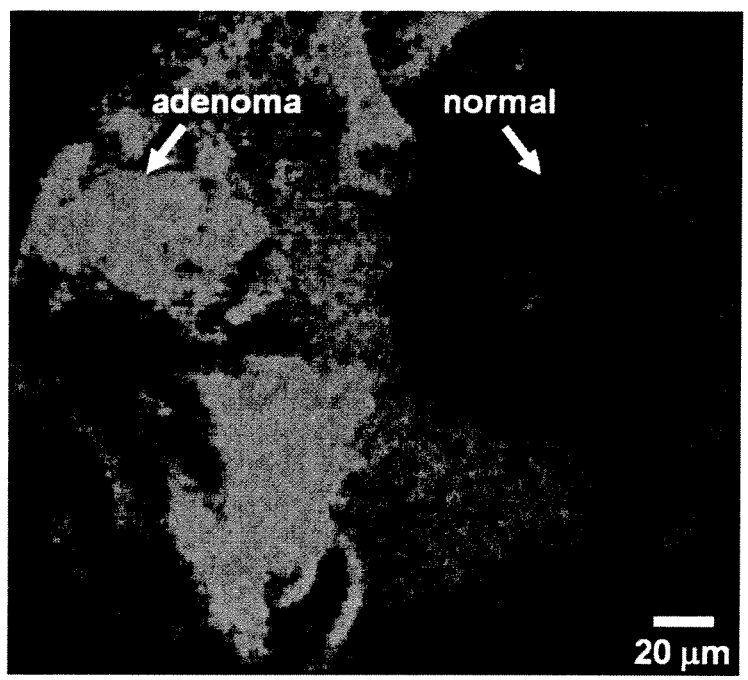

FIG. 23A-23B are images of preferential binding of peptides to cells in culture and in vivo. FIG. 23A illustrates preferential binding of peptides identified using a phage display library that is biopanned against cultured cells and excised tissues. FIG. 23B illustrates selective binding to human colonic adenoma in vivo at 50 µm depth with a confocal miniprobe and shows an adenoma:normal contrast ratio of 20.

Figure 24:
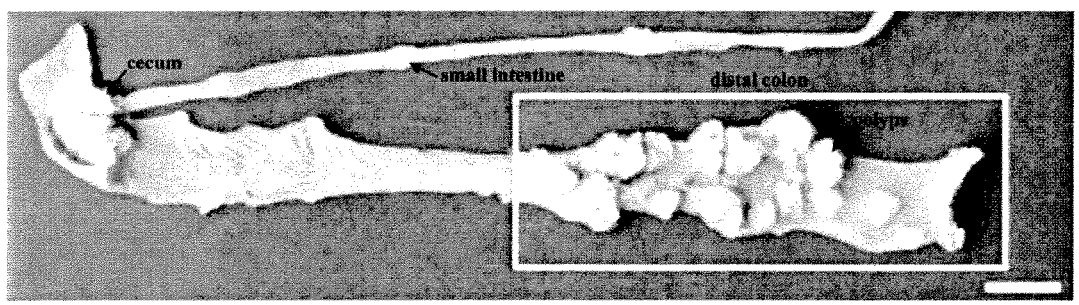

FIG. 24 illustrates that the CPC;APC mouse model of colon cancer develops APC mutations under regulation by Cre recombinase, resulting in the development of polyps in the distal colon and rectum (box), scale bar 10 mm.

Figure 25:
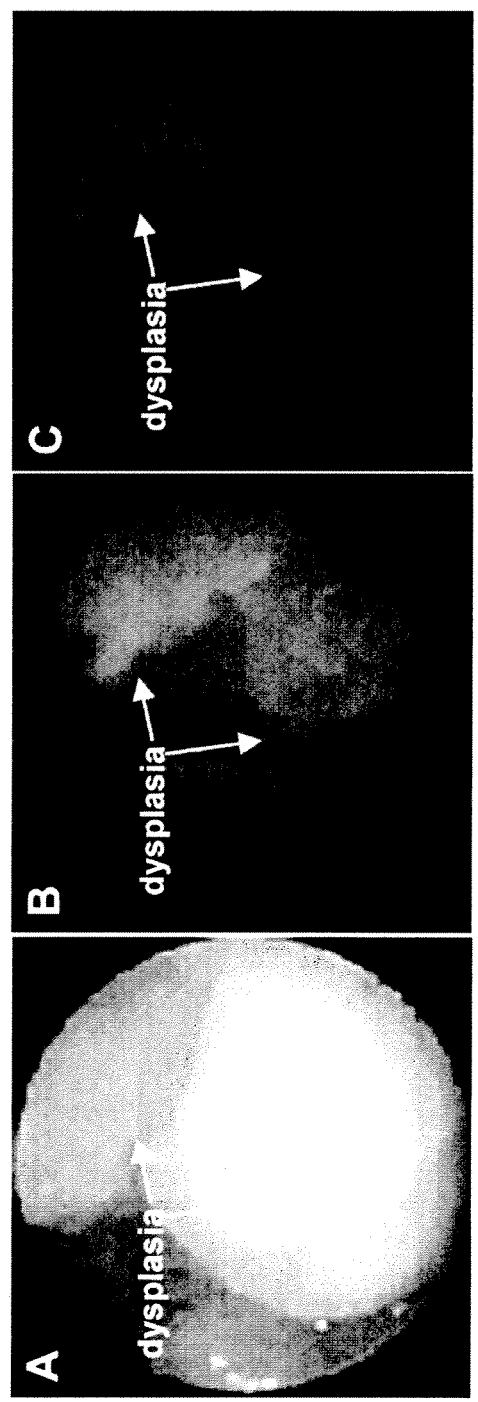

FIG. 25A-25C are images of a mouse model of colonic neoplasia. FIG. 25A illustrates white light endoscopy showing several spontaneous dysplastic polyps in the rectum. FIG. 25B illustrates a fluorescence image with topically applied FITC-labeled targeted peptide "VRPMPLQ" demonstrating affinity binding. FIG. 25C illustrates a fluorescence image from scrambled (control) peptide "QLMRPPV" revealing reduced binding.

Figure 26:
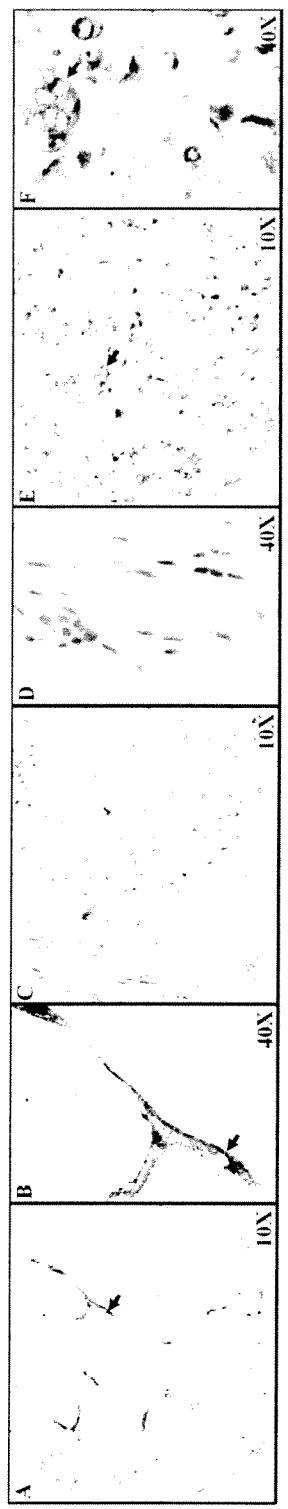

FIG. 26A-26F are images of CXCR7 expression in breast cancer on immunohistochemistry using mouse monoclonal antibody 11G8. FIG. 26A illustrates invasive ductal carcinoma revealing CXCR7 expression in vasculature (arrow), 10×. FIG. 26B illustrates Endothelial staining of a blood vessel (arrow) from A), 40×. FIG. 26C illustrates normal breast tissue showing no CXCR7 expression, 10×. FIG. 26D illustrates CXCR7 negative blood vessel from C), 40×. FIG. 26E illustrates human invasive ductal carcinoma with tumor cells (arrow) strongly positive for CXCR7, 10×. FIG. 26F illustrates detail of tumor cells (arrow) from E), 40×.

Figure 27:
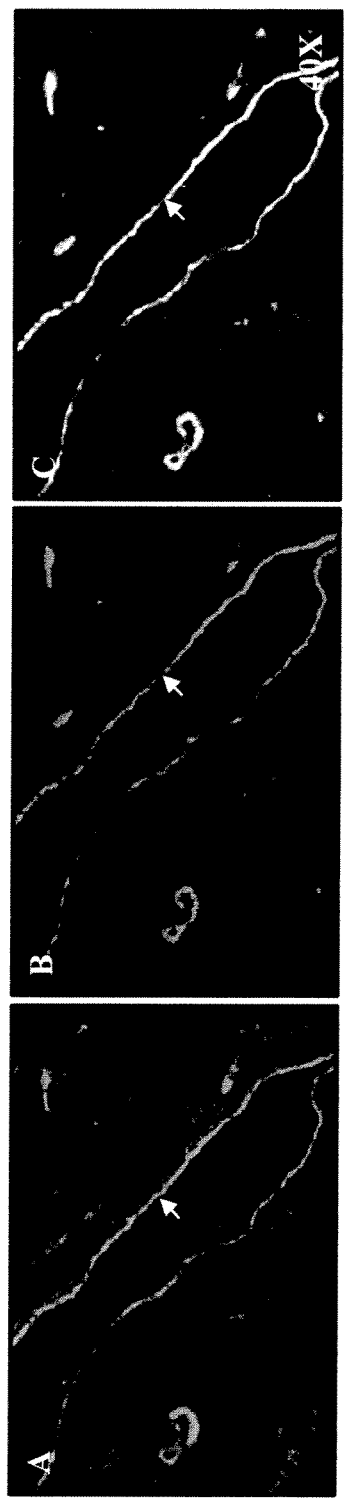

FIG. 27A-FIG. 27C illustrates that the expression of CXCR7 is co-localized with the endothelial marker CD31 in tumor-associated blood vessels. FIG. 27A illustrates CXCR7 expression from a section of orthotopically implanted human breast tumor cells in a mouse revealing expression by breast cancer vasculature (arrow), magnification 40×. FIG. 27B illustrates endothelial marker CD31 outlining endothelium (arrow) surrounding lumen of blood vessels, FIG. 27C illustrates the overlay of two images showing co-localization of CXCR7 expression in vascular endothelium (arrow).

Figure 28:
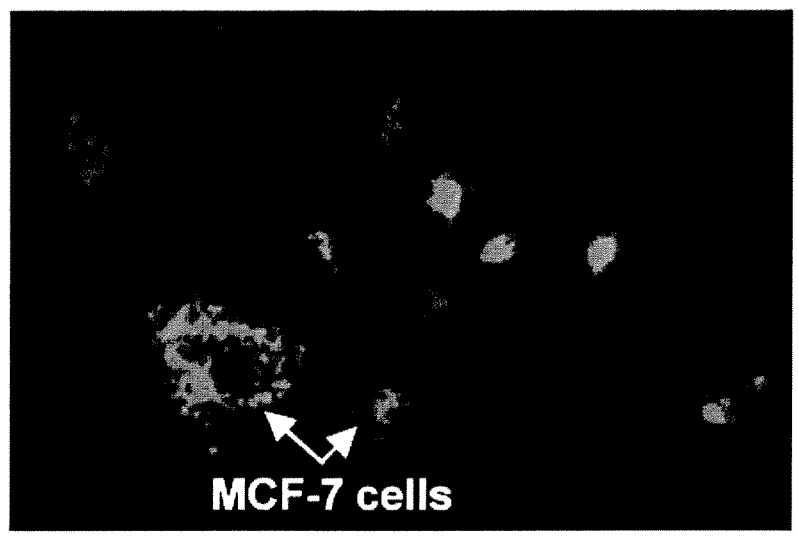

FIG. 28 illustrates CXCR7-mediated uptake of CXCL12-mCherry in MCF-7 human breast cancer cells.

Figures 29A, 29B, 29C, 29D:
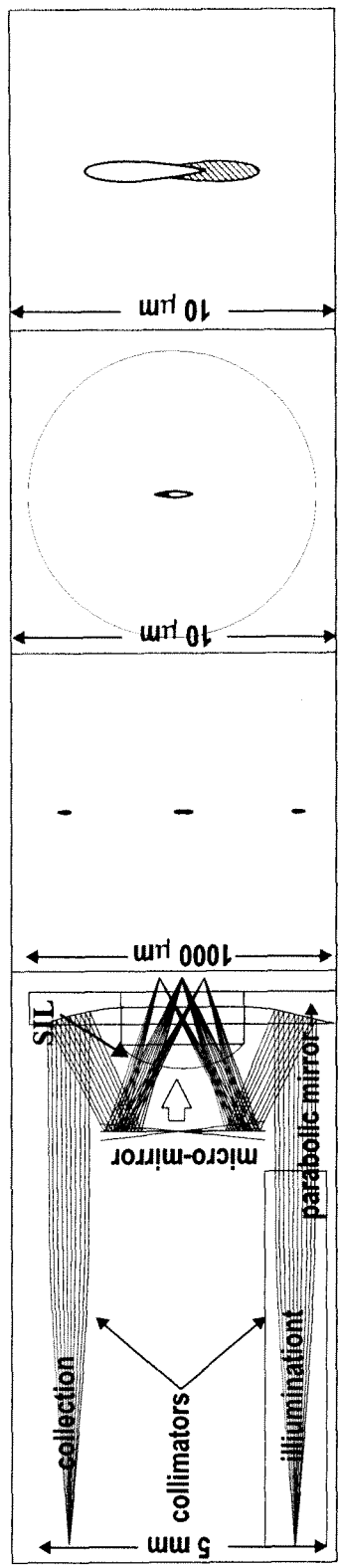

FIGS. 29A-29D illustrate a model of the light path by the illumination and collection beams in a miniature dual-axes probe device. FIG. 29A illustrates a diagram of the model showing deflection of the micro-mirror for lateral scanning and translation of the micro-mirror for vertical scanning. FIG. 29B illustrates a scan angle along a lateral direction. FIGS. 29C and 29D illustrate spot diagrams with and without an solid emersion lens (SIL) for focusing.

While the disclosed methods and apparatus are susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF PREFERRED EMBODIMENTS

Before describing the details of vertical-axis control for the present imaging probe techniques, we illustrate that a dual-axes architecture comprised of an off-axis light illumination and collection, combined with use of low numerical aperture objectives results in a superior dynamic range compared to that of the single axis configured used in conventional confocal and two photon microscopes. This improvement results in the ability to collect fluorescence images in vertical cross-sections to visualize the perpendicular epithelial differentiation patterns. Below this discussion, we demonstrate the design, development, and fabrication of a two-dimensional scanning micro-mirror using MEMS technology. Furthermore, the design may be packaged in a 5 mm diameter scanhead for a probe using a replicated parabolic focusing element in a zig-zag geometry. The application further demonstrates the design, development and fabrication of a vertical scanning thin film piezoelectric (PZT) actuator. These materials have the mechanical properties to meet the speed and displacement requirements for performing what we call axial, vertical (Z-axis), or longitudinal scanning.

Generally, what are described are examples of dual-axes architecture configurations in which off-axis illumination and collection of light is achieved within a sample using low numerical aperture objectives that provide high dynamic range due to the elimination of collection of scattered nose signals. The unique geometry allows for the collection of fluorescence images in vertical cross-sections (perpendicular to tissue surface), an orientation that provides a comprehensive view of the normal tissue differentiation patterns of the epithelium, the origin of cancer in the colon and breast.

While the imaging devices described herein may be used for any number of applications, in particular, some applications involve the ability to select affinity peptides using the technique of phage display to detect over expressed cell surface targets. From this, a CPC;APC mouse model of colon cancer was developed where Cre-regulated expression of APC generates pre-malignant lesions (dysplasia) in the epithelium of the distal colon and rectum, which can be accessed by a miniature intra-vital microscope. Furthermore, using these techniques we have been able to show that the vasculature of breast tumor tissue over expresses the chemokine receptor CXCR7, a novel marker of angiogenesis. Molecular probes, such as peptides, may then be developed to affinity bind to this target using cystine-knot peptides (knottins) as the scaffold for development.

Figure 6A:
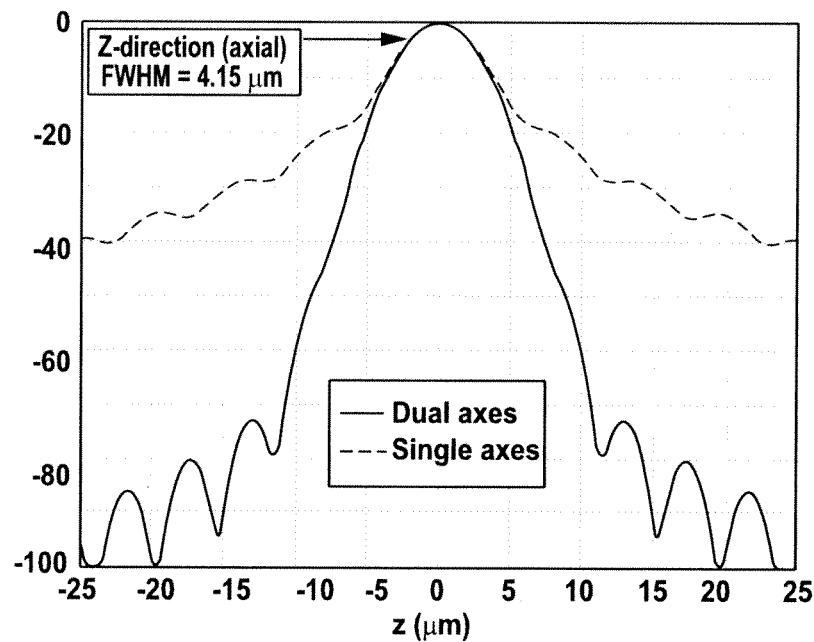

The improvement in dynamic range in a non-scattering media (over single-axis techniques) can be quantified using diffraction theory with paraxial approximations. Gaussian illumination is used to model the incident light delivered by an optical fiber. The signal at the detector from a point source reflector as its distance below the surface of the tissue is varied may be solved numerically in Matlab. The following parameters for the dual-axes configuration are used: $\alpha=0.21$ radians, $\theta=30$ degrees, $\lambda=1.3$ µm and $n=1.4$ for tissue. The results of diffraction theory reveals a result of $\Delta x_d=2.4$ µm, $\Delta y_d=2.1$ µm, and $\Delta z_d=4.2$ µm for the transverse and axial resolutions defined by the full-width-half-max (FWHM), respectively. In order to achieve the same axial resolution (FWHM) in the single axis configuration, $\alpha=0.58$ radians is needed. The calculated axial response for the single axis design with Gaussian illumination is shown by the dashed line in FIG. 6A. This result reveals that the main lobe falls off in the axial (z-axis) direction as $1/z^2$. In comparison, the response for the dual-axes configuration, shown by the solid line, and reveals that the main lobe rolls off in the axial direction as $\exp(-kz^2)$. Thus, the dual-axes confocal architecture results in a significant improvement in dynamic range and in an exponential rejection of out-of-focus scattered light in comparison to that for single axis.

The superior dynamic range of detection for dual axes in comparison to that of single axis has been further evaluated using a tissue scattering (turbid) model. Calculations performed to analyze these effects are based on Monte Carlo simulations using a non-sequential ray tracing program (ASAP® 2006 Breault Research Organization, Tucson, Ariz.). The following parameters for the dual-axes configuration are used: NA=0.21 radians, $\theta=30$ degrees, $\lambda=633$ nm and $n=1.4$ for tissue, resulting in a transverse and axial resolution of $\Delta x_d=1.2$ µm, $\Delta y_d=1.0$ µm, and $\Delta z_d=2.0$ µm, respectively. In order to achieve the same axial resolution (FWHM) in the single axis configuration, NA=0.58 is needed. Three assumptions are made in this simulation study: 1) multiple scattering of an incoherent beam dominates over diffraction effects, 2) the non-scattering optical medium surrounding the lenses and the tissue (the scattering medium) is index matched to eliminate aberrations, and 3) absorption is not included to simplify this model and because there is much larger attenuation due to the scattering of ballistic photons. This analysis quantifies the axial response at the detector for the single and dual-axes optical configurations using parameters that produce the same axial resolution (FWHM) by calculating the photon flux f(Δz) as the mirror is displaced along the z-axis below the tissue surface. The model uses Mie theory with the Henyey-Greenstein phase function p(θ) to model the angular dependence of tissue scattering. The flux is calculated with the mirror at positioned in the range −10 μm<Δz<10 μm with respect to the focal plane at z=0, which is located at 200 μm below the tissue surface. The flux is then normalized according to F(Δz)=f(Δz)/f(0).

Figure 6B:
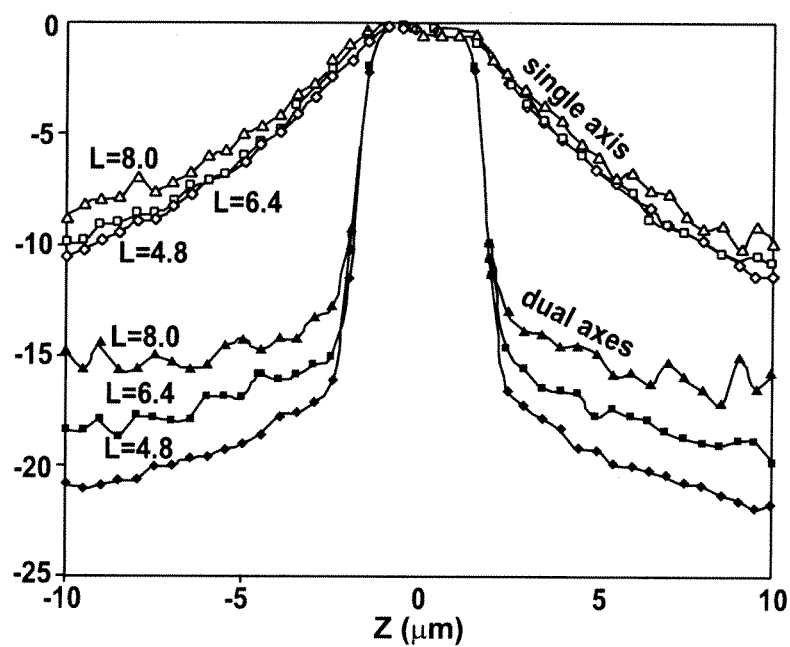

We have also evaluated the axial response of the single and dual-axes confocal architectures for various optical path lengths in a scattering (turbid) media. The total optical length L is defined as twice the product of the scattering coefficient $\mu_s$ and the tissue depth t, or $L=2\mu_s t$. The factor of two originates from the fact that the total path length is twice the tissue depth. The axial response is shown in FIG. 6B for various optical path lengths L, including 4.8, 6.4, and 8.0. Note that for each optical length L, the dual-axes configuration has significantly better dynamic range than that of single axis. These values of L are typical parameters of gastrointestinal epithelium. At λ=633 nm, $\mu_s$ is about 7 mm$^{-1}$ for esophagus tissue and about 20 mm$^{-1}$ for normal colon mucosa. The range of tissue depths spanned by L=4.8 to 8 for esophagus and colon is 340 μm to 570 μm and 120 μm to 200 μm, respectively. In addition, these results shows that for the single axis configuration the dynamic range does not exceed 10 dB over a factor of ~2 difference in optical thickness L, suggesting that use of this geometry is limited to horizontal cross-sectional imaging. On the other hand, for the dual-axes architecture there is a significant improvement in dynamic ranger over that of single axis for this entire range of optical thicknesses. Furthermore, scattering does not appear to alter the FWHM of the axial response for either single or dual axes over this range of lengths.

Figure 7A:
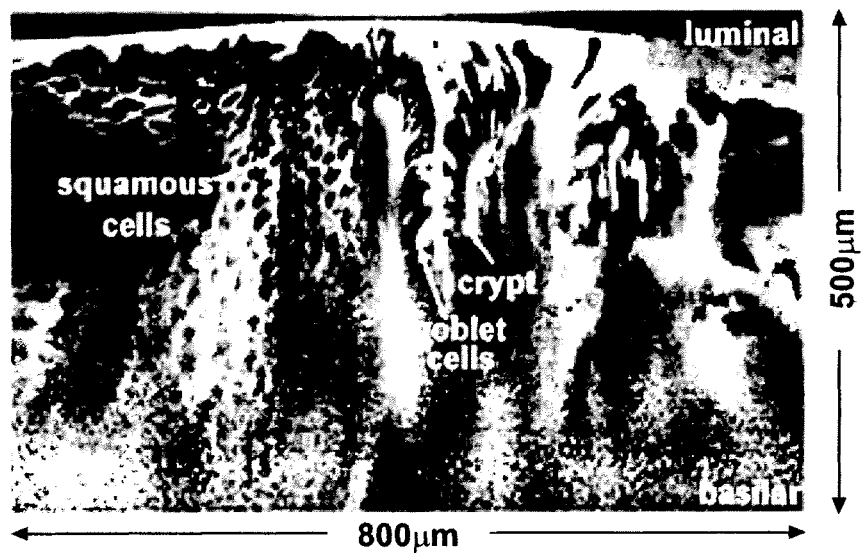
Figure 7B:
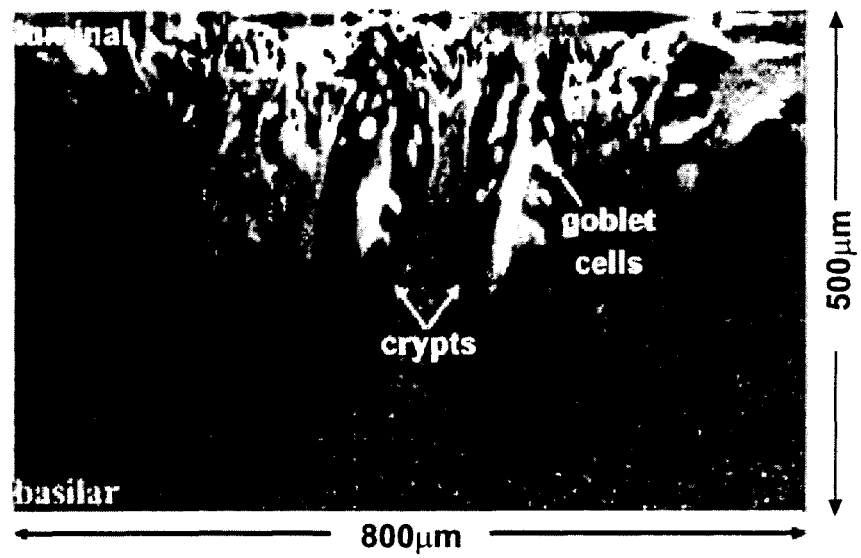
Figure 8A:
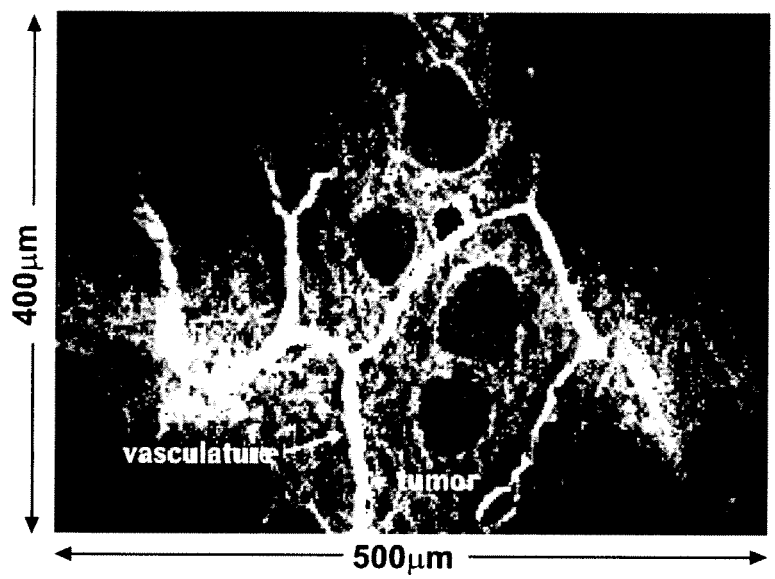
Figure 8B:

In FIG. 7, vertical cross-sectional fluorescence images of A) esophagus and B) colon collected with a tabletop dual-axes confocal microscope are shown. These specimens were incubated with a near-infrared dye (IRDye® 800CW, LI-COR Biosciences) prior to imaging after being freshly excised during endoscopy. These images were collected at 2 frames per second with a transverse and axial and resolution of 2 and 3 μm, respectively. With use of post-objective scanning, a very large field-of-view of 800 μm wide by 500 μm deep was achieved. In FIG. 8A, the specimen was collected from the squamo-columnar junction of a patient with Barrett's esophagus. Over the left half of the image, the individual squamous cells from normal esophageal mucosa can be seen in the luminal to the basilar direction down a depth of 500 μm. Over the right half of the image, vertically oriented crypts with individual mucin-secreting goblet cells associated with intestinal metaplasia can be appreciated as brightly stained vacuoles. This diseased condition is associated with greater than 100 fold relative risk of developing cancer. In FIG. 8B, the specimen was collected from a flat colonic adenoma, and the image reveals vertically oriented dysplastic crypts with individual goblet cells.

Three-dimensional (3D) volumetric images have been constructed from a series of horizontal cross-sectional fluorescence images collected in vivo to demonstrate the optical sectioning capability of the dual-axes confocal architecture. A xenograft mouse model of glioblastoma multiforme (GBM) was used for this demonstration. Approximately 10$^7$ human U87MG glioblastoma cells diluted in 100 μl of phosphate-buffered saline (PBS) were implanted subcutaneously in the flank of a nude mouse, and imaged in vivo when the tumors reached about 1 cm in size (~21 to 30 days after implantation). Indocyanine green (ICG, Sigma-Aldrich, Inc) was used as a non-specific contrast agent by dissolving in distilled water at a concentration of 5 mg/ml and then diluted in 10×PBS. The mice were anesthetized with 3% avertin, and 100 μl of the ICG solution was injected intravenously. The skin overlying the tumor was exposed immediately, and horizontal cross-sectional images were collected with a field-of-view of 400×500 μm$^2$. A fluorescence image collected at 50 μm below the tissue surface is shown in FIG. 8A. A high density of disorganized and tortuous vasculature can be seen infiltrating the tumor. A total of 400 horizontal cross-sections acquired at 1 μm increments were used to generate the 3D volumetric image, shown in FIG. 8B, using volume modeling software (AMIRA).

With various features of the dual-axes configuration now described, and in particular as applicable to vertical cross-section imaging of between 0 to 500 μm depths below a tissue surface, specific example probes for such imaging will be discussed.

Figure 1:
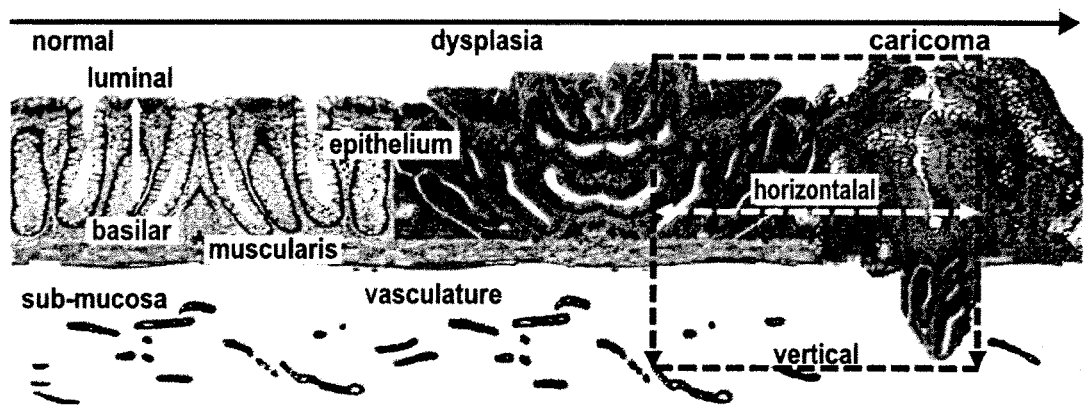
Figure 2:
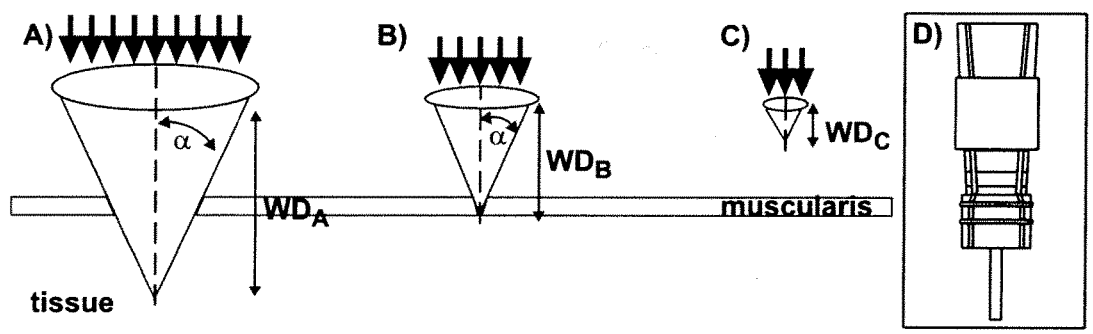
Figure 3A:
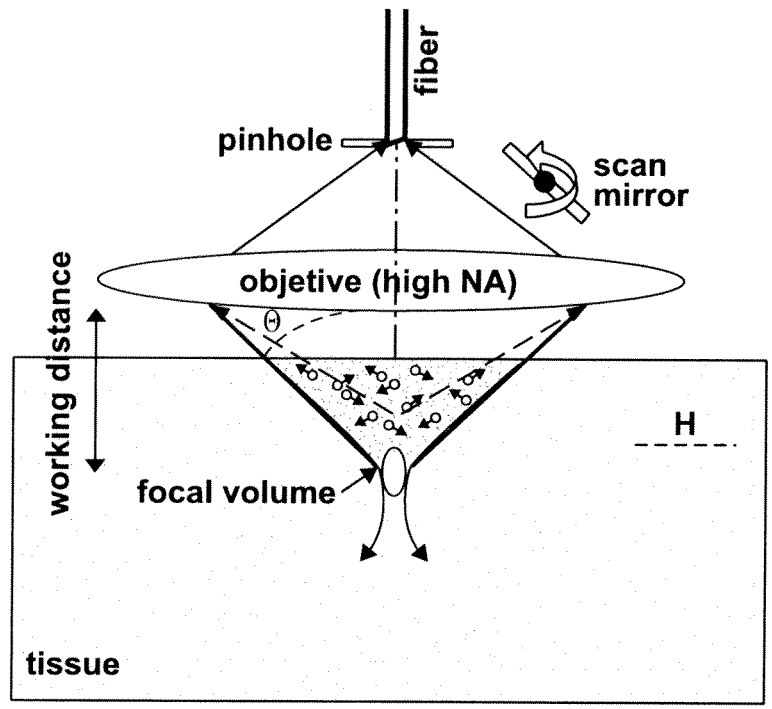
Figure 3B:
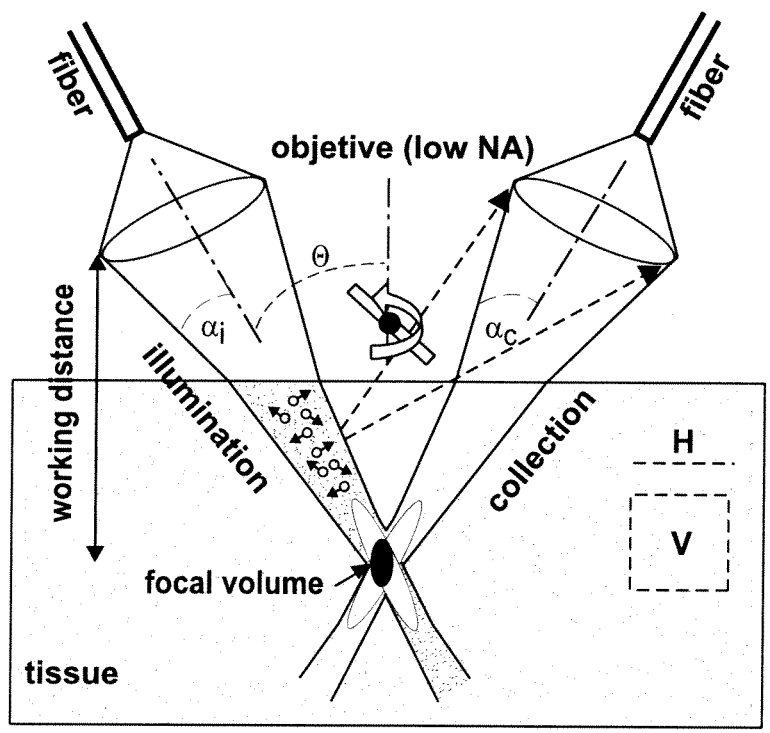
Figure 4A:
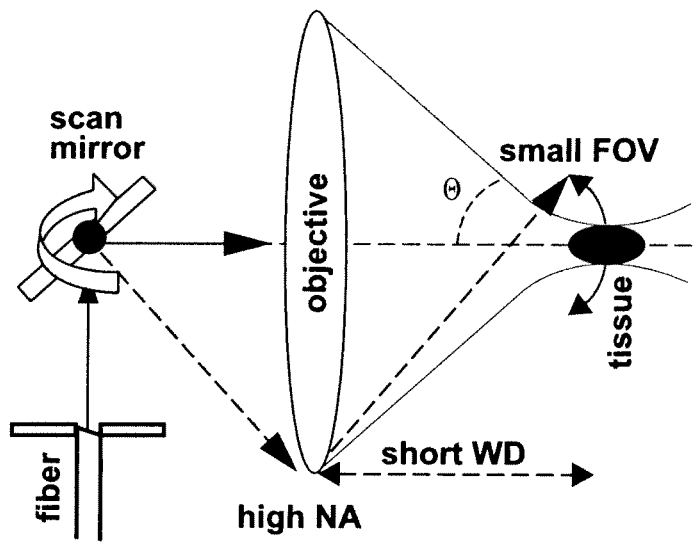
Figure 4B:
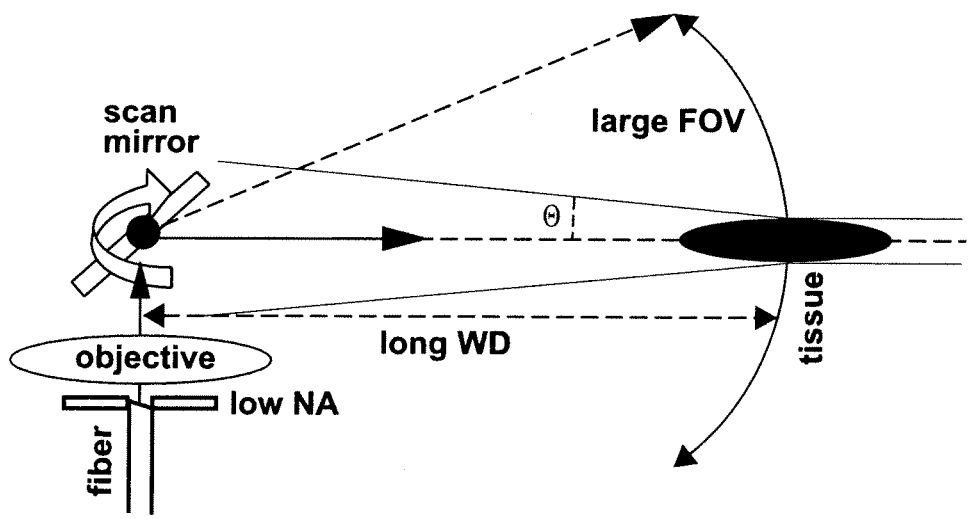
Figure 5A:
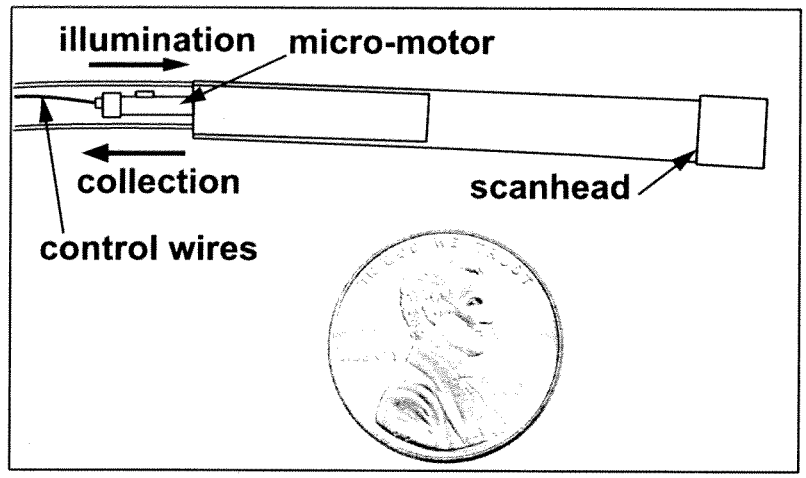
Figure 5B:
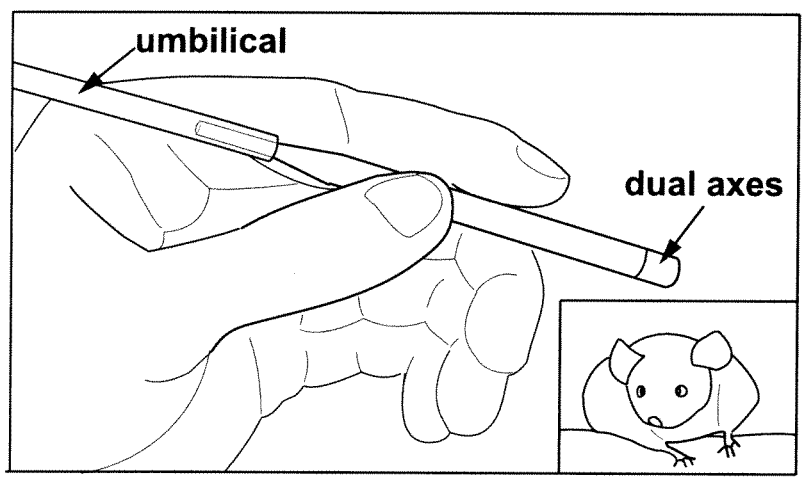
Figure 9A:
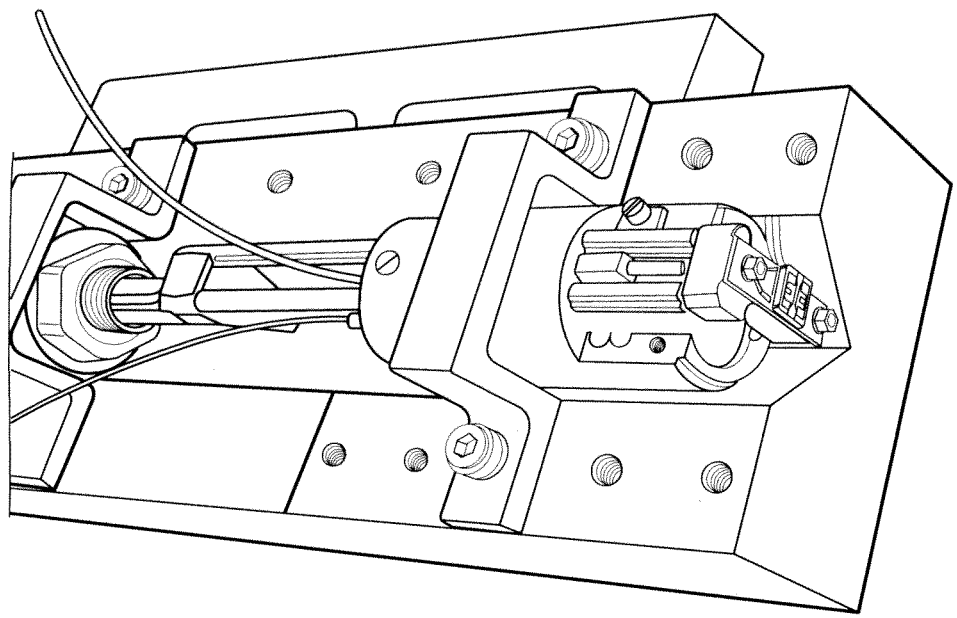
FIGS. 9A-9C illustrate an example implementation of a dual-axes optical probe as may be used in confocal microscopy system.
Figure 9B:
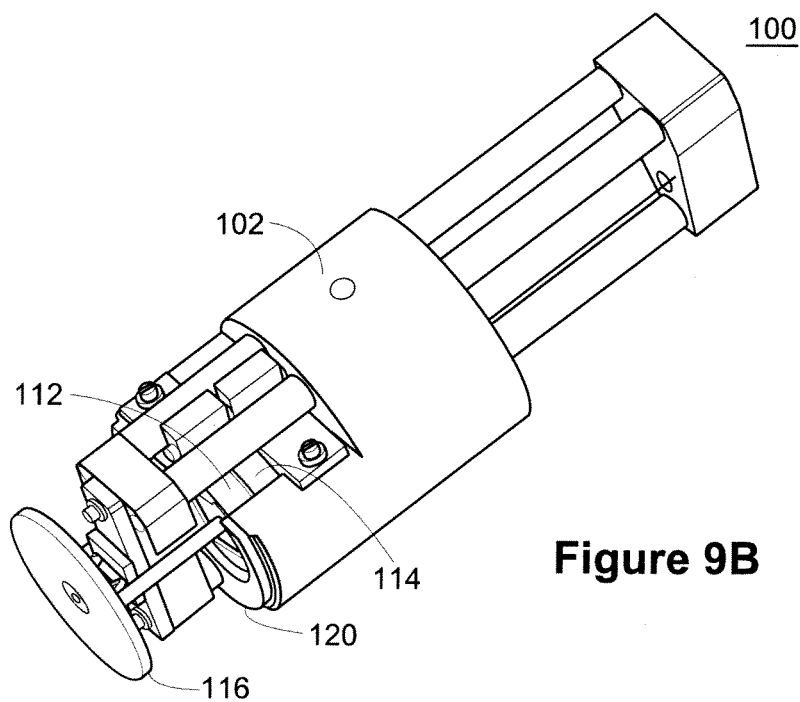
Figure 9C:
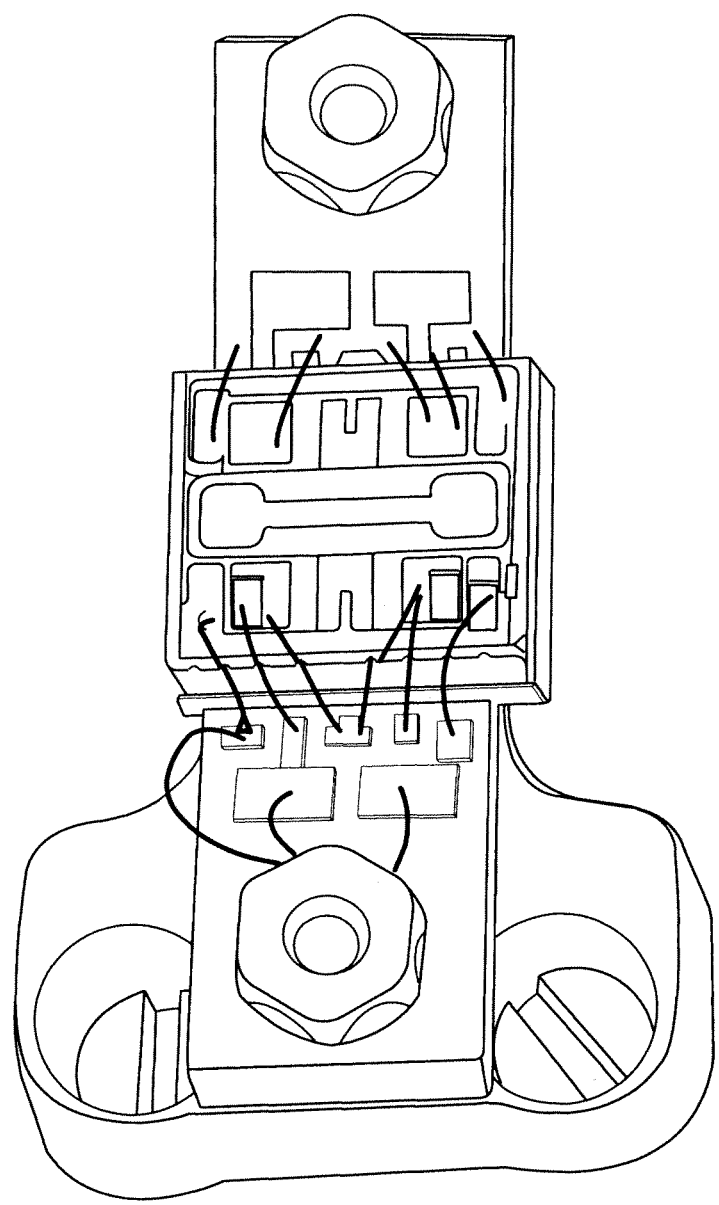

FIGS. 9A-9C and FIG. 10 illustrate two example implementations of dual-axes imaging probes, sized for 10 mm and 5 mm, respectively. FIGS. 9A-9C illustrate a dual-axes probe 100. The probe 100 is characterized both having a horizontal (or transverse) scanning mechanism and an axial (or longitudinal) scanning mechanism. The first scanning mechanism allows for an illumination beam and a collection beam to overlap within a sample at a confocal region of interest (similar to that shown in FIG. 3B). That first scanning mechanism may scan that confocal region across a transverse direction, such as a lateral linear direction (such as the X-direction) or across a lateral transverse plane, such as the XY-plane within a tissue. By using low NA objectives on the illumination beam and on the collection beam, that scanning can be achieved at a substantial depth below the outer surface of the tissue under examination.

The scanning mechanism may be a slider or other mechanism that allows a illumination assembly 102 to move in an vertical direction to achieve scanning along a Z-axis. This Z-axis scanning may be simultaneous to the horizontal scanning to provide for tight control and allow for scanning over a volume of interest.

Systems integration is important to form a miniature dual-axes confocal microscope because of the small size required for accurate and stable placement on the epithelium in live subjects. It is desired to have a package design that allows for precise mounting of the following optical elements: two fiber-coupled collimator lenses, a two-dimensional MEMS micro-mirror, a parabolic focusing mirror, and a hemispherical index-matching solid immersion lens (SIL) element.

In the illustration of FIGS. 9A-9C, the probe 100 includes a housing 102 (partially shown) that includes two beam channels, an example of which is shown in FIG. 11, one beam channel is for the illumination beam into the sample, the other is for a collection beam from the sample. Alignment of the two beam channels parallel to one another can be achieved by having channels 104 and 106 that contain fiber-pigtailed collimators 105a and 105b in a pair of v-grooves 107a and 107b that are precision machined into the housing. An accuracy of 0.05 degrees can be achieved in aligning the two beams parallel to one another using the v-grooves with pre-assembled fiber collimators. The first channel 104 provides the illumination beam, preferably having laser energy (either continuous wave or pulsed) a first wavelength, while the second channel 106 is for a collection beam from the sample. Each channel 104 and 106 comprises a lead optical fiber 108 and 110, respectively, acting as a collimator and having a respective collimated optical beam pass through respective Risley prism assembly 112 and 114. The Risley prisms 112, 114 provide for focusing of the respective beams by axial adjustment of the position of the prisms, which can be controlled by mechanical or motor operation. Thus additional precision in alignment can be attained through the Risley prisms 112 and 113, to provide fine steering of the collimated beams to bring the system into final alignment. These prisms may be angled at 0.1 deg. and can be rotated to steer the collimated beam in an arbitrary direction over a maximum range of ~0.05 deg. In this way, the Risley prisms 112 and 114 can be used to assist in maximizing the overlap of the two collimated beams after they are focused by a parabolic mirror assembly 116 at a distal end 117 of the probe 100. Two prisms are used in each beam so that complete cancellation of the deflection by each can be achieved, if needed, to provide maximum flexibility.

FIG. 12 illustrates a larger view of the parabolic mirror assembly 116 showing two collimated beams, one the illumination beam to the sample and the other collection beam from the sample. What are illustrated then may be considered two beam paths, which are made to overlap in the sample create the dual-axes architecture. Two collimated beams, one for each channel 104 and 106 are focused at an inclination angle θ to the Z-axis by a parabolic mirror 116 with a maximum cone half-angle α to a common point in the tissue after being deflected by a two-dimensional micromirror. In this example, the illumination beam impinges upon a parabolic reflector base element 118 that focuses the beam into the sample. Correspondingly, the parabolic mirror assembly 116 takes the dispersive collection beam and collimates it into its respective fiber. Specifically, the mirror 116 operates in conjunction with a scanning mirror 120 that is part of the horizontal scanning control mechanism. The illumination and collimated beams reflect off of different mirror elements 120a and 120b and are focused through a solid immersion lens (SIL) element 122 in a central opening of the base element 118 and onto the sample of interest.

The mirror 120 is preferably a micro-mirror, that is, having features on in the several micron size and capable of miniature deflections over the micron range. Movement of the mirror 120 controls scanning of the two beams along a horizontal (XY) plane within the tissue, under the control of a MEMS chip 124 in the probe, as shown in FIG. 13. During operation, the flat side of the SIL 122 is placed against the tissue surface to couple the incident beams with minimal aberrations. The parabolic mirror 116 may be fabricated using a molding process that provides a surface profile and smoothness needed for diffraction-limited focusing of the collimated beams. Once the collimated illumination beam path and the collection beam path are aligned parallel to each other, the parabolic mirror 116 then provides a "self-aligning" property in this optical system, which forces the focused beams to intersect at a common focal point within the tissue. Focusing is performed primarily by the parabolic mirror which is a non-refractive low NA optical element, for example that produces beams with an NA of 0.12. This feature allows for light over a broad color regime to become focused to the same point below the tissue surface simultaneously, allowing for multi-color confocal imaging to be performed, for example, where the illumination beam comprises laser energy at two or more wavelengths. The MEMS chip 124 also provides vertical scanning, by deflecting the micro-mirror 120 along an vertical (Z-axis) direction, for example, to allow for vertical cross-sectional imaging. By using a MEMS fabricated chip for lateral and vertical scanning a fast scan rate has been achieved allowing for real time scanning over a volume of interest within a sample.

In the illustrated example, the parabolic mirror element 116 is 10 mm in diameter and the package around the lens assembly 102 is about 12.7 mm in diameter. FIG. 9C is a photograph of a mounted MEMS chip 124.

Figure 10:
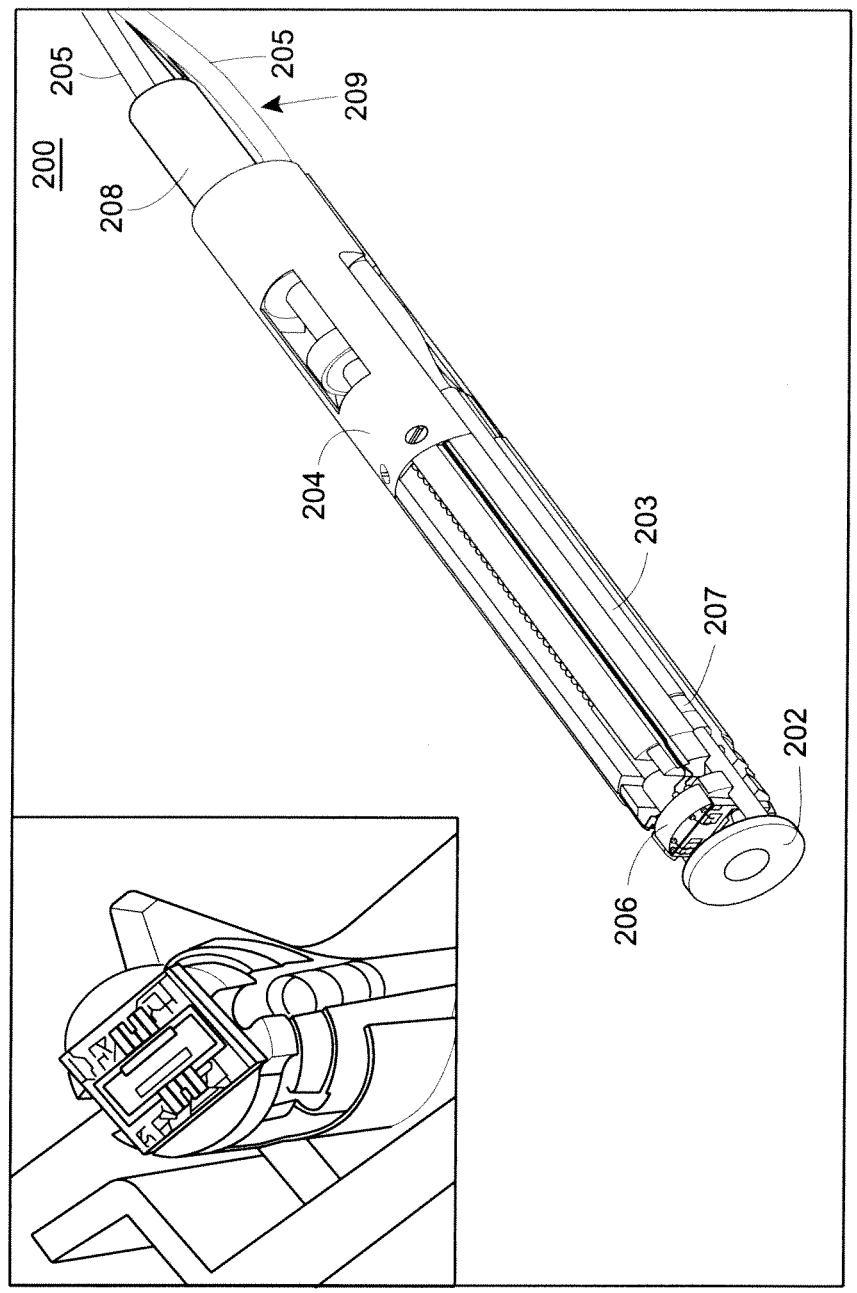
FIG. 10 illustrates another example implementation of a dual-axes optical probe.

FIG. 10 illustrates another dual-axes probe 200 similar to that of probe 100 but designed for tighter applications, and thus having a 5 mm diameter parabolic mirror 202 at a distal end and corresponding smaller housing 204. MEMS scanning chip 206 connected to two beam channels, each formed of an optical fiber 205 with a graded index (GRIN) collimating profile 203 for providing respect illumination beams to respective Risley prisms 207 in each channel. The vertical scanner, in this example a drive motor 208, is shown at a proximal end 209 of the probe 200.

Figure 14A:
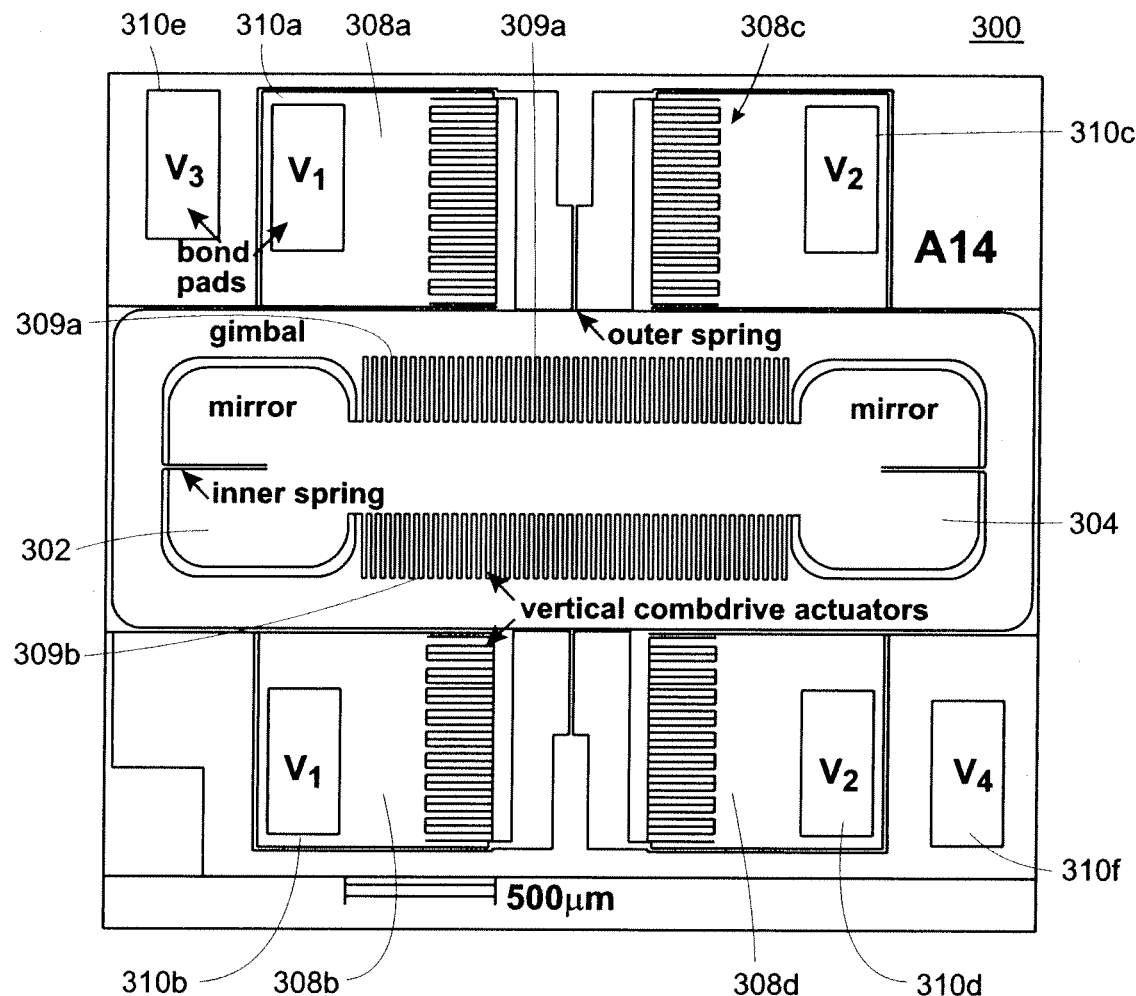
FIG. 14A illustrates a MEMS fabricated micro-mirror for the dual-axes scanhead of FIG. 12.

Both the dual-axes configurations in probes 100 and 200 have a scanning mirror. For the probe 100, the scanning mirror 120 is shown. The scanning mirror is a MEMS fabricated micro-mirror that performs high speed scanning while maintaining a fixed intersection of the two beams, below the tissue surface. FIG. 14A illustrates a MEMS mirror 300 that may be used as the scanning mirror 120. The mirror 300 uses a gimbal geometry to perform scanning to collect horizontal (XY-plane) cross-sectional images, and rotation around an inner and outer axes defined by the location of the respective springs, is shown by the scanning electron micrograph (SEM) in FIG. 14A, scale bar 500 gm. The overall structure has a barbell shape with two individual mirrors 302 and 304 that have active surface dimensions of 600×650 μm$^2$ in the illustrated example. A 1.51 mm long strut 306 connects these two mirrors so that the illumination and collection beams preserve the overlapping focal volume in the tissue. Electrostatic actuation in each direction is provided by two sets of vertical comb-drives. Comb drives 309a and b control rotational scanning of the mirror 300 along one axis, while comb drives 308a-d control rotational scanning of the mirror 300 along another axis orthogonal to the first. There are 4 actuation voltages (V1, V2, V3, and V4) that provide power to the device and are connected to bondpads 310a-310f (with voltage connections as shown) via an ultrasonic wedge bonding technique. The comb drives 308 and 309 are situated orthogonally to allow for scanning in two dimensions. For two dimensional (en face) imaging, rotation around the outer axis (V1 and V2) is resonantly driven with a sine wave, while rotation around the inner axis (V3 and V4) is driven at DC with a sawtooth waveform.

Fabrication of the mirror 300 may involve 4 deep-reactive-ion etching (DRIE) steps to achieve self-alignment of the combdrive fingers in the device layers by transferring mask features sequentially from the upper to lower layers and to remove the backside of the substrate behind the mirror and release the gimbal for rotation. For the illustrated example, images can be acquired at rates up to 30 frames/sec with a maximum field-of-view of 800×400 μm$^2$. The mirror surface is coated with a 12 nm thick layer of aluminum to increase reflectivity. This is particularly important for fluorescence imaging because of the low collection efficiency of the dual-axes architecture. The reflectivity increases a factor of two from 37% to 74% at visible wavelengths compared to bare single crystalline silicon. Since the imaging beam reflects off the MEMS scanner twice before collection, the effective increase in photon collection is a factor of four.

The parameters of the scanner may be characterized for quality control purposes prior to use in the microscope. First, the flatness of the mirror is measured by an interferometric surface profiler to identify micro-mirrors that have a peakto-valley surface deformation <0.1 µm. In an example environment, the root mean square (RMS) roughness of the mirror surface itself should be ~25 nm. Identifying devices with this surface profile ensures a high optical quality of the reflected beams. Then, the static deflection curve is measured, and optical deflections of ±4.8° are achieved at 160 V for the outer axis, and ±5.5° at 170 V for the inner axis. The difference between the two is expected to be mainly from the non-uniform etching profile of DRIE. The frequency response of the MEMS mirror may be obtained using a driving voltage of (77+58 sin 2πωft) V. The torsional resonance frequencies ($f_o$) were at 500 Hz with ±12.4 deg optical deflection, and 2.9 kHz with ±7.2 deg optical deflection for the outer and inner axes, respectively. The parametric resonances can sometimes be observed in the inner axis near frequencies of $2f_o/n$, where n is an integer ≥1. This phenomenon is caused by the nonlinear response of the torsional combdrives, which leads to sub-harmonic oscillations.

Figure 14B:
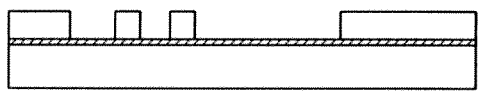
FIG. 14B illustrates example MEMS processing steps for forming the micro-mirror of FIG. 14A.
Figure 14B:
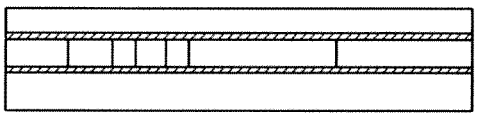
Figure 14B:
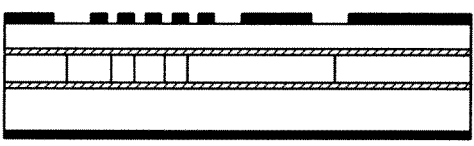
Figure 14B:
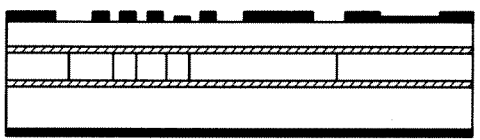
Figure 14B:
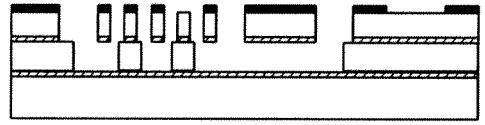
Figure 14B:
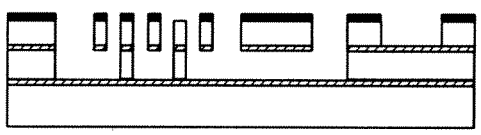
Figure 14B:
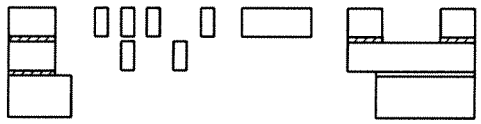

The fabrication process, shown in FIG. 14B, starts with a silicon-on-insulator (SOI) wafer composed of a silicon substrate, buried oxide, and silicon lower device layers that are 530, 1, and 30 µm thick, respectively. A deep-reactive-ion-etch (DRIE) of coarse patterns, including the combdrives and trenches, is performed on the SOI wafer with Mask 1 (step 1). Next, an oxide layer is grown on a plain silicon wafer using a wet oxidation process. This wafer is then fusion bonded onto the etched surface of the SOI wafer (step 2). The yield is increased by bonding in vacuum, and the bonded plain wafer is ground and polished down to 30 µm thickness, becoming the upper device layer. The two oxide layers between the silicon layers provide electrical isolation, and act as etch stops for DRIE allowing precise thickness control. The frontside of the double-stacked SOI wafer is patterned and DRIE etched to expose the underlying alignment marks in the lower device layer. Then, a low temperature oxide (LTO) layer is deposited on both sides of the wafer. The frontside layer is patterned by two masks. The first mask (Mask 2) is the self-alignment mask (step 3), and is etched into the full thickness of the upper LTO layer. The second mask (Mask 3) is mainly for patterning the electrodes for voltage supplied to the lower device layer (step 4). It goes through a partial etch leaving a thin layer of LTO. The alignment accuracy of each step needs to be better than g/2, where g is the comb gap. Since most devices have 6 µm comb gaps, this leads to a required alignment accuracy of better than 3 µm.

Good alignment accuracy is important in minimizing failures due to electrostatic instability during actuation. These three masks eventually define the structures in the upper, lower, and double-stacked layers of the MEMS mirror 300. After the frontside patterning is done, the LTO layer at the wafer backside is stripped (step 5). The wafer is cleaned and photoresist is deposited on the backside. Then, frontside alignment marks are patterned. Next, the upper silicon layer is etched with the features of Mask 2 in DRIE. Then, a thin LTO and buried oxide layer is anisotropically dry-etched. Finally, the lower and upper silicon layers are etched (DRIE) simultaneously with features patterned by Mask 2 and 3, respectively (step 6). For backside processing, the wafer is bonded to an oxidized handle wafer with photoresist. The backside trenches are patterned with Mask 4 on photoresist (step 7). The backside trench should etch through the substrate to release the gimbal structure, so handle wafer bonding and thick resist is required for DRIE. Alignment to the frontside features are accomplished by aligning to the previously etched patterns. After the substrate (530 µm) is etched by DRIE, the process wafer is separated from the handle wafer with acetone. After cleaning, the exposed oxide layer is directionally dry-etched from the backside. Finally, the remaining masking LTO and exposed buried oxide layer is directionally etched from the frontside.

Beyond the XY-plane scanning discussed above in regards to the MEMS mirrors 120 and 300, the probes 100 and 200 include a new axial (vertical) displacement control for Z-axis movement. In an example, the axial (Z-axis) displacement perpendicular to the parabolic mirror 116 was performed with a computer-controlled piezoelectric actuator (Physik Instrumente GmbH) that moved a slider mechanism 180, which includes 1 or more (e.g. 3) mechanical supports 150 supporting the MEMS chip 124, as shown in FIG. 13. The Z-axis control adjusts the imaging depths for collection of 3D volumetric images. The distal end of the support sliders 150 has a mounting surface for a printed circuit board (PCB), which supports the MEMS chip 124, wire bonding surfaces (bondpads), and soldering terminals. Power is delivered to the mirror 116 via wires that run through the middle of the housing, and are soldered to the PCB terminals. The axial (vertical) scanning stage may be actuated by the closed-loop piezoelectric linear actuator. Finally, the entire probe 100 (or 200) assembly may be covered and sealed from the environment using UV-curing glue to prevent leakage of bodily fluids.

Instrument control and data acquisition are performed using a LabVIEW® platform and two control boards (National Instruments PXI-6711 and PXI-6115). The image field-of-view and frame rate are determined by the frequency and amplitude of the 4 control signals delivered to the micro-mirror 116. For each horizontal cross-sectional image, the micro-mirror is driven in resonance around the outer (fast) axis using a unipolar sine wave. Rotation of the inner (slow) axis is driven at the DC mode with a unipolar sawtooth waveform. This waveform is smoothed at the transition edges to avoid the introduction of high frequency ringing by the inner axis. The inner axis has its opposing combdrive actuator banks driven 180 deg out of phase to maximize the linear region of the angular deflection while the outer axis is driven with only one side of the combdrive banks in resonance. The step size and range of Z-axis displacement of the piezoelectric actuator may be computer-controlled. The PMT gain is also modulated electronically to adjust for the decreasing fluorescence intensity at greater tissue depths. Frame averaging can be performed to reduce noise at low signal levels.

Preliminary fluorescence images were collected in vivo in horizontal cross-sections with the miniature dual-axes confocal microscope in accordance with the examples above. A mouse was anesthetized and injected intravenously with a near-infrared dye (indocyanine green, Sigma-Aldrich Corp) at a concentration of 1 mg/ml. Images were collected with the mouse lying on the translational stage adjacent to the miniature dual-axes confocal microscope oriented in the inverted position. The ear of the mouse was placed flat against the SIL (fused silica hemisphere). The imaging parameters were the same as that used for the ex vivo images. A horizontal cross-sectional fluorescence image of blood vessels can be seen in the ear in FIG. 15A, scale bar 50 µm. A 3D volumetric image was generated from a z-stack of horizontal cross-sections collected from z=0 to 150 µm in 3 µm intervals using the piezoelectric actuator, as shown in FIG. 15B. All images were collected at 5 Hz with 5 frames averaging (1 second per image). The full z-stack was acquired in 50 seconds, and reveal minimal motion artifact.

To take advantage of the deep tissue penetration that can be achieved using the dual-axes confocal architecture, a miniature vertical (Z-axis) actuator using piezoelectric (PZT) thin films to rapidly scan the focal volume perpendicular to the tissue surface was developed. High actuations speeds are valuable in intra-vital microscopy because small animal (mouse) models have much larger relative breathing displacements and faster heart rates that can introduce motion artifact. Piezoelectric thin films were chosen because they can be integrated into silicon microstructures to leverage high-force capabilities with exceptional speed and displacement. The key design specifications for the axial (vertical) scanner (i.e., the Z-axis actuator) are range (>300 µm), speed (>10 Hz), size (<3 mm diameter), and linearity of motion. A folded (zig-zag) pattern of axial (vertical)-scanners actuator legs effectively doubles the physical range of the Z-axis actuator so that a motion of ~300 µm corresponds to an optical Z-axis scan distance of ~600 µm of the focal volume. This axial distance is sufficient to image the epithelium and vascular endothelium in small animal models. Real-time operation is needed to minimize motion artifact caused by respiratory displacement, heart beating, and organ peristalsis. While 4 Hz is adequate to overcome these motions, the materials that we are developing can provide Z-axis actuation at speeds up to 30 Hz. Moreover, the package dimensions of these actuators can be reduced to millimeter scale to accommodate the small size of the scanhead. Finally, these materials provide smooth, linear motions as a function of drive voltage or current to minimize hysteresis.

Other techniques for axial (vertical) scanning control may include miniaturized small brushless DC motors with sufficient stroke displacement and nearly adequate scanning speed, hydraulic or pneumatic systems, thermal actuation, electrostatic actuation, and bulk piezoelectric materials. Yet, the MEMS piezoelectric approach discussed herein has advantages over these techniques for Z-axis actuation. These other designs are considered less ideal for intra-vital microscope to perform in vivo imaging, either because of a limits to the amount of size reduction that can be achieved, linearity of response, response time, and limited range of axial displacement.

In contrast, the preferred MEMS approach described herein allows for tiny actuators to be developed based on novel actuation mechanisms that are possible only for devices fabricated on the micron scale. Actuators based on piezoelectric thin films in unimorph bending modes provide both large displacement and fast response time. The Z-axis actuation developed uses piezoelectric thin films, which can provide much larger displacement forces than most micro-actuation technologies. Thin film lead-zirconate-titanate actuators utilizing various combinations of unimorph bending profiles have been developed. In unimorph piezoelectric beams, the contraction of the piezoelectric thin films within the beam causes either an upward or downward bending of the actuator, converting a large piezoelectric actuation force into significant displacements. The operating principle uses two layers of platinum (Pt) to sandwich the piezoelectric element (PZT) deposited over a $SiO_2$ layer. A layer of gold (Au) is used to provide stiffness. The forces generated are much higher than that of other microactuators, and the displacements are much larger than that of most piezoelectric materials. In this proposed work, the upward and downward bending unimorphs will be combined to achieve net vertical motion in the Z-axis.

FIGS. 16A-16C illustrate example thin-film piezoelectric actuators, in the form of a miniature Z-stage (axial scanner) actuator having a 3×3 mm² silicon stage platform 190 that supports the micro-mirror 120, as shown in FIG. 16A. The platform is elevated by four 1 mm long thin-film PZT folding legs 192 attached at each corner. A side view of the stage (FIG. 16B) describes how the downward and upward bending thin-film PZT segments of the folding legs raises the stage platform and hence the micro-mirror from a baseplane 194. The Z-stage designs have demonstrated up to 120 µm of vertical displacement with a single set of folding legs at 20 V, measured by optical profilometry and shown in FIG. 16C. This result is very close to the theoretical displacement found from the model discussed below where 124 µm displacement was predicted at 20 V.

Preliminary design calculations have been performed to verify that actuators based on these principles can meet the desired Z-axis displacement and imaging speeds required. Stroke length of the vertical actuators driving the Z-axis motion can be calculated from the internal moment generated by the piezoelectric thin-film within the upward and downward unimorph segments, those segments' respective composite stiffnesses, and the length and number of actuators implemented in series. Using the standard layer thicknesses of the material stack, internal actuation moments at 20 volts of 1.7 and 7.8 mN·µm are anticipated for the upward and downward segments, respectively, and the composite stiffnesses of 78 and 6.0 mN·µm², respectively. Assuming actuators are situated at each corner of the Z-stage, thus preventing net rotation at the actuator tip, each segment of the legs driving motion has displacement $\Delta z_{seg}$, where a segment is either "up" or "down" bending, $$\Delta z_{seg} = \frac{EI_{seg}}{M_{tot}} - \sqrt{\left(\frac{EI_{seg}}{M_{tot}}\right)^2 - L_{seg}^2} \quad (1)$$

where $L_{seg}$ and $EI_{seg}$ are the length and composite stiffness of the respective segment, and $M_{tot}$ is the net internal moment in the beams generated by the piezoelectric film. To match boundary conditions at the intersection of the "up" and "down" segments, the net moment $M_{tot}$ is given by the following:

$$M_{tot} = \frac{\frac{1}{2}M_{up}L_{seg,up}EI_{seg,down} + (M_{up} - M_{down})L_{seg,down}EI_{seg,up}}{L_{seg,up}EI_{seg,down} + L_{seg,down}EI_{seg,up}} \quad (2)$$

The total vertical motion $\Delta z_{tot}$ of the stage is then given by the following:

$$\Delta z_{tot} = N_{fold}(\Delta z_{seg,up} + \Delta z_{seg,down}) \quad (3)$$

where $N_{fold}$ is the number of folds in the actuator legs leading to the stage. The stroke speed can be estimated by the natural frequency of the z-axis motion of the device. This natural frequency is dictated by the mass of the stage and mirror and the effective spring constant of the actuators. Spring constant, in turn, depends on the composite stiffnesses of the actuator as well as actuator length, such that the approximate natural total stiffness of the each segment of the leg is given by the equation:

$$k_{seg} \approx \frac{L_{seg}^3}{3EI_{seg}} \quad (4)$$

In turn, this produces a natural frequency of the system $\omega_n$ is given by the following:

$$\omega_n = \sqrt{\frac{(k_{seg,up}^{-1} + k_{seg,down}^{-1})^{-1} N_{leg}}{N_{fold} m}} \quad (5)$$

where $N_{leg}$ is the number of actuation legs (nominally 4) and m is the mass of the moving portion of the stage and the mirror, which is estimated at ~30 mg.

To provide even further displacement of the mirror 120 along the Z-axis, and to provide further vertical cross-sectional imaging in vivo operation, an axial (vertical) scanner was developed with even greater deflection (scanning) range. In some examples, the Z-stage design of FIG. 16B is modified to include multiple actuator legs, for example, four legs that when integrated in design result in larger deflections.

The multiple upward and downward bending MEMS legs are engaged in series at each corner of the platform in a folded pattern to generate >500 µm net vertical displacement. A schematic (side view) of the device showing two sets of folded thin-film PZT folding legs 196a,b and 196c,d stacked in series is shown in FIG. 17A. Motion of the downward and upward bending segments is synchronized to coordinate the overall vertical displacement. The expected displacement from our model with four sets of folding legs is shown in the dashed curve in FIG. 17B, and is compared with the experimentally measured motion from one set of legs. The trade-off that is incurred for extending the range of the multi-fold device is a reduction in bandwidth. However, the bandwidth of 390 Hz measured in the example of FIG. 16B corresponded to 55 Hz with the micro-mirror load. The reduced bandwidth with the example of FIG. 17A is expected to exceed 195 Hz which corresponds to 27 Hz with the micro-mirror load. This performance is sufficient to perform in vivo imaging. If displacement of the next generation device does not meet the desired specifications, the actuator lengths can be further increased, resulting in a tradeoff between actuation speed and displacement. We can also increase the operating voltage up to 30 V without exceeding the maximum electric field strength of the PZT film.

From the model of axial displacement discussed in with respect to FIGS. 16A-16C, the relationship between the Z-axis displacement and natural frequency versus actuator length in the four leg, two fold configuration described above is shown in FIG. 18. This graph reveals the tradeoff between actuator length ($L_{seg,up}+L_{seg,down}$) in microns, vertical displacement in Newtons, and natural frequency in Hertz. As expected, the Z-axis displacement increases with the length of the actuator. From our model, the natural frequency of the actuator exceeds 7.5 Hz for the full range of actuator lengths. These speeds are adequate to overcome much of the motion artifact expected with live animal imaging. Thus, we can fabricate devices with a wide range of actuator lengths that will meet the performance specifications for the axial displacement needed to vertically scan the full thickness of the epithelium (>500 µm). This range provides great flexibility in the process flow for fabrication of these actuators. As can be seen, there is a wide range within the design space for which the design requirements in terms of speed and displacement can both be met.

In addition to geometrical design, the layer thicknesses will be also optimized to maximize vertical (Z-axis) displacement. The process flow for fabrication of the proposed Z-axis actuation system is shown in FIG. 19. First, four piezoelectric (PZT) thin-film stacks are deposited onto a silicon-on-insulator (SOI) wafer at the corners of a mirror platform, shown in 1). Then, a silicon deep-trench etching process defines the static structural components of the actuators, such as the stage itself and the connections between the actuator folds, shown in 2). Next, the actuator is then coated with photoresist for protection of the structural components, shown in 3). Etch holes are then developed to allow for release via an isotropic gaseous silicon etch, shown in 4). The resulting system consists of rigid silicon microstructures connected to the baseplane of the Z-stage by the very flexible piezoelectric actuators.

The final step of the Z-stage development is integration with the lateral scanning micro-mirror and assembly in the dual-axes scanhead. One aspect is to provide an electrical interconnect to the micro-mirror through the Z-stage. One technique to provide power to the mirror is to attach thin wires to the micro-mirror and Z-stage base via ultrasonic wire bonding, then to move the micro-mirror into place onto the stage. Alternatively, the micro-mirror may be connected using conductive epoxy to electronic interconnects on the moving portion of the stage that have been routed beside the vertical actuator. Finally, the micro-mirror may be connected directly to the actuators, with the vertical actuator input used as a carrier signal for micro-mirror actuation, utilizing wide resonant frequency separation to produce separate responses.

Once the lateral scanning micro-mirror is in place, the actuators will preferably operate through a large number of cycles at 20 V, a somewhat larger voltage than that typically used for thin-film PZT devices, which most often operate in the 5 to 10 V range. Thin-film devices at this lower voltage have been operated for billions of cycles, and calculations based on accelerated testing of PZT films at higher voltages do not predict problems with thin-film deterioration or failure at 20 V.

The design may be further enhanced using integrated position sensing, via piezoelectric or piezoresistive strain sensors, that provide feedback control to linearize the motion of the Z-axis stage. This feature would minimize any distortion in the vertical cross-sectional image.

The design provides a Z-axis actuator using thin film piezoelectric material that provides a displacement of >500 µm at 10 Hz or faster. The device may be integrated and synchronized with the lateral scanning micro-mirror and distortion free vertical cross-sectional images may be collected over the full thickness of the epithelium in the colon and breast. Furthermore, this actuator should have the robustness and reliability to collect images in live animals that are free of motion artifact.

FIGS. 20A and 20B illustrate another example MEMS mirror that can be integrated with the 3-Stage of FIG. 20A. In order to perform real time vertical cross-sectional imaging, we also need a fast lateral scanning micro-mirror that complements the Z-axis actuator. With use of post-objective scanning in the dual-axes architecture, we can achieve a very large field of view (>800 µm). This level of performance requires a robust, high speed lateral scanner for use in live animal imaging. The gimbaled MEMS mirror 120 may be used to perform two-dimensional (XY-plane) scanning. That scanner was packaged in a miniature (5 mm diameter. FIG. 7) dual-axes scanhead to collect horizontal cross-sectional images. The MEMS mirror in FIGS. 20A and 20B is designed for one dimensional (X-axis) scanning only, where a similar packaging geometry so that minimal changes will be needed to integrate this device into the miniature dual-axes scanhead.

The single scan axis design of FIG. 20A is a high-fidelity, one-dimensional comb-drive actuated micro-mirror, which still allows for obtaining vertical cross-sectional images in tissue at high scan speeds. This micro-mirror design employs a driving mechanism based on a physical phenomenon called "parametric resonance." Parametric resonance is an effect that causes maximum oscillations at certain frequencies to a non-linear mechanical system, where a periodic force acting upon a mechanical structure varies in both time and displacement. Similar non-linear phenomena have been observed for photons in photonic crystals, electrostatically forced nanowires, optically trapped atoms as well as for MEMS resonator devices.

The micro-mirror has a gold-coated movable silicon plate mirror that has two reflection surfaces (circular in shape in the illustrated example) connected to each other via a bridge, a fixed frame that includes two flexure beams to connect the mirror plate to the frame, and comb-shaped electrodes on the sides of both the mirror bridge and the frame. The surface geometry and dimensions of the mirror plate are primarily determined by the current packaging design of the miniature dual-axes scanhead. The flexure beams (shown partial in FIG. 20B, and extending outward away from the bridge for each of the mirror pads) serve as torsional springs to provide a restoring torque against the rotation of the mirror. Either a sinusoidal or a periodic sawtooth voltage signal will be applied to the comb-drives to provide actuation. The surfaces of the comb electrodes on one side will be coated with a thin layer of gold using a sputtering technology where approximately 100 nm thickness is sufficient to achieve >90% reflectivity at 785 nm (compared to 67% for aluminum). In other examples, the sputtering technique may achieve a rms roughness of ~13 nm.

An asymmetric spatial distribution of electric fields resulting from this electrode arrangement yields a torque M=M (t, θ) that drives the out-of-plane torsional vibration of the mirror. The dimensions of the flexure beams are selected to be on the order of 200 μm in length, approximately 10 μm in width, approximately 30-45 μm in thickness to yield the maximum rotational angle at the desired scanning frequency for a mirror surface. In some examples, other ranges may be used, including approximately 400-600 μm in length, approximately 30-50 μm in width, and approximately 20-30 μm in thickness to yield a maximum rotational angle at a desired scanning frequency for a given mirror structure. Theoretically, the structure experiencing parametric resonance has multiple resonance frequencies ω located near integer fractions of twice the natural (i.e. mechanical) resonance frequency $\omega_0$ as $\omega = 2\omega_0/n$, where for example n=1, 2, 3, 4, . . . 8. Here, we can excite the first mode of parametric resonance corresponding to n=1 for the device. Operational conditions ensuring the dynamic stability of parametric resonators are determined by a combination of the drive voltage and the drive frequency. The micro-mirror may be operated under an optimal condition that leads to stable scanner oscillations with a time-invariant vibrational amplitude. To make this behavior happen, we can identify the optimal condition by carefully modulating the drive voltage and frequency prior to the operation.

Large rotational angles can be achieved from the in-plane configuration of the MEMS mirror. Although air damping in atmospheric operations limits the upper bound for the rotational angle range, the mechanical requirements (e.g., more than ±5 deg at a drive frequency >3 kHz) for MEMS parametric resonators are feasible when the MEMS mirror is driven at a frequency equal to $\omega = 2\omega_0/n$, n=1, i.e., double the natural resonant frequency. Therefore, there is no need for special low-pressure or vacuum device packaging in this prototype.

The scanning micro-mirror of FIG. 20A can be fabricated from a silicon-on-insulator (SOI) wafer using a 3-mask standard micromachining process, including silicon deep reactive ion etch (DRIE), aluminum sputtering, and oxide layer release by buffered hydrofluoric (BHF) acid etch. The simple device design based on the single-layer structure is expected to significantly reduce the complexity in the device fabrication and cost without compromise in performance. In particular, the proposed device fabrication eliminates a wafer bonding process involving the aforementioned high precision feature alignment, thus highly improving the manufacturing yield and the device reliability. The new design also requires a smaller device footprint, which will make it easier for the integration step with the Z-axis stage into the dual-axes scanhead.

To integrate the micro-mirror of FIGS. 20A and 20B with the Z-axis stage control, a polymer membrane (~200 μm layer thickness) was used between the micro-mirror and the Z-stage, as shown in FIGS. 21A-21C, to protect the folding legs of the Z-stage. FIG. 21A illustrates a scanning micro-mirror stage 400 that includes a micro-mirror 402 and support base 404 with bondpads. The stage 400 may be formed of a micro-mirror such as those described above. The stage 400 functions, along with the parabolic mirror element (not shown that combines with the stage 400 to form a mirror assembly), to focus the illumination beam into a sample and the collection beam from the sample, at an overlapping a region of interest coinciding with a confocal beam region when these two beams overlap. The stage 400 is thus configured to scan that confocal beam overlap region across either a lateral axis (X or Y) or a lateral plane (XY) in the sample. The polymer member 406 is positioned between the stage 400 and an vertical scanning stage 408 (e.g., a Z-axis scanning stage). The member 406 allows for wire bonding with standard ultrasonic techniques without damaging the folding legs. The polymer membrane layer 406 as a compliant structure and allows for the electrical pads to be fabricated for connection to the micro-mirror electrodes prior to assembly of the Z axis stage 408. With this approach, the wire bonding can be more compact and the polymer structure can be directly patterned. This feature allows for adjusting the stiffness of the actuators on the Z-axis stage 408 by accurately controlling (during spin-coating) the thickness of polymer-based compliant structure. In addition, during the assembly procedure, the folding legs of the Z-axis actuator may be individually calibrated and controlled to adjust for assembly error.

The design is capable of lateral scanning with high yield that achieves a mechanical rotational angle greater than ±5 deg. With use of post-objective scanning in the dual-axes architecture, afield-of-view >800 μm is achievable. Further, the integrated micro-mirror with the Z-axis stage is able to achieve vertical cross-sectional imaging with the miniature dual-axes intra-vital microscope at a frame rate of 10 Hz or faster.

FIGS. 22A-22C illustrate another example implementation of an optical probe as described herein, as may be used for multi-color dual-axes confocal microscopy. In the illustrated example, the configurations above have been adapted to perform multi-color imaging with excitation by laser light at 676 and 785 nm. In this design, a probe scanhead 500 includes two parabolic mirror elements 502 and 504, at a proximal end and a distal end respectively. The first parabolic mirror element 502 functions to collimate an illumination beam from an input beam fiber and communicate that collimated beam to the second parabolic mirror element 504 for focusing into the sample. Thus, the probe 500 uses two matching parabolic mirrors as the collimating and focusing elements, as shown in FIG. 22A, to achieve an achromatic system. The beams from the two fibers are deflected by a prism and collimated by the first parabolic mirror 502. Because the collimated beams are aligned parallel to each other, the second parabolic mirror directs the focused beams to intersect at a common focal point below the tissue surface 504. This feature allows for light over a broad spectral range to become focused to the same point below the tissue surface simultaneously. The addition of a second excitation wavelength can be used to demonstrate the use of the miniature dual-axes confocal microscope to study ligand-receptor interactions. A controller 506 controls operation of a Z-stage and mirror assembly 508 within the scanhead 500.

Using two parabolic mirrors in the optical path can have several advantages: 1) There is no need to use a GRIN lens which is long and not easily adaptable for different wavelengths; 2) the length of the probe's scanhead is reduced and becomes endoscope compatible for clinical imaging purposes; and 3) improved optical efficiency compared to that for GRIN lens fiber coupling.

Excitation at 676 and 785 nm from two semiconductor lasers is delivered into a single mode optical fiber using a dichroic beamsplitter, and focused into the tissue using the same optics in the dual-axes scanhead (500 in FIG. 22A). Fluorescence in both spectral bands is collected off-axis, focused into another single mode fiber, and split by a second dichroic. A band-pass filter ($BPF_1$, 690 to 720 nm) ($BPF_2$, 805 to 845 nm) is placed in front of each photomultiplier (PMT) tube for separate detection of fluorescence from the two excitation sources, respectively. The gains are separately modulated to achieve appropriate amplification of the fluorescence signal from the deeper regions of tissue. The image resolution in the transverse ($\Delta x$ and $\Delta y$) and longitudinal ($\Delta z$) dimensions for the dual-axes architecture with uniform illumination can be determined from diffraction theory, and is given as the full-width-half-maximum (FWHM) in FIG. 22B. An illustration of the integrated 5 mm diameter dual-axes scanhead that performs vertical cross-sectional imaging is shown in FIG. 22C.

A controller, such as a processor or computer is coupled to lead wires connected to the scanhead to control lateral (horizontal) and vertical (longitudinal) scanning via control of the micro-mirror and Z-axis stage, respectively. While the system in FIG. 22A is described as a multi-wavelength system where the illumination beam contains two primary wavelengths, it will be understood that this is by way of example. The system may have a single-wavelength illumination beam and still retail at least one PMT for fluorescence detection, gain modulator, and amplifier, and frame grabber, where the probe (i.e., scanhead) is controlled by the controller, as shown. The controller may be embedded within the probe, but is preferably external to the probe.

The controller is generally illustrated and may include a processor and a memory and be coupled to an input device for user input, such as a keyboard, keypad, portable wireless device, etc. The control processes for controlling operation of the probe device in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. A computer will include a processor for performing instructions and one or more memory devices for storing instructions and data. Generally, however, a computer may also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device. Computer readable media suitable for storing computer program instructions and data include all forms of non volatile memory, media and memory devices, including by way of example semiconductor memory devices, e.g., EPROM. EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

In any event, with this configuration, vertical cross-sectional images can be obtained with a tissue penetration depth >500 µm and lateral field-of-view >800 µm. With a transverse resolution of ~2 µm, the fluorescence image can be digitized to 1000×1600 pixels, and oversampled by a factor of 2 to meet the Nyquist criteria. For scanning and image data collection, a high speed, 8 channel, 12 bit data acquisition board (e.g., National Instruments, PCI-5105) that can digitize 60×106 pixels/sec per channel may be used. At this rate, two fluorescence images, one at each incident frequency, can be acquired at speeds up to 30 Hz, which easily exceeds the preferred minimum range of 10 Hz. The vertical cross-sectional images have a high dynamic range (>40 dB), and may be digitized to 12 bits at 10 frames per sec, limited by the gain-settling time of the PMT. A high speed analog output board (National Instruments, PCI-6711) may be used to generate the waveforms needed to drive the scanning mirror, and will provide the triggers for the data acquisition board.

FIGS. 29A-29B illustrate a model of the light path traveled by the illumination and collection beams in a miniature (5 mm) dual-axes design, shown in FIG. 29A. In this model, the collimated input beam reflects off the surface of a parabolic mirror and is laterally scanned by the micro-mirror. With a scan angle of 6 deg, the device can achieve a FOV of ~800 µm, as shown in FIG. 29B. Note that post-objective scanning produces an arc-surface rather than a plane so the value in the planar projection is slightly smaller. The spot diagram in FIG. 29C shows the overlap of the two beams using a SIL, and defocusing occurs without the SIL, as shown in FIG. 29D, due to spherical aberrations at the air-tissue interface. In addition, we find that vertical translation (large arrow) of the micro-mirror by ~400 µm results in ~500 µm axial motion of the focal volume.

In one embodiment of the invention, a method of detecting a carcinoma cell is provided, comprising the step of administering a detectably labeled polypeptide to a subject in an amount effective to detect the carcinoma cell, said polypeptide having a property of preferentially binding to the adenocarcinoma cell relative to a non-cancerous cell, and detecting said cancerous cell with an optical probe as described herein.

As used herein, a "detectably labeled polypeptide" is a polypeptide labeled with any fluorophore or chemical or protein tag that enables its visualization. Visualization carried out with the naked eye, or a device as described herein and may also involve an alternate light or energy source. Fluorophores, chemical and protein tags that are contemplated for use in the methods of the invention include but are not limited to FITC, Cy 5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, CyQUANT GR-DNA, Dansyl Cadaverine, Dansyl Cadaverine, MeOH, DAPI, DAPI-DNA, Dapoxyl (2-aminoethyl) sulfonamide. DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, eYFP (Enhanced Yellow Fluorescent Protein), FDA, FITC antibody conjugate pH 8.0. FlAsH, Fluo-3, Fluo-3 Ca2+, Fluo-4, Fluor-Ruby, Fluorescein, Fluorescein 0.1 M NaOH, Fluorescein antibody conjugate pH 8.0. Fluorescein dextran pH 8.0. Fluorescein pH 9.0. Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, Fura-2, GFP (S65T), HcRed, Indo-1 Ca2+, Indo-1, Ca free, Indo-1. Ca saturated, JC-1, JC-1 pH 8.2, Lissamine rhodamine, Lucifer Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent NissI stain-RNA, Nile Blue, Nile Red, Nile Red-lipid, NissI, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 70, Rhodol Green antibody conjugate pH 8.0, Sapphire, SBFI-Na+, Sodium Green Na+, Sulforhodamine 101, Tetramethylrhodamine antibody conjugate pH 8.0, Tetramethylrhodamine dextran pH 7.0, and Texas Red-X antibody conjugate pH 7.2. A worker of ordinary skill in the art will appreciate that there are many such imaging agents that can be used to visualize an agent of the invention, either in vitro or in vivo. As used herein, an "imaging agent" refers to any tag that may be attached or conjugated to an polypeptide of the invention.

Certain methods of the invention are those wherein effectiveness of a treatment for cancer in a human is determined comprising the step of administering a detectably labeled polypeptide to the human in an amount effective to label cancerous cells, visualizing a first amount of cells labeled with the detectably-labeled polypeptide, and comparing the first amount to a previously visualized second amount of cells labeled with the detectably-labeled polypeptide, wherein a decrease in the first amount cells labeled relative to the previously visualized amount of cells labeled is indicative of effective treatment. In these aspects, a decrease of 5% is indicative of effective treatment. In other aspects, a decrease of about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or more is indicative of effective treatment.

Other methods of the invention involve the acquisition of a tissue sample from a patient. The tissue sample is selected from the group consisting of a tissue or organ of said patient.

Polypeptides as contemplated by the invention are, in one aspect, 5 amino acids in length. In other aspects, the polypeptide is 6, 7, 8, 9, 10, 11, 12, 13, 14, 15, 16, 17, 18, 19, 20, 21, 22, 23, 24, 25, 26, 27, 28, 29, 30, 35, 40, 45, 50 or more amino acids in length.

It will be understood that, in various aspects, polypeptides contemplated by the invention incorporate modifications known in the art and that the location and number of such modifications are in certain aspects, varied to achieve an optimal effect.

"Effective amount" as used herein refers to an amount of a detectably labeled polypeptide sufficient to bind to and allow for visualization of the target cancer cell.

EXAMPLES

Example 1

Peptides have demonstrated tremendous potential for use as molecular probes to identify cell surface targets in vivo. In addition to high clonal diversity, small size, low immunogenicity and compatibility with fluorescence dyes, peptides exhibit rapid binding kinetics and high binding specificity. Targeting peptides have been developed using techniques of phage display, a powerful combinatorial method that uses recombinant DNA technology to generate a complex library of peptides for selection by preferential binding to cell surface targets. The protein coat of bacteriophage, such as the filamentous M13 or T7, is genetically engineered to express a very large number ($>10^9$) of different peptides with unique sequences to achieve high affinity binding (New England Biolabs, Inc. Ph.D.7™ phage display peptide library kit. Instruction manual 2006; ver 2.7). Selection is then performed by biopanning the phage library against cultured cells that overexpress the target (Zurita et al., Cancer Res 2004; 64:435-9; Kelly et al., Neoplasia 2003; 5:437-44; Kelly et al., Cancer Res 2004; 64:6247-51). The DNA sequence of candidate phage are then recovered and used to synthesize the peptide. Peptides can be administered topically onto the epithelium where they then diffuse in between the leaky junctions of transformed cells and bind to over expressed targets or they can be delivered systemically. Peptide binding to target receptors can be observed in vivo with intra-vital microscopy. Observing biological behavior at this level of detail can be used for disease detection, therapy monitoring, and drug discovery.

The ability to select peptides that preferentially bind to cell surface targets using the technique of phage display as described above has been demonstrated (Hsiung et al., Nature Medicine 2008; 14:454-58). In this approach, a library of M13 phage (Ph.D. 7, New England Biolabs, Ipswich, Mass.) that express a high diversity >$10^9$ of 7mer peptides on the PIII protein coat was biopanned against human epithelial (CRL-7869/Hs738.st) cells in culture (ATCC, Manassas, Va.). These cells exhibit a similar morphology to that of normal colonic epithelial cells, and are used to remove non-specific binders to cell surface targets. Over 97% of the phage was removed after 3 rounds of biopanning, and the unbound phage in the supernatant were collected and biopanned against freshly excised specimens of normal human colonic mucosa to provide additional removal of non-specific binding phage. The remaining unbound phage were collected and then biopanned against freshly excised specimens of human colonic adenoma, yielding ~6000 candidates after 3 rounds. The candidate phage were screened in groups of 10 by assessing for binding to HT29 (human colonic adenocarcinoma) cells in 8 well plates. The cells were first rinsed with phosphate buffer solution (PBS), blocked with 1% bovine serum albumin (BSA) for 5 min, and rinsed again with PBS. Then, approximately $2 \times 10^{10}$ pfu of each candidate phage diluted in 300 μL of cell culture media was added to each well, and incubated with 300 μl of 1:500 mouse M13 monoclonal antibody conjugated with FITC (Fitzgerald Industries, Concord, Mass.) for 1 hour at 37° C.

Following antibody incubation, cells were rinsed twice with PBS and imaging was performed with a confocal microscope (Leica TCS SP2) at a magnification of 10×. Binding of the phage to the surface of the HT29 cells (arrow), as shown in FIG. 23A, was evaluated by fluorescence intensity. The phage with peptide sequence "VRPMPLQ" exhibited ~20 times greater fluorescence intensity compared to wild-type phage, and was found on a BLAST (Basic Local Alignment Search Tool,) search to have partial homology (6 out of 7 amino acids) to the laminin-G domain of contactin-associated protein (Caspr-1) (Hsiung et al., Nature Medicine 2008; 14:454-58). The DNA of the candidate phage was sequenced, and the peptide probes were synthesized and conjugated to fluorescein using a hexanoic acid linker to the N-terminus at a purity of 99% by HPLC. In vivo demonstration of preferential peptide binding in a human subject on routine endoscopy is shown in FIG. 23B. First, fluorescence peptide (VRPMPLQ), 5 ml at a concentration of 100 μmol, was topically administered to a colonic adenoma and the immediately adjacent normal mucosa via a standard spray catheter, and then imaged at 50 μm depth with a confocal microendoscope, Cellvizio-GI (Mauna Kea Technologies, Paris, France). In the left half of the fluorescence image, significant peptide binding to colonocytes surrounding dysplastic crypts (adenoma) can be seen, compared much less fluorescence intensity from normal mucosa in the right half, scale bar 20 μm. The average fluorescence intensity from n=10 adenomas and adjacent normal mucosa was calculated from a 25×25 μm² region of colonocytes at three sites within each image, and the average contrast ratio was found to be 21±6 (Hsiung et al., Nature Medicine 2008; 14:454-58).

Example 2

Small animal models play an important role in the study of colon cancer biology because the natural history of these tumors develop over an abbreviated time course (between 6 to 12 months) compared to that of humans.

A genetically engineered mouse model has been developed that spontaneously expresses polyps in the distal colon and rectum (Hinoi et al., Cancer Res. 2007; 67:9721-30; Akyol et al., Nat Methods 2008; 5:231-3). This small animal model can be used to demonstrate the imaging performance of the novel dual-axes confocal microscope and to evaluate affinity binding of the fluorescence-labeled peptides. The model is based on mutations in the adenomatous polyposis coli (APC) gene to initiate cancer development in the distal colon. Previous mouse models based on the APC gene expressed tumor mainly in the small intestine where it would be extremely difficult to access using techniques of intra-vital microscopy in a non-terminal experiment. A new mouse model of colon cancer has been developed that can express dypslastic lesions in the distal colon and forms invasive cancer for use to validate the miniature microscope and peptide probes described herein. The human CDX2 sequences confers preferential transgene expression in colonic epithelium in the adult mouse, and mice carrying a CDX2P-NLS-Cre recombinase transgene and a loxP-targeted Apc allele developed mainly distal colon tumors, with carcinomas seen in 6 of 36 (17%) of mice after 300 days. Like human colorectal lesions, the mouse tumors also show bi-allelic APC inactivation, β-catenin dysregulation, global DNA hypomethylation, and chromosomal instability.

FIG. 24 illustrates that the CPC;APC mouse model of colon cancer develops APC mutations under regulation by Cre recombinase, resulting in the development of polyps in the distal colon and rectum (box), scale bar 10 mm. This location can be easily accessed by a miniature intra-vital microscope to study the expression of molecular targets that appear with cancer transformation. Adenomas (dysplasia) also appear sporadically in the small intestine and cecum.

The predominantly distal distribution of lesions in affected mice implies that somatic defects that promote clonal outgrowth of epithelial cells with a single APC-mutant allele occur in a non-uniform fashion in the colon. Tumor burden in the mouse small intestine impacts on colon tumor development, and gender-specific effects on tumor multiplicity in the distal mouse colon mimic the situation in humans. The distal expression of colonic neoplasia in this genetically engineered mouse model allows for validation of the peptide binding to colonic adenomas in vivo. In FIG. 24, numerous dysplastic lesions that range in size from 2 to 5 mm can be seen in the distal colon (white box). In addition, 5 lesions can be seen in the small bowel (arrows), scale bar 10 mm.

The ability to image fluorescence-labeled peptides has been demonstrated with high target-to-background ratio in vivo in this mouse model of colon cancer. A rigid endoscope provides significantly better image quality than a flexible (fiber optic bundle), and was chosen to perform wide area fluorescence imaging. This small animal endoscope (Karl Storz Veterinary Endoscopy, Goleta, Calif.) consists of a 9.5 Fr (3 mm) diameter rigid Hopkins II 0 deg telescope with a 11.5 cm working length and a 3 Fr (1 mm) diameter instrument channel for performing tissue biopsy. Fluorescence excitation is produced with a 450 to 475 nm passband filter that can be manually switched into the optical path of a 175 W Nova Xenon light source, and is delivered to the endoscope via a 3 mm diameter fluid light cable with 250 cm length. Fluorescence images are collected with 510 nm barrier filter to block the excitation light, and are detected with a 3-chip color camera with an integrated parfocal zoom lens. Real time video can be recorded via firewire connected to a personal computer.

The rectum of the mouse was first cleaned of stool and debris by performing tap water lavage, and then the distal end of the small animal endoscope was lubricated and inserted into the rectum of the mouse. Once adenomas were identified on white light, shown in FIG. 25A, a 1 ml solution of FITC-labeled peptide "VRPMPLQ" at a concentration of 10 µM was applied through the instrument channel with a syringe, and allowed to dwell for ~10 minute, followed by gentle rinsing with PBS. The resulting fluorescence image, shown in FIG. 25B, demonstrated preferential peptide binding to the adenomas. The rectum was then rinsed vigorously with PBS. Complete removal of the peptide from the rectal mucosa was observed on fluorescence. Then, the FITC-labeled scrambled (control) peptide "QLMRPPV" was administered at the same concentration (10 µM). The fluorescence image from the control peptide is shown in FIG. 25C, and revealed significantly less fluorescence intensity (peptide binding) to the adenomas.

Example 3

Chemokine receptor CXCR7 was recently identified as a highly promising new molecular target of angiogenesis in breast cancer.

On immunohistochemistry, 97% of human primary breast tumors expressed CXCR7 in the tumor vascular endothelium, while the receptor was undetectable in normal breast tissue, as shown in FIG. 26C (Miao et al., Proc Natl Acad Sci USA 2007; 104:15735-15740). CXCR7 expression in tumor vasculature can be demonstrated on immunohistochemistry using the mouse monoclonal antibody 11G8 (Burns et al., J Exp Med 2006; 203:2201-2213). Invasive ductal carcinoma of the breast reveals CXCR7 expression in the tumor vasculature (arrow), magnification 10×, shown in FIG. 26A. Endothelial staining of a blood vessel (arrow) from a) is shown in FIG. 26B, magnification 40×. Normal breast tissue vasculature shows no CXCR7 expression, as shown in FIG. 26C, magnification 10×. CXCR7 negative blood vessels from c) are shown in FIG. 26D, magnification 40×. In addition, CXCR7 imaging agents also may detect a subset of breast cancer cells.

Furthermore, in a mouse model of breast cancer, the expression of CXCR7 was found to be co-localized with the endothelial marker CD31 in tumor-associated blood vessels. Human breast tumor cells were orthotopically implanted in a nude mouse, and CXCR7 expression is localized in the tumor vasculature on immunohistochemistry using the mouse monoclonal antibody 11G8, as shown in FIG. 27A. The expression of CD31 is shown in FIG. 27B, and outlines the endothelium of the blood vessels. An overlay of these two images in FIG. 27C shows co-localization of CXCR7 expression to the vascular endothelium. Moreover, CXCR7 mRNA has been found in vasculature of colon cancer, but the receptor was absent from normal vessels in this organ. Therefore, agents developed for non-invasive detection of CXCR7 also may be applicable for imaging angiogenesis in colon cancer as well. These data confirm expression of CXCR7 mRNA in vascular endothelium from breast tumors, but not normal breast vasculature. CXCR7 mRNA also was present in vasculature of malignant glioma and colon cancer, but the receptor was absent from normal vessels in these organs. Therefore, agents developed for non-invasive detection of CXCR7 may be applicable for imaging angiogenesis in several types of cancer.

To establish the kinetics of CXCR7-mediated uptake of ligands, the two chemokine ligands for CXCR7, CXCL11 and CXCL12 were fused to the fluorescent protein mCherry and expressed in 293T cells. CXCL11-mCherry and CXCL12-mCherry was collected from supernatants of stably transduced 293T cells. The fluorescent chemokines (~1 ng/ml) were added to human breast cancer cell line MCF-7, which is known to express CXCR7 endogenously (Burns J Exp Med 2006; 203:2201-2213).

High fluorescence signal was detected from either CXCL11 or CXCL12 in MCF-7 cells within 10 minutes of incubation as shown in FIG. 28, and the fluorescence signal could be observed readily in these cells up to 4 days later. The uptake of fluorescence-labeled chemokines in 293T cells stably transduced with CXCR7-GFP. CXCR4-GFP, or GFP alone was also tested. Similar to MCF-7 cells, 293T-C)<CR7 cells rapidly accumulate and retain CXCL11- and CXCL12-mCherry. By comparison, cells expressing CXCR4, the other known receptor for CXCL12, did not internalize detectable amounts of CXCL12-mCherry, and there was no uptake of either CXCL11-mCherry or CXCL12-mCherry in parental 293T cells. Collectively, these data show the remarkable capacity of CXCR7 to accumulate ligands, suggesting that imaging peptides targeted to CXCR7 will have a very high target-to-background ratio for intra-vital imaging studies in small animal models of breast cancer and tumor angiogenesis.

Example 4

Binding of synthetic or natural ligands to 7-transmembrane receptors activates the receptor, resulting in receptor activation and recruitment of β-arrestin, a cytosolic adapter protein. The protein interaction between CXCR7 and β-arrestin 2 has been used to develop a protein fragment complementation assay for detecting activation of CXCR7. CXCR7 and β-arrestin 2 are fused to inactive fragments of firefly luciferase (NLuc and CLuc, respectively). Ligand-dependent interaction of CXCR7 and β-arrestin 2 also brings together NLuc and CLuc fragments, which reconstitutes active firefly luciferase. Luciferase activity provides a quantitative assay for CXCR7 activation in living cells, as shown by the increase in bioluminescence following treatment with chemokine ligand CXCL12. Reporter cells stably expressing the CXCR7/β-arrestin 2 PCA have been used to identify an initial imaging peptide targeted to CXCR7, and this reporter system is used to screen for new targeting sequences.

Example 5

Cystine-knot peptides (knottins) are being utilized as the scaffold for developing imaging agents targeted to CXCR7. Knottins are small peptides that contain at least 3 disulfide bonds, making these peptides very stable and resistant to proteolysis, chemical degradation, and thermal denaturation (Kolmar, FEBS J. 2008; 275:2684-2690). The backbone loops in different knottins are variable in length and amino acid composition, making these loops amenable to substitution and molecular engineering (Christmann et al., Protein Eng 1999; 12:797-806). Several different bioactive peptides have been integrated into loops of knottin peptides, and directed evolution and library screening strategies have been used successfully to derive novel ligand binding activities with antibody-like affinities for their target molecules (Cwirla et al., Science 1997; 276:1696-1699; Wentzel et al., J Biol. Chem. 1999; 274:21037-21043; Lincoff et al., J Am Coll Cardiol. 2000; 35:1103-1115; Souriau et al., Biochemistry 2005; 44:7143-7155). Knottins may be synthesized synthetically or by recombinant expression systems, so production of these molecules is straightforward. The favorable properties of knottins have attracted interest in these peptides as scaffolds for high-affinity molecular imaging agents (Silverman et al., J Mol Biol 2009; 385:1064-1075).

As a first step toward engineering a knottin peptide for imaging CXCR7, the squash *Ecballium elaterium* trypsin inhibitor II (EETI II) was used as the scaffold. A peptide sequence based on the first 13 amino acids of secreted CXCL12 was inserted into the first loop of EETI II, based on previous studies suggesting that the amino terminus of chemokines confer binding specificity for CXCR7 and other chemokine receptors (Proost et al., Blood 2007; 110, 37-44). The sequence of first CXCR7-targeted knottin, based on EETI II peptide is GGC KPVSLSYRAPARFCKQDSDCLAGCVCGPNGFCGSA. The underlined peptides are the targeting motif, derived from the N-terminus of CXCL12. An N-terminal glycine was added to enable on resin addition of a fluorophore. C-terminal amino acids (SA) were added. Exposed loops permit substitution of amino acids. The substituted knottin was shown to activate CXCR7, as evidenced by increased bioluminescence from the CXCR7/beta arrestin complementation reporter. Activation of CXCR7 indicates that the engineered knottin binds to the receptor.

Ligands for CXCR7 activate the receptor, causing recruitment of β-arrestin. To determine to what extent the engineered knottin interacts with CXCR7, firefly luciferase complementation for CXCR7 activation was used as a reporter for binding of the peptide to the receptor. CXCR7/β-arrestin reporter cells were incubated with increasing concentrations of CXCR7-targeted knottin for 2 hours and then luciferase activity was quantified in living cells. The CXCR7-targeted knottin showed dose-dependent activation of CXCR7, showing that the peptide interacts with this chemokine receptor similar to chemokine ligands. It was also determined that the engineered knottin did not activate CXCR4, as measured by luciferase complementation for recruitment of β-arrestin to this receptor. Collectively, these data show that the engineered knottin selectively interacts with CXCR7 and not CXCR4, providing a scaffold for in vivo imaging of CXCR7 in breast cancer angiogenesis. Based on the data with chemokine ligands, it is highly likely that the targeted knottin is internalized into cells by CXCR7, substantially enhancing molecular detection of this receptor in mouse models of breast cancer. Furthermore, these studies establish CXCR7//β-arrestin complementation as a reporter strategy for identifying new CXCR7-targeted peptides.

Example 6

Peptides that affinity bind to over-expressed cell surface targets in mouse models of colon and breast cancer are selected using techniques of phage display. The lead candidates are fluorescence-labeled with near-infrared dyes to achieve the tissue penetration depths expected and used to validate binding with the miniature, multi-color dual-axes confocal microscope described herein.

Peptides that bind specifically to dysplastic rather than to hyperplastic colonic polyps are identified in the CPC;APC mouse model of colorectal cancer. These mice form polyps in the distal colon and rectum, and the pathology cannot be distinguished by either direct observation or endoscopic visualization with standard white light. This is the same challenge that physicians face when encountering polyps on routine screening with colonoscopy in human patients. Acyclic 12mer phage display library (New England Biolabs, Ipswich, Mass.) is administered to the CPC;APC mice when they begin to develop polyps at age ~20 weeks. The library is administered intravenously so that peptides that bind to targets expressed over the entire depth of the dysplastic crypts are selected to adequately evaluate the vertical cross-sectional imaging capability of the miniature dual-axes confocal microscope (>500 μm).

CPC;APC mice are screened by small animal endoscopy at age 20 weeks to assess for the presence of colonic polyps. Those that are positive are administered the phage library, containing ~$10^9$ unique phage clones, intravenously via a tail vein injection. After 10 minutes to allow for the library to circulate, the mice are euthanized and the colonic polyps are harvested. A 10 μm section of each polyp is cut and processed by routine histology to identify the pathology of the lesion (dysplastic versus hyperplastic). Phage are recovered from the remaining specimen after rinsing and homogenizing. The specific binding clones are precipitated, titrated, and sequenced. Specific binding is validated on resected specimens of dysplastic lesions. Additional CPC; APC mice are evaluated for colonic polyps on small animal endoscopy. Those that are positive are euthanized, and a segment of the distal colon and rectum is removed. The polyps are isolated and immediately frozen in OCT. The tissue are sectioned and panned with the amplified phage clones obtained from the in vivo panning and washed twice in PBS, blocked with 1% BSA and rinsed in PBS. Immunodetection are performed by incubating a FITC-conjugated monoclonal M13 antibody at a titer of 1:500. Tissue sections are rinsed, mounted using ProLong Gold mounting media with DAPI and imaging performed with a fluorescent microscope.

The peptides that bind specifically to dysplastic rather than to hyperplastic colonic polyps are screened to identify the candidates with the highest target-to-background ratios. Fresh biopsy specimens of dysplastic and hyperplastic polyps is collected from the CPC;APC mice as discussed above. These specimens are embedded in OCT media, cooled to 4° C., and cut into several 10 μm horizontal sections on a microtome. Paired sections (dysplasia and hyperplasia) are placed in triplicate in a 96 well plate, and an additional 10 μm serial section are taken from each specimen for histological (H&E) evaluation. Approximately $10^{10}$ pfu of each candidate phage diluted in 400 μL of complete media are added to each pair of mucosal sections followed by the addition of rabbit anti-M13 phage antibody (GenWay Biotech, Inc, San Diego, Calif.) at 1:100 dilution and by mouse anti-rabbit secondary antibody conjugated with FITC (Invitrogen, Carlsbad, Calif.) at 1:1000 dilution. After 10 minutes for incubation, the supernatant are removed and tissue is rinsed with PBS. The fluorescence intensity associated with phage binding to each tissue section is evaluated by fluorescence microscopy. The fluorescence intensity from 10 sites in the periphery of 5 glands in each image are recorded and averaged for dysplastic versus hyperplastic morphology. The target-to-background ratio is determined by dividing the mean fluorescence intensity from the dysplastic specimen with that from the hyperplastic. Unique phage clones are identified with a target-to-background ratio >10 for the intra-vital imaging studies with the multi-color dual-axes confocal microscope on vertical cross-sections. A control peptide is derived from each specific binding peptide by scrambling the sequence. The scrambled sequence is compared to that of known ligands to avoid regions of local similarity using the NIH BLAST (Basic Local Alignment and Search Tool) database. These peptides are synthesized and a fluorescent dye molecule is attached to the N-terminus.

In vivo binding of the candidate peptides in the CPC;APC mouse model of colon cancer is validated using the existing miniature dual-axes confocal microscope that performs horizontal cross-sectional imaging. This study assesses the binding specificity of candidate fluorescence-labeled peptides to distinguish between dysplastic and hyperplastic polyps. CPC;APC mice are screened every two weeks from age 20 to 50 weeks of age for the presence of polyps.

Imaging is performed by first cleaning out stool and debris with tap water delivered through a 3 cc syringe from the distal colon and rectum of the CPC;APC mice known to have polyps on screening endoscopy. The peptides labeled with Alexa Fluor 750 are diluted in PBS at concentrations of 0.1, 1, and 10 μmol and injected via the tail vein. After 10 minutes for circulation, the distal end of the miniature dual-axes microscope is inserted into the rectum and placed in direct contact with the polyp. Fluorescence images with excitation at 785 nm are collected in horizontal cross-sections at depths ranging from 0 to 500 μm in 100 μm intervals, and the target-to-background ratio is measured at each depth. A pinch biopsy is collected from the polyp and is processed for routine histopathological evaluation to validate the presence of dysplasia versus hyperplasia. Each candidate peptide is evaluated for the highest target-to-background ratio, the depth of detection over the range spanning from 0 to 500 μm, and the lowest concentration of peptide needed. The 3 most promising peptides are used for the vertical cross-sectional imaging studies as described herein.

Candidate peptides that bind to the chemokine receptor CXCR7 and not to normal tissue in a mouse xenograft model of breast cancer using techniques of phage display are also identified.

Acyclic heptapeptide phage display library (C7, New England Biolabs, Ipswich, Mass.) is used to identify additional peptide sequences that bind to and activate CXCR7. These peptides are inserted into a surface loop of a knottin scaffold. Peptides identified from this constrained, cyclic peptide library retain high affinity binding to CXCR7 when inserted into the constrained loop structure of the knottin scaffold.

Phage are incubated with human dermal microvascular endothelial cells (HDMEC) (purchased from Lonza) stably transduced with CCCR7-GFP or control HDMEC stably transduced with GFP alone. Control HDMEC do not express CXCR7 by RT-PCR, similar to published data for human umbilical vein endothelial cells (Burns J Exp Med 2006; 203:2201-2213). Incubations are performed for 2 hours at 37° C. to identify phage sequences that are internalized in a CXCR7-dependent manner, similar to chemokine ligands for the receptor. The cells are then washed 3 times with an acidic saline solution (pH 2.0, 5 minutes per wash) at 4° C. This protocol removes chemokines bound to cell surface CXCR7. Cells are lysed to recover and amplify internalized phage as described previously (Kelly Cancer Res 2004; 64:6247-51). Pools of phage internalized in HDMEC-CXCR7 cells are used for the next round of screening on HDMEC-CXCR7 and HDMEC-control cells, and a total of 5 rounds of phage incubation and recovery is performed. After 5 rounds of screening, 25 different phage clones internalized and recovered from 231-CXCR7 cells are sequenced and up to 25 different phage clones recovered from control cells to determine target peptide sequences. Any sequences that are common to both HDMEC-CXCR7 and HDMEC-control cells are excluded.

To establish specific binding of peptides for CXCR7, the firefly luciferase PCA is used for ligand-dependent recruitment of β-arrestin 2 to CXCR7. Chemokine ligands or CXCR7-targeted knottins activate this reporter system, producing bioluminescence as a quantitative measure of binding and indirect assay for CXCR7-dependent internalization. Five phage clones most highly represented among sequences recovered from HDMEC-CXCR7 cells are selected. As a negative control, one phage clone that was identified only in control HDMEC cells is selected. 231 CXCR7/β-arrestin 2 reporter cells are incubated with ~$10^{10}$ pfu of each phage for 2 hours at 37° C. The activity of the firefly luciferase PCA in intact cells is then quantified using an IVIS Spectrum system (Caliper).

A protocol has been published for chemical synthesis and refolding of an engineered knottin based on the human Agouti related protein (AgRP) (Silverman et al. J Mol Biol 2009; 385:1064-1075). Similar to the EETI II knottin, exposed loops in AgRP also may be substituted with specific targeting peptides (Silverman et al., J Mol Biol 2009; 385:1064-1075). To facilitate future translation to imaging studies in humans, the AgRP knottin is used for this research, expecting that using a human peptide will reduce greatly the likelihood of an immune response against the imaging peptide in patients.

The AgRP knottin is synthesized with the 3 optimal CXCR7-targeting peptides described above inserted into exposed loop 4, a site used successfully by other investigators for engineering targeted knottins (Silverman et al., J Mol Biol 2009; 385:1064-1075). An AgRP knottin with the same modified CXCL12 peptide sequence is synthesized as a positive control, and a knottin containing the negative control sequence used in the phage experiments described above is also generated. All peptides have a C-terminal Flag epitope tag added, which allows knottins to be detected by immunohistochemistry using an antibody to this epitope. A prior study has shown that a C-terminal epitope tag does not affect high-affinity binding of engineered knottins to specific target proteins (Silverman et al., J Mol Biol 2009; 385:1064-1075). These peptides are synthesized with an Alexa Fluor 750 fluorescent dye molecule attached to the N-terminus. Synthesis and quality control analyses are accomplished as described for the colorectal adenoma peptides.

Different AgRP-based peptides are tested for internalization in CXCR7-expressing and control HDMEC and 231 breast cancer cell lines. Cells are incubated with increasing concentrations of each knottin (0-1 μM) for various periods of time (0-120 minutes) (n=4 per condition), washed with PBS, and then assayed for fluorescence intensity (IVIS Spectrum, Caliper). In parallel cultures of cells, confocal microscopy is used to image subcellular localization of fluorescent knottins in HDMEC and 231 cell lines.

For knottins that show CXCR7-dependent accumulation in cells, competition binding experiments is performed to determine to what extent each knottin binds to the CXCL12 recognition site in CXCR7. HDMEC-CXCR7 and 231-

CXCR7 breast cancer cell lines are incubated with knottin peptide at the optimal concentration and time determined above in combination with 500 ng/ml CXCL12, a concentration >1000-fold more than the $EC_{50}$ for CXCL12-CXCR7 binding. Accumulation of fluorescent knottin is quantified by fluorescence intensity and analyzed by confocal microscopy. These data identify promising CXCR7-targeted knottins for the intra-vital imaging studies in mice. The in vivo imaging performance of the miniature, multi-color dual-axes intra-vital microscope is demonstrated on vertical cross-sections in the CPC;APC mouse model to observe preferential peptide binding to dysplastic rather than to hyperplastic colonic polyps. CPC;APC mice >20 weeks old are screened every two weeks for the presence of polyps using the small animal endoscope. Imaging is performed after first cleaning out stool and debris from the rectum of the mice with tap water delivered through a 3 cc syringe. The rectum of many of these mice prolapses outside of the perineum, and polyps can be identified directly. Those that have polyps present are injected with the peptide labeled with either Alexa Fluor 750 or Angiosense 680 the via tail vein. The peptides are diluted in PBS at concentrations of 0.1, 1, and 10 μmol. After 10 minutes to allow the peptide to circulate, the distal end of the miniature dual-axes confocal microscope is inserted into the rectum into contact with the polyp. A video stream of vertical cross-sectional images is collected. Then a pinch biopsy is collected from the polyp and processed for histology to evaluate for dysplasia versus hyperplasia. The vertical cross-sectional confocal images are analyzed by selecting 5 representative images from the video stream in both fluorescence channels based on the following criteria: 1) minimum motion artifact, 2) lack of stool or excess mucus preventing contact with the mucosa, and 3) recognizable crypt morphology. The fluorescence signal intensity is calculated by taking the mean of a pixel array corresponding to a 25×25 $\mu m^2$ square region within the colonocyte layer for three sites within each image. The signal noise is calculated by taking the standard deviation of the values in this pixel array. The fluorescence contrast ratio is obtained from the ratio of the mean polyp to the mean normal fluorescence intensity. The signal-to-noise (SNR) is obtained from the ratio of the mean polyp signal to signal noise for each image site. A similar set of calculations is performed for 3 sites of hyperplastic colonic mucosa. The target-to-background ratio is determined from the ratio of the mean fluorescence intensity at the lesion to that from the surrounding normal mucosa. Standard errors of the mean (s.e.m.) for the target-to-background ratio are reported based on the mice studied for each candidate peptide. The average fluorescence signal contrast and SNR attributed to the peptide are calculated by averaging the values obtained for each patient. Binding of the fluorescence peptide reagents to the tissue microarchitecture of the colonic adenoma is evaluated in 3 dimensions from volume rendered images produced from the z-stack of horizontal images (100 collected at 5 μm intervals) using Amira® software (Mercury Computer Systems, Inc Chelmsford, Mass.). The biostatistical evaluation is performed in a manner similar to that described for macroscopic imaging.

Example 7

It has been previously shown that CXCR7 is expressed in tumor vasculature of essentially all human breast cancers and ~30% of malignant breast epithelial cells (Miao et al., Proc Natl Acad Sci USA 2007; 104:15735-15740). It has also been established that CXCR7 is expressed in tumor blood vessels in orthotopic mouse breast cancer xenografts, allowing analysis of CXCR7-targeted imaging of tumor angiogenesis and tumor cells. MDA-MB-231 human breast cancer cells are implanted orthotopically into $4^{th}$ and $9^{th}$ inguinal mammary fat pads of adult (6-10 week) female NOD/SCID mice (2 tumors per mouse) as described previously. In each mouse, one tumor is implanted with 231 cells stably transduced with CXCR7, while the other tumor has 231 cells transduced with vector alone. Positions of each cell type in either the $4^{th}$ or $9^{th}$ fat pads is assigned randomly for each mouse to avoid any potential bias on imaging data. Implanting 231-CXCR7 and 231-control tumors in the same mouse allows for the investigation of CXCR7 imaging peptides in tumors that have CXCR7 only on the vasculature (231-control tumors) versus both the vasculature and tumor cells (231-CXCR7), reproducing the biology of human breast cancer. This allows direct comparisons of both types of tumors in the same animal, controlling for animal-to-animal variations in injected doses of CXCR7-targeted peptides and animal physiology. The CXCR7-targeted knottins with highest target-to-background ratios of accumulation in CXCR7-expressing versus control cells are tested. As a negative control, the knottin engineered with a non-CXCR7 targeted peptide is used. Imaging experiments begin after tumors reach ~5 mm diameter (typically within 2 to 3 weeks). The fur overlying each tumor is shaved with electric clippers to reduce scattering of fluorescence. Animals are injected via tail vein with a mixture of two different fluorescence-labeled peptides to identify CXCR7 expression in tumors and to define the tumor vasculature, respectively: 1) a CXCR7-targeted knottin labeled with Alexa Fluor 750 (10 mg/kg); and 2) Angiosense 680 (2 nmol fluorochrome per mouse), a well-established imaging probe for the vasculature labeled with a fluorescent dye emitting at 680 nm (VisEn Medical). Eight mice per group are used for each knottin (n=32 for 3 CXCR7-targeted and 1 control knottin). Co-injecting both imaging molecules allows for simultaneous definition of tumor blood vessels and localization of fluorescence from CXCR7 to either the vasculature or malignant breast cancer cells. Mice are imaged at multiple time points (10 minutes-48 hours) after injecting the CXCR7 targeted-knottin to determine kinetics of peptide accumulation and peak target-to-background signal for detecting CXCR7. Control mice are injected with the knottin that does not target CXCR7 in cell-based assays as determined herein. Mice receive a single injection of CXCR7 imaging peptide for these studies. Angiosense 680 is injected intravenously prior to each imaging examination because this agent is cleared rapidly from the circulation and does not provide sustained definition of tumor vasculature. Vertical cross-sectional images of CXCR7 and tumor blood vessels is performed with the dual-axes intra-vital microscope developed herein. The fluorescence images are acquired with tissue penetration depths from >500 μm within the tumor at each time point. Images are analyzed qualitatively to determine localization of CXCR7-targeted knottin in tumor vasculature, as defined by Angiosense 680, and within the tumor mass itself. Total accumulation of knottin in each tumor is quantified by intensity of fluorescence from Alexa Fluor 750 throughout the tumor volume. Three-dimensional images of tumor vasculature within each tumor are reconstructed, as defined by Angiosense 680 fluorescence, analogous to Z-stack reconstructions in standard confocal microscopy. Using these reconstructed images, knottin fluorescence associated with tumor blood vessels is quantified to determine accumulation of various CXCR7-targeted and control knottin peptides in both 231-control and 231-

CXCR7 tumors. Data are compared by two-sided t test to establish significant differences (p<0.05) among knottin peptides in tumor blood vessels and breast cancer cells.

Experiments described herein define an optimal CXCR7-targeted peptide and establish a protocol for optical imaging of this receptor in breast cancer. To validate in vivo data, breast tumor xenografts are excised for ex vivo histologic analyses immediately after imaging tumors in living mice. 231-control and 231-CXCR7 tumor xenografts are implanted into female SCID mice (n=5), mice injected with the CXCR7-targeted knottin that produced highest tumor-to-background fluorescence, and breast tumors imaged at the time of peak accumulation determined in the prior set of experiments. The control knottin is also injected into additional 5 tumor-bearing mice. After imaging, breast tumors are harvested from each mouse and tissues fixed for immunofluorescence staining (Miao et al., Proc Natl Acad Sci USA 2007; 104:15735-15740). Specimens are stained for CXCR7 and knottin peptide using monoclonal antibodies to the receptor and the Flag epitope tag on the knottin, respectively, to determine to what extent the imaging agent accumulates in CXCR7-expressing cells in vivo. Sections are co-stained with antibodies for blood vessels (CD31) and human breast cancer cells (human EpCAM) to localize CXCR7 and knottin peptide to tumor vasculature and malignant breast epithelial cells, respectively.

Example 8

Adult CPC;APC mice of both genders are used for the mouse colorectal cancer model. These mice have been genetically engineered and bred and carry the CDX2P9.5-G19Cre or CDX2P9.5-G22Cre alleles in the germline. These transgenic lines are crossed with the Gt(ROSA) 26Sorlm1sor (R26R) reporter mouse line to express CDX2P9.5-regulated transgenes and develop pre-malignant lesions (adenomas) in the distal colon beginning at 20 weeks of age. For peptide selection CPC;APC mice are first screened by small animal endoscopy at age 20 weeks to assess for the presence of colonic polyps. Those that are positive are administered the phage library, containing ~$10^9$ unique phage clones, intravenously via a tail vain injection. After 10 minutes to allow for the library to circulate, the mice are euthanized and the colonic polyps are harvested. Phage are recovered from the remaining specimen after rinsing and homogenizing. The specific binding clones are precipitated, titrated, and sequenced. For peptide validation, CPC;APC mice >20 weeks old are screened for the presence of polyps using the small animal endoscope. Imaging is performed after first cleaning out stool and debris from the rectum of the mice with tap water delivered through a 3 cc syringe. The rectum of many of these mice prolapses outside of the perineum, and polyps are identified directly. Those that have polyps present are injected with the peptide labeled with either Alexa Fluor 750 (10 mg/kg) or Angiosense 680 (2 nmol fluorochrome per mouse) the via tail vein. Mice bred for these experiments are evaluated for polyps and imaged every two weeks from age 20 to 50 weeks of age. The fluorescence-labeled peptides are injected in a volume of 0.3 ml. After 10 minutes to allow for the peptide to circulate, the distal tip of the intra-vital microscope is placed directed in contact with the polyp. A video stream is collected for post-processing. At the end of 50 weeks, the mice are euthanized by $CO_2$ asphyxiation, and the colon is harvested for histology.

Example 9

Adult (6-10 week old) female NOD-SCID mice (NOD.CB17-Prkdcscid/J strain) (Jackson Lab) are used for the mouse breast cancer xenograft model.

To establish orthotopic tumor xenografts in mammary fat pads, 6-10 week old female mice are anesthetized with 1-2% isoflurane and maintained on this same anesthetic delivered via nose cone throughout the procedure. The fur overlying the mid-abdomen and 4th/9th inguinal mammary fat pads bilaterally is shaved with electric clippers. Skin surfaces then are cleansed with chlorhexidine solution for 3×1 minute washes with fresh sterile gauze pads for each wash. After making an inverted Y-shaped incision through the abdominal skin, the skin overlying each inguinal mammary fat pad is reflected using autoclaved, curved forceps. $1×10^6$ human MDA-MB-231 breast cancer cells (obtained directly from the ATCC) stably expressing CXCR7 or vector control is suspended in 50 µl sterile 0.9% NaCl solution. These cells are injected through a 22 g needle into the lateral portion of each mammary fat pad. Incised skin surfaces are reopposed and held in place with wound clips. Wound clips are removed 7-14 days after surgery.

After the procedure, mice are placed in clean cages and observed throughout the recovery period. The mice are monitored on the first two post-operative days and then at least twice per week thereafter. Mice are euthanized for evidence of infection (skin erythema, purulent discharge) or persistent distress (abnormal posturing, excessive vocalization, persistent lack of movement, or moribund condition). Tumors (≈0.5 cm diameter) typically form within 2-3 weeks using this model.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:
1. An optical probe comprising:
   a probe housing assembly having a proximal end and a distal end for positioning at a sample, the probe housing assembly having a first beam channel configured to provide an illumination beam received from a laser source and having a second beam channel for receiving a collection beam from the sample; and
   a scanning assembly mounted at the distal end of the probe housing assembly, the scanning assembly comprising:
      a mirror assembly configured to provide a focused illumination beam path and a focused collection beam path at a region of interest within the sample where the illumination beam path and the collection beam path overlap to form a confocal beam region, the mirror assembly being configured to scan the confocal beam region along at least one transverse direction in the sample, and
      a vertical scanning assembly coupled to the mirror assembly and configured to scan the confocal beam region along a vertical direction to scan at different subsurface depths within the sample, wherein the vertical direction is orthogonal to the at least one transverse direction, wherein the vertical scanning assembly comprises a deflectable piezoelectric thin film region comprising a plurality of piezoelectric folding legs that are positioned to support the mirror assembly, each of the plurality of piezoelectric folding legs comprising a first segment and a second segment operably coupled to each other, wherein a portion of the first segment turns back on a portion of the second segment in an overlapping manner to form the folding legs, wherein, upon selectively folding and unfolding of the plurality of piezoelectric folding legs, the vertical scanning assembly is configured to move the mirror assembly along the vertical direction for scanning the confocal beam region to different subsurface depths within the sample.

2. The optical probe of claim 1, wherein the mirror assembly is further configured to scan the confocal beam region across a two-dimensional transverse plane in the sample.

3. The optical probe of claim 1, wherein the vertical scanning assembly is further configured to scan the confocal beam region from a vertical depth of the sample extending from an upper surface of the sample to a depth of at least 300 µm below the upper surface.

4. The optical probe of claim 3, wherein the vertical scanning assembly is further configured to scan the confocal beam region to a depth of 500 µm below the upper surface of the sample.

5. The optical probe of claim 1, wherein the first beam channel comprises a first optical fiber and the second beam channel comprises a second optical fiber, each of the first beam channel and the second beam channel configured to produce the illumination beam and the collection beam, respectively, in a collimated manner.

6. The optical probe of claim 5, wherein the first optical fiber has a gradient index lens configured to collimate the illumination beam, and wherein the second optical fiber has a gradient index lens for collimating the collection beam.

7. The optical probe of claim 5, wherein the first beam channel further comprises a Risley prism figured to adjust an alignment position of the illumination beam, and wherein the second beam channel further comprises a Risley prism for adjusting an alignment position of the collection beam.

8. The optical probe of claim 1, wherein the mirror assembly comprises a micro-mirror having a first reflector pad configured to reflect the illumination beam into the sample and a second reflector pad for reflecting the collection beam out of the sample.

9. The optical probe of claim 8, wherein the first reflector pad and the second reflector pad are connected by a strut to achieve dual movement of the first reflector pad and the second reflector pad.

10. The optical probe of claim 9, wherein the mirror assembly further comprises a comb drive configured to deflect the micro-mirror for scanning the confocal beam region along one transverse direction.

11. The optical probe of claim 9, wherein the mirror assembly further comprises multiple comb drives that are collectively configured to deflect the micro-mirror for scanning the confocal beam region along two orthogonal transverse directions.

12. The optical probe of claim 11, wherein the mirror assembly further comprises bondpads positioned to control deflection of the multiple comb drives in response to voltages being applied to the bondpads.

13. The optical probe of claim 8, wherein the micro-mirror is a MEMS fabricated mirror.

14. The optical probe of claim 8, wherein the mirror assembly further comprises a mirror element configured to reflect the illumination beam and the collection beam onto the micro-mirror.

15. The optical probe of claim 14, wherein the mirror element is a parabolic mirror.

16. The optical probe of claim 15, wherein the parabolic mirror has a central opening within which a solid immersion lens is mounted and wherein the parabolic mirror is configured to provide the focused illumination beam path and the focused collection beam path.

17. The optical probe of claim 15, wherein the parabolic mirror has a numerical aperture of less than 0.3.

18. The optical probe of claim 15, wherein the parabolic mirror has a numerical aperture that is 0.12.

19. The optical probe of claim 8, wherein the micro-mirror is mounted to the vertical scanning assembly.

20. The optical probe of claim 19, further comprising a polymer membrane configured to provide a compliant structure between the micro-mirror and the vertical scanning assembly.

21. The optical probe of claim 19, wherein the deflectable piezoelectric thin film region is positioned to deflect the micro-mirror in the vertical direction.

22. The optical probe of claim 21, wherein the piezoelectric thin film region is deflectable over a range of 0 to 100 µm and at a rate of at least 10 Hz.

23. The optical probe of claim 21, wherein the piezoelectric thin film region is deflectable at a rate of at least 30 Hz.

24. The optical probe of claim 21, wherein the piezoelectric thin film region is deflectable over a range of 0 to 300 µm.

25. The optical probe of claim 21, wherein each of the plurality of piezoelectric folding legs are individually attached to a base of the vertical scanning assembly and support the micro-mirror.

26. The optical probe of claim 25, wherein the vertical scanning assembly further comprises a piezoelectric actuator for each of the plurality of piezoelectric folding legs.

27. The optical probe of claim 26, wherein the piezoelectric actuators are individually calibratable for individually calibrating their respective folding legs to adjust alignment with respect to the micro-mirror.

28. The optical probe of claim 21, wherein the piezoelectric thin film region comprises a plurality of stacked piezoelectric folding legs that combine to deflect over a range from 0 to 500 µm at a rate of at least 10 Hz or higher.

29. The optical probe of claim 1, wherein the probe housing assembly has a diameter of 10 mm or below.

30. The optical probe of claim 1, wherein the probe housing assembly has a diameter of 5 mm.

31. A method of detecting a cancerous cell in a subject, the method comprising:
administering a detectably labeled polypeptide to the subject in an amount effective to detect the cancerous cell, said polypeptide having a property of preferentially binding to the cancerous cell relative to a non-cancerous cell; and
detecting the cancerous cell using the optical probe of claim 1.

32. A kit for detecting a labeled polypeptide administered to a subject in need thereof, the kit comprising:
a composition comprising a detectably labeled polypeptide having a property of preferentially binding to the cancerous cell relative to a non-cancerous cell;
the optical probe of claim 1, and instructions for use.

33. A confocal microscopy apparatus comprising:
a probe comprising:
  a housing assembly having a proximal end and a distal end for positioning at a sample, the housing assembly having a first beam channel configured to provide an illumination beam received from a laser source and having a second beam channel for receiving a collection beam from the sample; and
  a scanning assembly mounted at the distal end of the housing assembly, the scanning assembly having:
    a mirror assembly configured to provide a focused illumination beam path and to provide a focused collection beam path at a region of interest within the sample where the illumination beam path and the collection beam path overlap to form a confocal beam region, the mirror assembly being configured to scan the confocal beam region along at least one transverse direction in the sample, and
    a vertical scanning assembly coupled to the mirror assembly and being configured to scan the confocal beam region along a vertical direction to scan at different subsurface depths within in the sample, wherein the vertical direction is orthogonal to the at least one transverse direction, wherein the vertical scanning assembly comprises a deflectable piezoelectric thin film region comprising a plurality of piezoelectric folding legs that are positioned to support the mirror assembly, each of the plurality of piezoelectric folding legs comprising a first segment and a second segment operably coupled to each other, wherein a portion of the first segment turns back on a portion of the second segment in an overlapping manner to form the folding legs, wherein, upon selectively folding and unfolding of the plurality of piezoelectric folding legs, the vertical scanning assembly is configured to move the mirror assembly along the vertical direction for scanning the confocal beam region to different subsurface depths within the sample;
a light source configured to provide the illumination beam to the first beam channel, wherein the light source is a laser source; and
a photodiode assembly configured to receive the collection beam from the second beam channel and configured to produce an image of fluorescence energy contained within the collection beam.

34. The confocal microscopy apparatus of claim 33, wherein the light source is coupled to the first beam channel through an optical fiber and a collimating element.

35. The confocal microscopy apparatus of claim 34, wherein the collimating element is a parabolic mirror.

36. The confocal microscopy apparatus of claim 33, wherein the photodiode assembly is coupled to the second beam channel through an optical fiber and a collimating element.

37. The confocal microscopy apparatus of claim 33, wherein the photodiode assembly comprises a photomultiplier tube configured to collect fluorescence in the collection beam and a frame grabber configured to product a real time image of the collected fluorescence.

38. The confocal microscopy apparatus of claim 33, wherein the photodiode assembly comprises a plurality of photomultiplier tubes each for collecting fluorescence of a different wavelength in the collection beam, the photodiode assembly further comprising a frame grabber coupled to the plurality of photomultiplier tubes configured to produce real time images of each collected fluorescence.

39. The confocal microscopy apparatus of claim 33, further comprising a controller configured to provide control signals to actuate the scanning assembly to scan the sample over a volume of interest.

40. The confocal microscopy apparatus of claim 33, wherein the light source is configured to produce a first laser beam at a first wavelength and a second laser beam at a second wavelength, wherein the first laser beam and the second laser beam are combined to form the illumination beam as a multi-wavelength illumination beam.

41. The confocal microscopy apparatus of claim 33, wherein light source produces a pulsed beam.

42. The confocal microscopy apparatus of claim 33, wherein light source produces a continuous wave laser beam.

* * * * *